US011642464B2

(12) United States Patent
McDermott et al.

(10) Patent No.: US 11,642,464 B2
(45) Date of Patent: May 9, 2023

(54) SYRINGE TIP WITH FLUID WICKING DRIP FLANGES

(71) Applicant: BAYER HEALTHCARE LLC, Whippany, NJ (US)

(72) Inventors: Michael McDermott, Pittsburgh, PA (US); Kevin Cowan, Allison Park, PA (US); Michael Spohn, Fenelton, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 152 days.

(21) Appl. No.: 15/777,928

(22) PCT Filed: Nov. 23, 2016

(86) PCT No.: PCT/US2016/063449
§ 371 (c)(1),
(2) Date: May 22, 2018

(87) PCT Pub. No.: WO2017/091636
PCT Pub. Date: Jun. 1, 2017

(65) Prior Publication Data
US 2018/0344935 A1    Dec. 6, 2018

Related U.S. Application Data

(60) Provisional application No. 62/259,708, filed on Nov. 25, 2015.

(51) Int. Cl.
*A61M 5/31*    (2006.01)
*A61M 5/00*    (2006.01)
(Continued)

(52) U.S. Cl.
CPC .............. *A61M 5/31* (2013.01); *A61M 5/007* (2013.01); *A61M 5/345* (2013.01);
(Continued)

(58) Field of Classification Search
CPC ........ A61M 5/345; A61M 5/178; A61M 5/31; A61M 5/007; A61M 5/3134; A61M 5/344;
(Continued)

(56) References Cited

U.S. PATENT DOCUMENTS 1,553,710 A     9/1925  Muus et al.
1,929,221 A  * 10/1933  Swanson ................ B65D 23/06
                                                    215/41
(Continued)

FOREIGN PATENT DOCUMENTS

EP    2113212 A1    11/2009
EP    2243505 A3     3/2011
(Continued)

OTHER PUBLICATIONS

Kralchevsky, Peter & Nagayama, Kuniaki. (2001). Capillary Bridges and Capillary-Bridge Forces. 10.1016/S1383-7303(01)80052-1. (Year: 2001).*

(Continued)

*Primary Examiner* — Nathan R Price
*Assistant Examiner* — Anna E Goldberg-Richmeier
(74) *Attorney, Agent, or Firm* — Joseph L. Kent; James R. Stevenson; David Schramm

(57) ABSTRACT

Provided is a fluid wicking tip. The fluid wicking tip includes a plurality of drip flanges arranged to wick fluid between narrow spaces defined between any two drip flanges. The narrow spaces are dimensioned to facilitate wicking by capillary action. Also provided is a syringe that includes the fluid wicking tip. Also provided is a modular syringe system that includes a syringe and a sleeve configured to be slidably disposed over the syringe.

16 Claims, 64 Drawing Sheets

(51) Int. Cl.
   *A61M 5/34* (2006.01)
   *A61M 39/20* (2006.01)
(52) U.S. Cl.
   CPC .............. *A61M 2005/3103* (2013.01); *A61M 2005/3106* (2013.01); *A61M 2039/205* (2013.01)
(58) Field of Classification Search
   CPC .............. A61M 5/3205; A61M 5/32; A61M 2005/3117; A61M 2005/3118; A61M 2005/3106; A61M 2005/3103; A61M 2005/3101; A61M 2039/205; A61M 39/10; A61M 39/20; B05C 17/035; B05C 17/0341; A46B 11/0013; A46B 11/063; F28D 15/02; F28D 15/04; F28F 2215/10; F28F 2215/08; F28F 2215/04; F28F 2215/02; F28F 2215/00; B05B 14/10; B05B 14/00; B05B 1/28; A61J 1/2089; B65D 23/06; B65D 23/065; B65D 47/40; A47G 19/145
   See application file for complete search history.

(56) References Cited

U.S. PATENT DOCUMENTS

| | | | |
|---|---|---|---|
| 1,934,046 A | 11/1933 | Mario et al. | |
| 2,012,487 A * | 8/1935 | Carl | B65D 23/06 215/41 |
| 2,394,640 A | 2/1946 | Henry et al. | |
| 4,907,968 A | 3/1990 | Eisner et al. | |
| 5,002,533 A | 3/1991 | Jullien | |
| 5,290,255 A * | 3/1994 | Vallelunga | A61M 5/3271 604/110 |
| 5,324,527 A | 6/1994 | Coleman et al. | |
| 5,383,858 A | 1/1995 | Reilly et al. | |
| 5,527,297 A | 6/1996 | Paul | |
| 6,050,981 A | 4/2000 | Lampropoulos et al. | |
| 6,179,019 B1 | 1/2001 | Gowans et al. | |
| 6,537,257 B1 | 3/2003 | Wien | |
| 7,037,292 B2 * | 5/2006 | Carlyon | A61M 5/158 604/110 |
| 7,419,478 B1 | 9/2008 | Reilly et al. | |
| 7,666,169 B2 | 2/2010 | Cowan et al. | |
| 9,173,995 B1 | 11/2015 | Tucker et al. | |
| 9,199,033 B1 | 12/2015 | Cowan et al. | |
| 9,656,022 B1 * | 5/2017 | Russo | A61M 5/31576 |
| 9,770,563 B1 * | 9/2017 | Freeman | A61M 11/04 |
| 2002/0147429 A1 * | 10/2002 | Cowan | A61M 39/1011 604/191 |
| 2003/0106873 A1 * | 6/2003 | Grillo | B65D 23/06 215/41 |
| 2004/0024361 A1 * | 2/2004 | Fago | A61M 5/31525 604/152 |
| 2005/0251096 A1 | 11/2005 | Armstrong et al. | |
| 2006/0069347 A1 * | 3/2006 | Besing | A61M 5/3243 604/110 |
| 2007/0189924 A1 | 8/2007 | Knight | |
| 2007/0236884 A1 * | 10/2007 | Xia | H01L 23/427 257/E23.088 |
| 2012/0209111 A1 * | 8/2012 | Cowan | A61M 5/31 600/432 |
| 2013/0012908 A1 * | 1/2013 | Yeung | A61J 1/2096 604/404 |
| 2014/0066894 A1 | 3/2014 | Pearce et al. | |

FOREIGN PATENT DOCUMENTS

| | | |
|---|---|---|
| WO | 2011011396 A1 | 1/2011 |
| WO | 2014016579 A1 | 1/2014 |
| WO | 2015164783 A1 | 10/2015 |

OTHER PUBLICATIONS

"Extended European Search Report from EP Application No. 15806991", dated Mar. 14, 2018.
"International Preliminary Report on Patentability from PCT Application No. PCT/US2015/034687", dated Dec. 22, 2016.
"International Search Report and Written Opinion from PCT Application No. PCT/US2016/063449", dated Feb. 17, 2017.
Kralchevsky P.A. and Nagayama, K., "Capillary Bridges and Capillary-Bridge Forces (Chapter 11)", Particles at Fluid Interfaces and Membranes, 2001, 469-502.

* cited by examiner

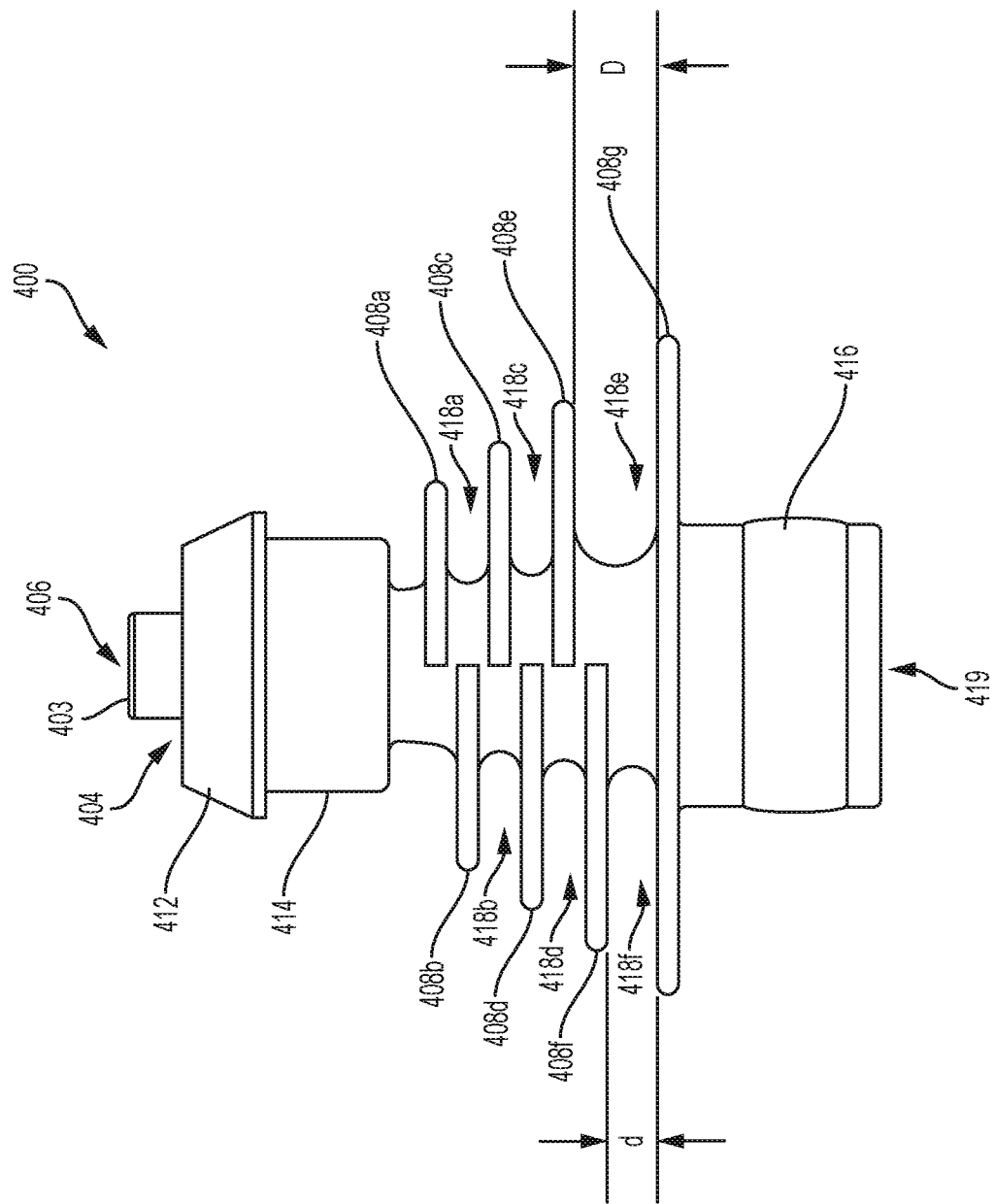

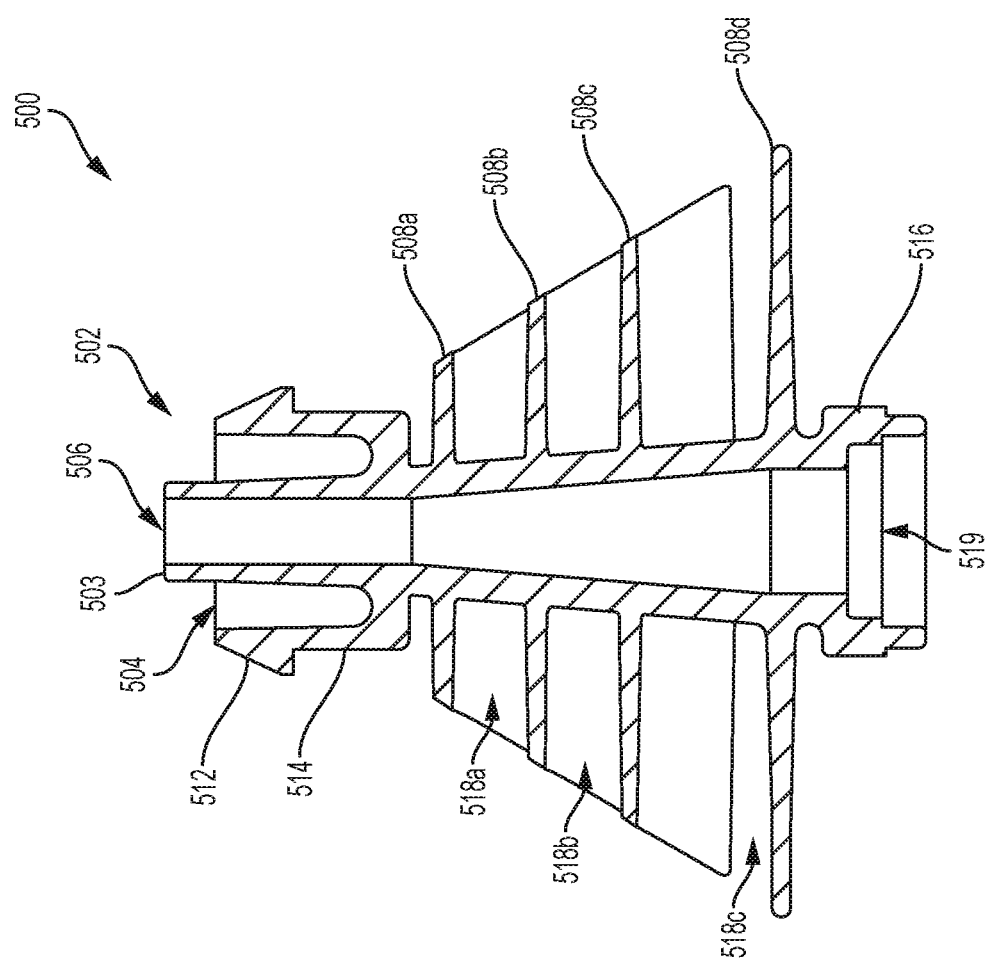

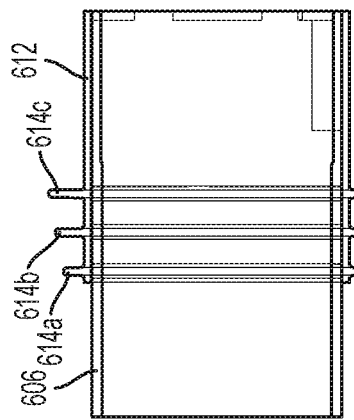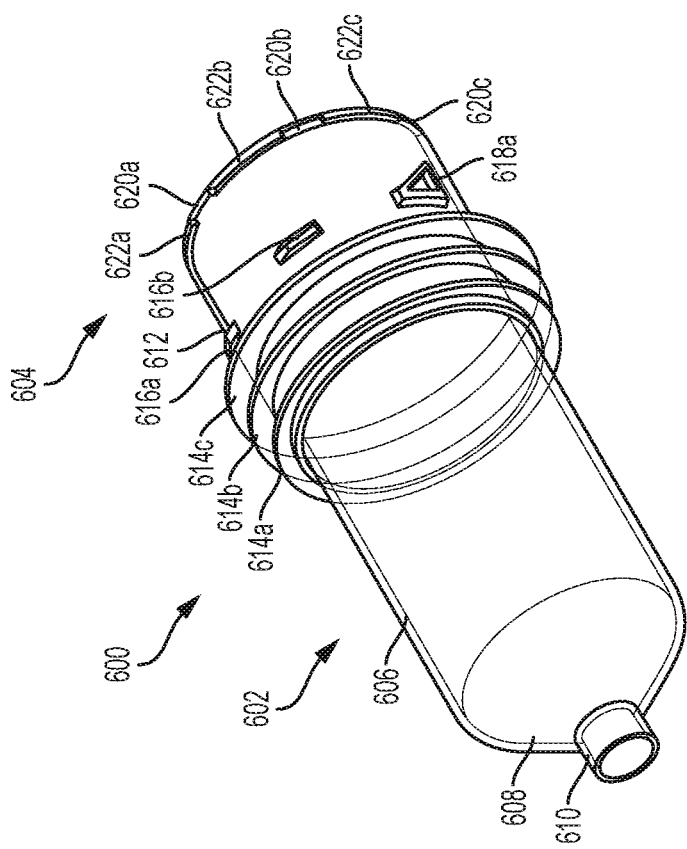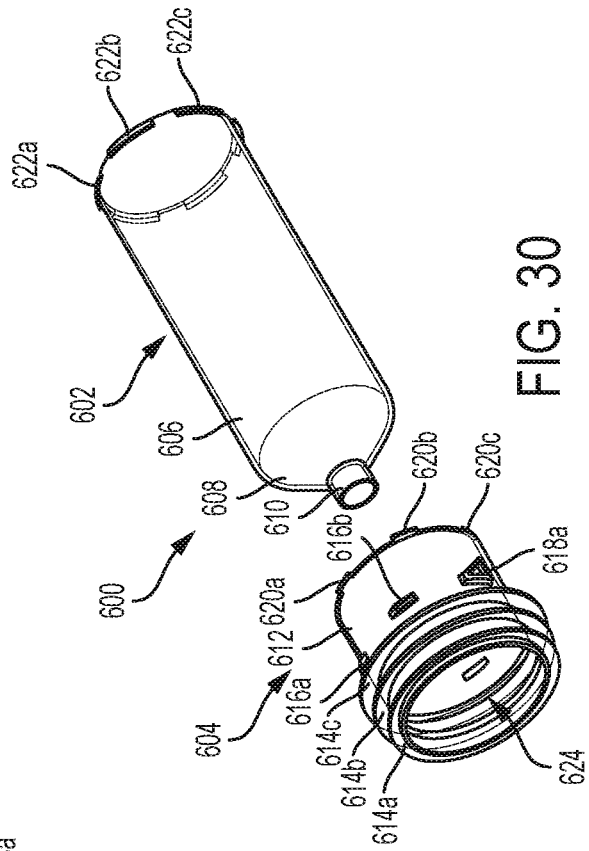

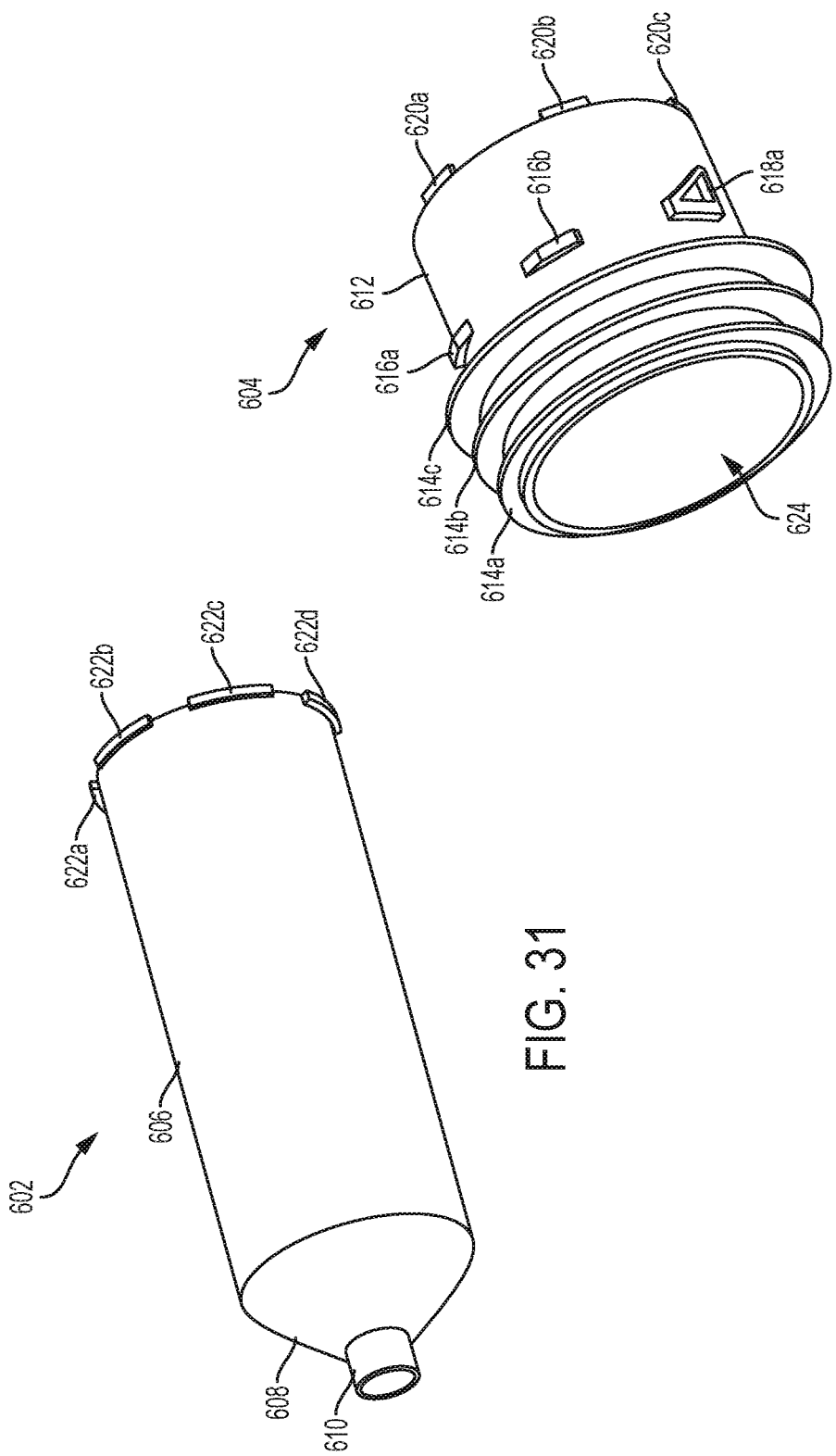

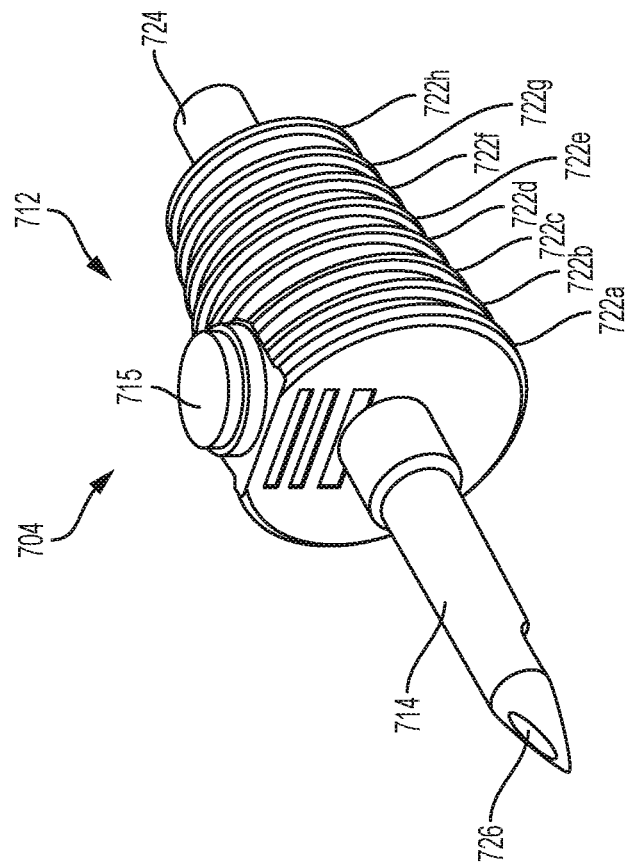
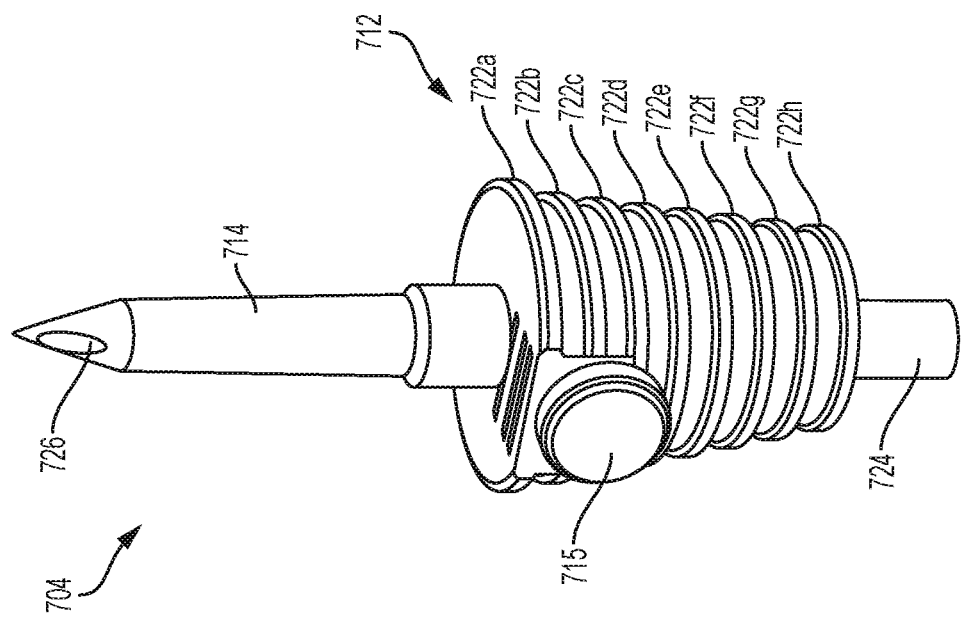

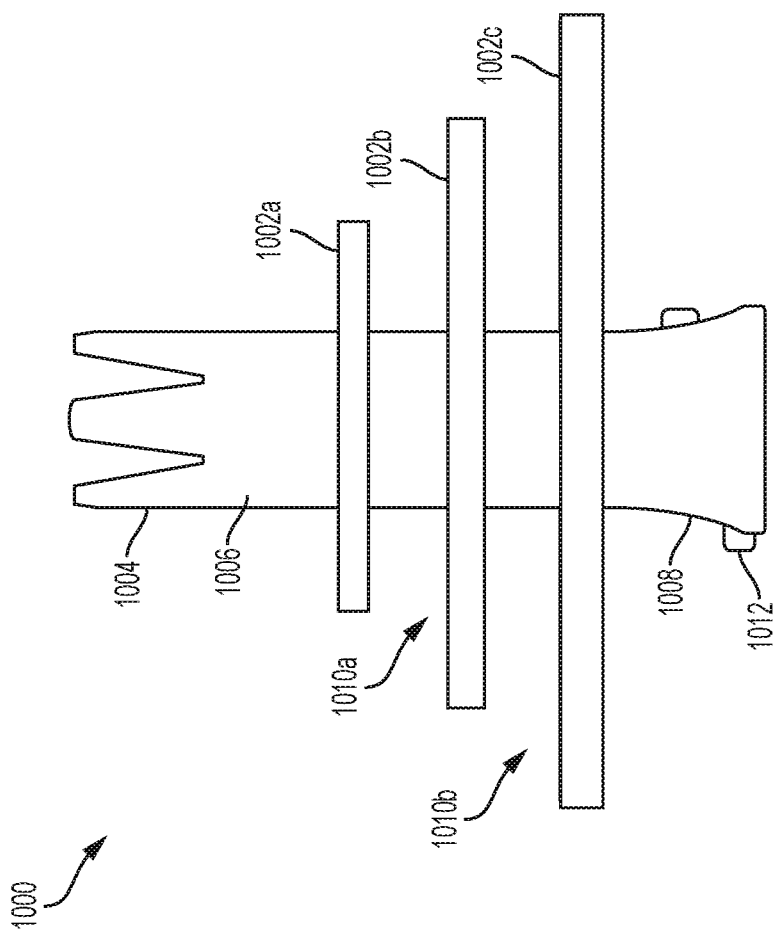

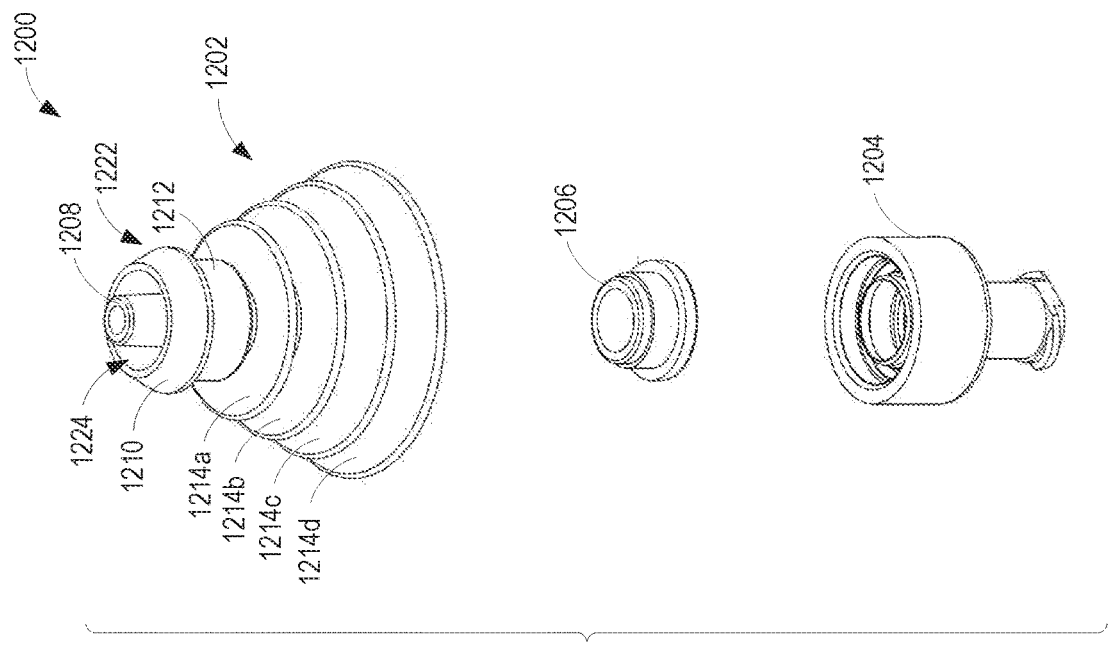
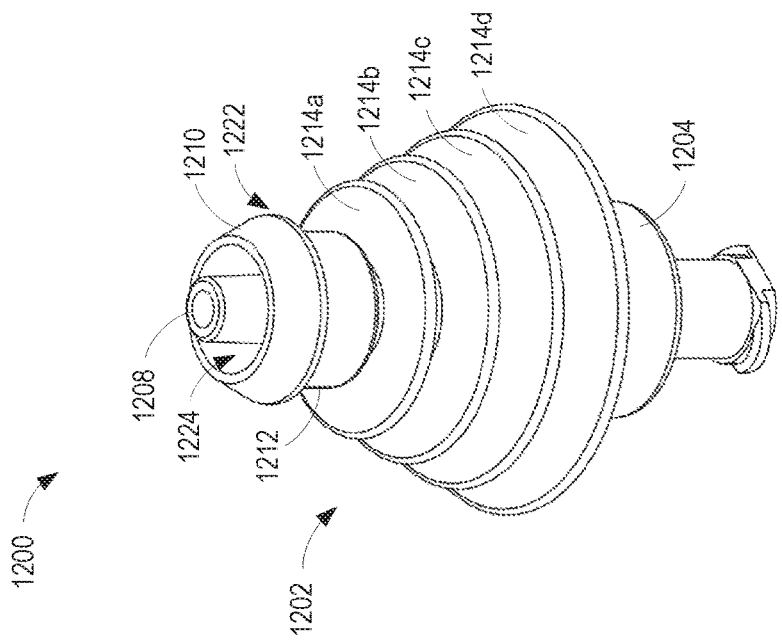

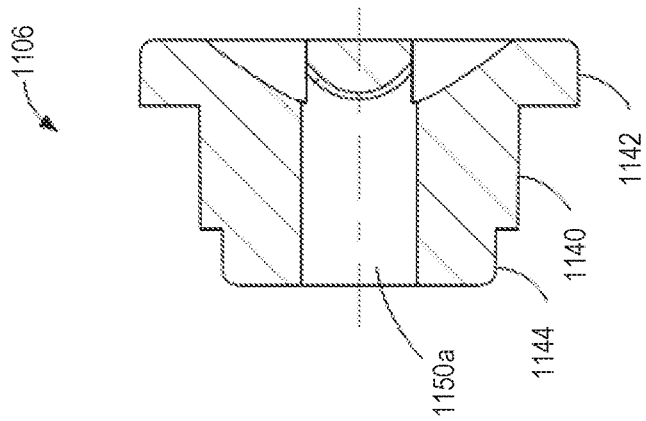
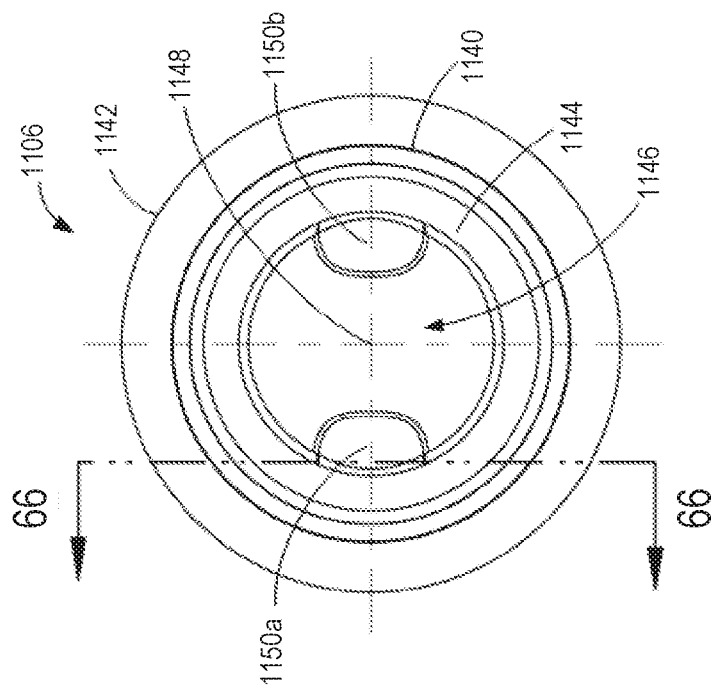
FIG. 66
FIG. 65

SYRINGE TIP WITH FLUID WICKING DRIP FLANGES

CROSS REFERENCE TO RELATED APPLICATIONS

This application is a 371 national phase application of PCT International Application No. PCT/US2016/063449, filed Nov. 23, 2016, and claims the benefit of U.S. Provisional Patent Application No. 62/259,708 titled SYRINGE TIP WITH FLUID WICKING DRIP FLANGES, filed Nov. 25, 2015, the disclosures of which are incorporated herein by reference in their entirety.

BACKGROUND

The present disclosure is related generally to a fluid wicking tip comprising a plurality of drip flanges arranged in a manner to facilitate wicking fluid in a space defined between the drip flanges by capillary action. More particularly, the present disclosure is related generally to a fluid wicking tip comprising a plurality of tiered drip flanges arranged in a manner to facilitate wicking fluid in a space defined between the drip flanges by capillary action. More particularly, the present disclosure is related generally to a syringe tip with a fluid wicking tip.

Syringe injection systems are among the medical devices that have been packaged for Single-Patient Single Use Disposables (SP-SUDs) use. Such syringe injection systems have been in use in medical procedures for many years. Many such syringes are operated manually by advancing a plunger extension in operative connection with an internal plunger to pressurize the fluid within the syringe. In numerous medical injection procedures, however, accurate control and/or high pressures may be employed that cannot be achieved via manual syringe operation. A number of syringes and powered injectors for use therewith have, therefore, been developed for use in medical procedures such as angiography, computed tomography (CT) and nuclear magnetic resonance (NMR)/magnetic resonance imaging (MRI). For example, U.S. Pat. No. 5,383,858 discloses a front-loading syringe and powered injector in both pressure jacket and jacketless configurations, the disclosure of which is incorporated herein by reference.

To load syringes with contrast fluid, a user typically connects a fill tube to the front nozzle or discharge outlet of the syringe and places the other end of the tube in a bottle or bag of contrast medium or other fluid. The plunger of the syringe is retracted (usually by means of the injector piston) to aspirate the contrast into the syringe until the desired amount is loaded into the syringe. After the syringe is filled, the fill tube is typically discarded. Often, contrast or other fluid contained in the fill tube may drip therefrom onto the floor or injector.

After the syringe is filled with fluid, a connector tube is connected to the discharge outlet of the syringe and the connecting tube is primed (typically by advancing the plunger in the syringe) to eject air from the syringe and the connector tube (i.e., to prevent air from being injected into the patient). While this technique may be effective in purging air from the tubing connected to the syringe, it is undesirable to have fluids dispensed from the end of the tube. Often, the fluids dispensed from the end of the tube foul the exterior surface of the tubing, syringe, and/or injector, drip, or leak from the various connections and fall onto the floor. When dealing with contrast media, this is particularly undesirable because the media is very sticky and has a tendency to migrate to whatever surface the operator touches after purging the tube.

Furthermore, in some applications a direct vented spike is positioned on top of a syringe. The vented spike is use to pierce a bottle of contrast fluid or saline fluid to be delivered to the patient. In such applications, when the bottle and the spike is removed from the syringe, the fluid remaining in the spike can drip out onto the syringe tip.

In some injector systems, the contrast or saline bottles are positively pressurized after filling. Thus, using a direct vented spike on top of the syringe to pierce the bottle may cause fluid to spill. In such applications, if the user removes the bottle from the spike before unthreading the spike from the syringe, the positive pressure causes the fluid to spray out and drip onto the syringe.

The present disclosure provides a syringe tip with drip flanges arranged in a manner to facilitate wicking excess fluid between the drip flanges by capillary action.

SUMMARY

In one aspect, a fluid wicking is provided according to the following examples.

Example 1

A fluid wicking tip, comprising a plurality of drip flanges arranged to wick fluid between narrow spaces defined between any two drip flanges. The narrow spaces are dimensioned to facilitate wicking by capillary action.

Example 2

The fluid wicking tip of example 1, wherein the drip flanges are arranged in at least two tiers.

Example 3

The fluid wicking tip of example claim 2, wherein the at least two tiers have a different diameter.

Example 4

The fluid wicking tip of example 3, wherein a top tier drip flange has a smaller diameter than a lower tier drip flange.

Example 5

The fluid wicking tip of example 3, wherein a top tier drip flange has a larger diameter than a lower tier drip flange.

Example 6

The fluid wicking tip of example 2, wherein a top tier drip flange has the same diameter as a lower tier drip flange.

Example 7

The fluid wicking tip of any combination of examples 1 to 6, further comprising a drip cup positioned above the plurality of drip flanges.

Example 8

The fluid wicking tip of any combination of examples 1 to 6, further comprising a drip cup positioned below the plurality of drip flanges.

Example 9

The fluid wicking tip of any combination of examples 1 to 8, wherein the plurality of drip flanges are flat and smooth and continuous.

Example 10

The fluid wicking tip of any combination of examples 1 to 9, wherein the plurality of drip flanges are staggered relative to each other.

Example 11

The fluid wicking tip of any combination of examples 1 to 10, wherein the plurality of drip flanges are ruffled.

Example 12

The fluid wicking tip of any combination of examples 1 to 11, further comprising a piercing tip fluidly coupled thereto.

Example 13

The fluid wicking tip of any combination of examples 1 to 12, wherein the plurality of drip flanges each comprises an opening to facilitate draining fluid from a drip flange located above a lower drip flange.

Example 14

The fluid wicking tip of any combination of examples 1 to 13, further comprising a luer fitting sized and configured to fluidly couple to a syringe.

Example 15

The fluid wicking tip of any combination of examples 1 to 14, further comprising a luer fitting sized and configured to fluidly couple to a flexible tube assembly.

In another aspect, a syringe is provided according to the following examples.

Example 16

A syringe, comprising a body defining a cylindrical fluid chamber, a tapered portion extending from the cylindrical fluid chamber, and a tip extending from the tapered portion; and fluid wicking tip fluidly coupled to the tip of the syringe.

Example 17

The syringe of example 16, further comprising a piercing tip fluidly coupled to the fluid wicking tip.

Example 18

The syringe of any combination of examples 16 and 17, wherein the fluid wicking tip is integrally formed with the tapered portion of the body.

In another aspect, a modular syringe system is provided according to the following examples.

Example 19

A modular syringe system, comprising a syringe comprising a body defining a cylindrical fluid chamber, a tapered portion extending from the cylindrical fluid chamber, and a tip extending from the tapered portion; and a sleeve configured to be slidably disposed over the cylindrical portion of the body and fit in rotational locking arrangement with the cylindrical portion of the body.

Example 20

The modular syringe system of example 19, wherein the sleeve further comprises a plurality of drip flanges disposed about an outer circumference of the sleeve.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

The foregoing summary is illustrative only and is not intended to be in any way limiting. In addition to the illustrative aspects and features described above, further aspects and features will become apparent by reference to the drawings and the following detailed description.

BRIEF DESCRIPTION OF THE DRAWINGS

The novel features described herein are set forth with particularity in the appended claims. Such features, however, both as to organization and methods of operation may be better understood by reference to the following description, taken in conjunction with the accompanying drawings as follows.

FIG. 22 is a side view of the fluid wicking tip comprising a plurality of staggered tiered drip flanges shown in FIG. 20, according to one aspect of the present disclosure.

FIG. 27 is a sectional view of the fluid wicking tip comprising a plurality of ruffled tiered flanges shown in FIG. 26, according to one aspect of the present disclosure.

FIG. 28 is a perspective view of a sleeved modular syringe system comprising one aspect of a syringe and one aspect of a sleeve slidably disposed over the syringe, according to one aspect of the present disclosure.

FIG. 29 is a partial sectional view of the sleeved modular syringe system, according to one aspect of the present disclosure.

FIG. 30 is an exploded view of the sleeved modular syringe system with the sleeve shown separated from the syringe, according to one aspect of the present disclosure.

FIG. 31 is a perspective view of the syringe, according to one aspect of the present disclosure.

FIG. 32 is a perspective view of the sleeve, according to one aspect of the present disclosure.

FIG. 37 is a perspective view of the spike tip comprising a plurality of tiered drip flanges shown in FIG. 35, according to one aspect of the present disclosure.

FIG. 38 is a perspective view of the spike tip comprising a plurality of tiered drip flanges shown in FIG. 35, according to one aspect of the present disclosure.

FIG. 41 illustrates a fluid wicking tip comprising a plurality of tiered drip flanges arranged to facilitate wicking fluid by capillary action, according to an aspect of the present disclosure.

FIG. 47 is a perspective view of a fluid wicking tip assembly comprising a fluid wicking tip.

FIG. 48 is an exploded view of the fluid wicking assembly shown in FIG. 47, according to one aspect of the present disclosure.

FIG. 65 is a top view of the diverter component shown in FIG. 63, according to one aspect of the present disclosure.

FIG. 66 is a sectional view of the diverter component shown in FIG. 63 taken along section line 66-66 shown in FIG. 65, according to an aspect of the present disclosure.

FIG. 74 is the first frame of the sequence illustrating pipette 1302 filled with a fluid 1304 to be dropped on the fluid wicking tip, according to an aspect of the present disclosure;

FIG. 75 is the second frame of the sequence after several drops of fluid have been dropped onto the fluid wicking tip, according to one aspect of the present disclosure;

FIG. 76 is the third frame of the sequence after additional drops of fluid have been dropped onto the fluid wicking tip, according to one aspect of the present disclosure;

FIG. 77 is the fourth frame in the sequence after additional drops of fluids have been dropped onto the fluid wicking tip, according to one aspect of the present disclosure;

FIG. 78 is the fifth frame of the sequence after additional drops of fluid have been dropped onto the fluid wicking tip, according to one aspect of the present disclosure; and FIG. 79 is the sixth frame of the sequence after additional drops of fluid have been dropped onto the fluid wicking tip, according to one aspect of the present disclosure.

DETAILED DESCRIPTION

Figure 1:
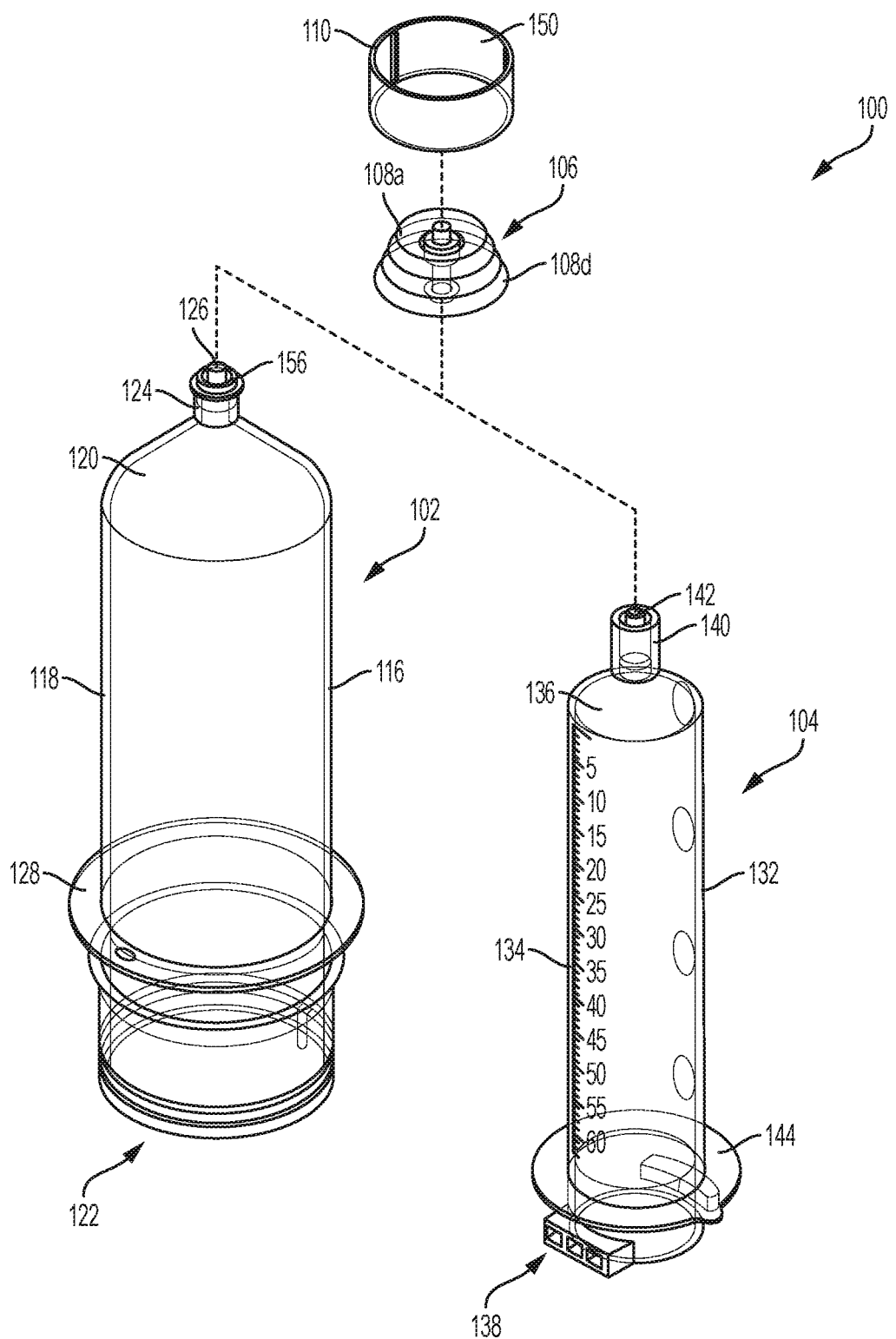
FIG. 1 is a perspective view of a syringe set comprising first and second syringes, a fluid wicking tip, and a drip cup, according to one aspect of the present disclosure.

In the following detailed description, reference is made to the accompanying drawings, which form a part hereof. In the drawings, similar symbols and reference characters typically identify similar components throughout the several views, unless context dictates otherwise. The illustrative features described in the detailed description, drawings, and claims are not meant to be limiting. Other features may be utilized, and other changes may be made, without departing from the scope of the subject matter presented here.

Before explaining the various aspects of the fluid wicking tip assembly in detail, it should be noted that the various aspects disclosed herein are not limited in their application or use to the details of construction and arrangement of parts illustrated in the accompanying drawings and description. Rather, the disclosed devices may be positioned or incorporated in other devices, variations and modifications thereof, and may be practiced or carried out in various ways. Accordingly, aspects of the fluid wicking tip assembly disclosed herein are illustrative in nature and are not meant to limit the scope or application thereof. Furthermore, unless otherwise indicated, the terms and expressions employed herein have been chosen for the purpose of describing the various aspects of the fluid wicking tip assembly for the convenience of the reader and are not to limit the scope thereof. In addition, it should be understood that any one or more of the components of the fluid wicking tip assembly, expressions thereof, and/or examples thereof, can be combined with any one or more of the other components, expressions thereof, and/or examples thereof, without limitation.

Also, in the following description, it is to be understood that terms such as front, back, inside, outside, top, bottom and the like are words of convenience and are not to be construed as limiting terms. As used herein, the term "proximal" when used to describe a portion of a syringe is generally used to indicate the portion of the syringe closer to the injector and the term "distal" when used to describe a portion of a syringe is generally used to indicate the portion of the syringe closer to the patient. Terminology used herein is not meant to be limiting insofar as devices described herein, or portions thereof, may be attached or utilized in other orientations. The various aspects of the fluid wicking tip assembly will be described in more detail with reference to the drawings.

FIG. 1 is a perspective view of a fluid dispensing system 100 comprising first and second syringes 102, 104, a fluid wicking tip 106, and a drip cup 110, according to one aspect of the present disclosure. The fluid wicking tip 106 comprises tiered drip flanges 108 arranged to facilitate wicking fluid by capillary action in a narrow circumferential space defined between any two tiers of the tiered drip flanges 108 and retaining the fluid between the tiered drip flanges 108 by the surface tension formed between the tiered drip flanges 108. Thus, both capillary and surface tension forces can be exploited to prevent dripping. The fluid wicking tip 106 and/or the drip cup 110 are configured to attach to distal tips 124, 140 at the fluid transfer ends 112, 114 of the syringes 102, 104. The tiered drip flanges 108 are flat plates or planes that are stacked in a spaced apart relationship to define a space therebetween. The gap or distance between the flat plates is selected such that fluid introduced in the space defined between the plates forms a capillary bridge or fluid bridge. As described with particularity herein, a fluid bridge is formed between two solid surfaces (e.g., flanges, planes, flat plates). The fluid bridge can lead to the appearance of attractive (adhesive) force between the two solid surfaces owing to the decreased pressure inside the fluid bridge and the direct action of the surface tension force exerted around the annulus of the meniscus.

For conciseness and clarity of illustration FIG. 1 depicts a fluid wicking tip 106 and a drip cup 110, however, it will be appreciated that each of the first and second syringes 102, 104 can be furnished with a fluid wicking tip 106 and/or a drip cup 110. The fluid wicking tip 106 comprises a plurality of tiered drip flanges 108 spaced apart by a distance that facilitates wicking fluid between drip flanges by capillary action. The drip cup 110 is configured to surround the base tiered drip flange 108d of the fluid wicking tip 106. The drip cup 110 collects fluid accumulated in the narrow circumferential spaces defined between the tiered drip flanges 108 of the fluid wicking tip 106 by the Coanda effect, for example, which is the tendency of a fluid jet to be attracted to a nearby surface. In this instance, the nearby surface is an interior surface 150 of the drip cup 110.

The first syringe 102 comprises a housing 116 (tube, barrel), that includes a cylindrical body 118, a conical portion 120 at a distal end, an injector interface 122 at a proximal end, and terminates in a distal tip 124 defining an orifice 126 for transferring fluids into and out of the first syringe 102 at a fluid delivery end of the housing 116. The distal tip 124 includes a threaded luer fitting or other suitable fitting configured to engage the fluid wicking tip 106 and/or the drip cup 110. The fluid wicking tip 106 and/or the drip cup 110 can be configured to fluidly couple to a corresponding fitting on a flexible tube assembly used to deliver the fluid to a patient. The first syringe 102 also comprises a drip flange 128 about the outer circumference of the housing 116.

The second syringe 104 comprises a housing 132 (tube, barrel) that includes a cylindrical body 134, a conical portion 136 at a distal end, an injector interface 138 at a proximal end, and terminates in a distal tip 140 defining an orifice 142 for transferring fluids into and out of the syringe 104 at a fluid delivery end of the housing 132. The distal tip 140 includes a threaded luer fitting or other suitable fitting configured to engage the fluid wicking tip 106 and/or the drip cup 110. The fluid wicking tip 106 and/or the drip cup 110 can be configured to fluidly couple to a corresponding fitting of a tube assembly used to deliver the fluid to a patient. The second syringe 104 also comprises a drip flange 144 about the outer circumference of the housing 132.

Although the housings 116, 132 of the first and second syringes 102, 104 are generally cylindrical, in other aspects of the present disclosure, the housings 116, 132 may be tapered. Furthermore, although the shape of the housings 116, 132 are shown to be circular, other geometric configurations are contemplated to be within the scope of the present disclosure. Such geometric configurations include oval, square, rectangular, or other polygonal configurations.

Once the first and second syringes 102, 104 are inserted into respective ports of an injector, the first and second syringes 102, 104 can be connected by a flexible tube assembly and filled with suitable fluids from fluid connector assemblies connected to respective containers of medical fluid. For example, in one aspect, the first syringe 102 may be filled with a saline fluid and the second syringe 104 may be filled with a contrast fluid, such as a contrast imaging agent suitable for a CT, MRI, PET or other suitable medical imaging process. The injector is configured to inject or dispense the fluid medium contained in the first and second syringes 102, 104 in a controlled manner as may be employed by medical procedures such as angiography, CT, PET, and NMR/MRI. For example, U.S. Pat. No. 5,383,858 discloses a front-loading syringe and powered injector in pressure jacket and jacketless examples, which disclosure is incorporated by this reference.

Figure 2:
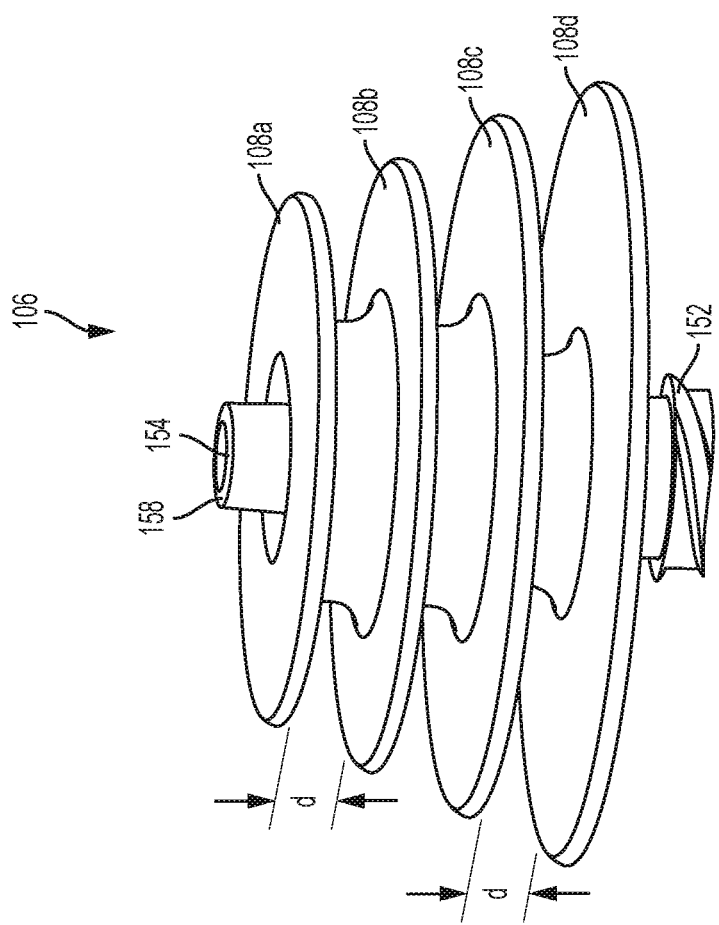
FIG. 2 is perspective view of a fluid wicking tip comprising a plurality of tiered drip flanges for coupling to a tip of a syringe, according to an aspect of the present disclosure.
Figure 4:
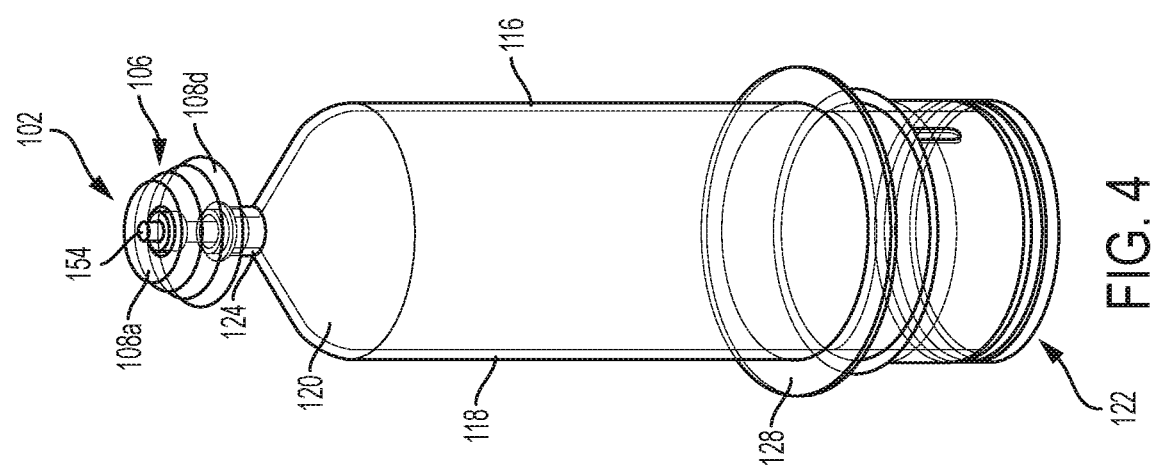
FIG. 4 illustrates a first syringe fluidly coupled to a fluid wicking tip, according to one aspect of the present disclosure.

FIG. 2 is perspective view of a fluid wicking tip 106 comprising tiered drip flanges and configured to couple to a tip of a syringe, according to one aspect of the present disclosure. The fluid wicking tip 106 comprises a plurality of tiered drip flanges 108a, 108b, 108c, 108d spaced apart by a distance "d", also referred to as gap width, that facilitates wicking fluid between the tiered drip flanges 108a-108d by capillary action. Suitable values for the gap width "d", which defines the spacing between the drip flanges 108a-108d, or solid planes, is discussed in connection with FIGS. 12 to 15. The fluid wicking tip 106 is adapted to fluidly couple to the distal tip 124 of the first syringe 102 as shown in FIG. 4, which illustrates the first syringe 102 fluidly coupled to the fluid wicking tip 106, according to one aspect of the present disclosure. The fluid wicking tip 106 is fluidly coupled to the distal tip 124 of the first syringe 102 by way of a threaded luer coupling 162 or by any other suitable coupling arrangement. As shown in the sectional view of FIG. 6, a distal portion of the first syringe 102 is fluidly coupled to the fluid wicking tip 106, according to one aspect of the present disclosure. The fluid wicking tip 106 is threadably engaged with a threaded luer fitting 156 provided at the distal tip 124 of the first syringe 102. The fluid wicking tip 106 also defines an orifice 154 for transferring fluids into and out of the first syringe 102. As shown more clearly in the section view of FIG. 6, the fluid wicking tip 106 also comprises a threaded luer fitting 158 configured to fluidly couple the first syringe 102 to a corresponding fitting of a flexible tube assembly used to deliver the fluid to a patient.

Although in the example of FIG. 2, the tiered drip flanges 108a-108d are flat, in one aspect the tiered drip flanges 108a-108d may be arranged in a winged configuration where the drip flanges are angled with respect to a vertical axis but still substantially parallel relative to each other. In yet another aspect, the tiered drip flanges 108a-108d may be arranged in a winged configuration where the drip flanges are angled with respect to a vertical axis and are not parallel relative to each other.

Figure 3:
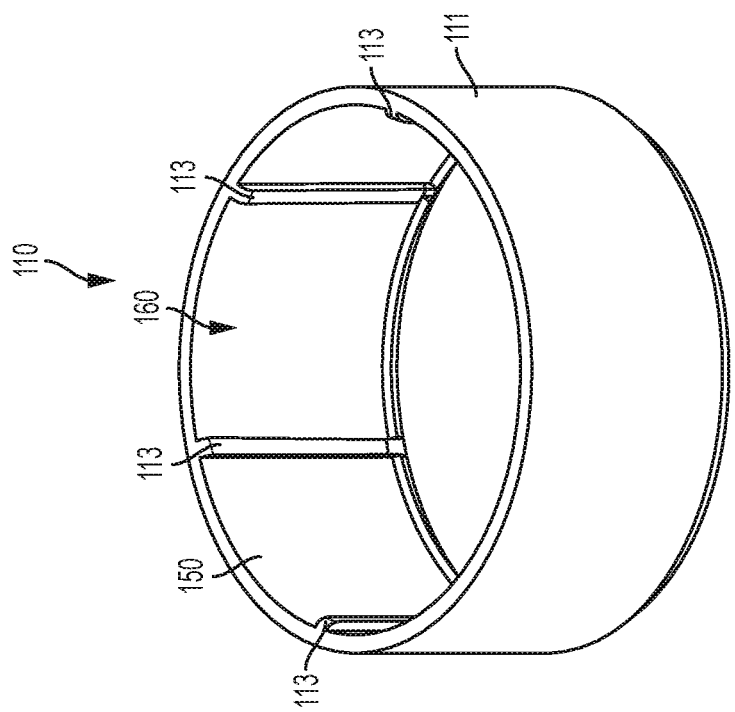
FIG. 3 is a perspective view of a drip cup, according to an aspect herein.
Figure 5:
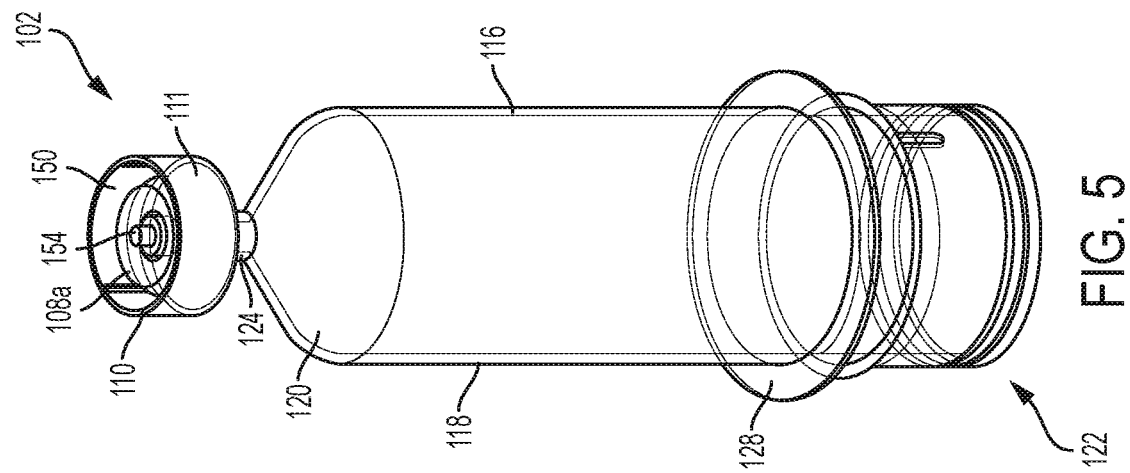
FIG. 5 illustrates a drip cup fluidly coupled to the fluid wicking tip shown in FIG. 4, according to one aspect of the present disclosure.

FIG. 3 is a perspective view of a drip cup 110, according to one aspect of the present disclosure. With reference to FIGS. 2 and 3, the drip cup 110 comprises a cylindrical housing 111 and is configured to surround the base drip flange 108d of the fluid wicking tip 106. The drip cup 110 collects fluid accumulated between the tiered drip flanges 108 of the fluid wicking tip 106. In this instance, the nearby surface is an interior surface 150 of the drip cup 110. As illustrated in FIG. 5, the drip cup 110 is fluidly coupled to the fluid wicking tip 106 shown in FIG. 4, according to one aspect of the present disclosure. As illustrated in the sectional view of FIG. 7, the drip cup 110 is fluidly coupled to the fluid wicking tip 106 shown in FIG. 6, according to one aspect of the present disclosure. The interior surface 150 of the drip cup 110 comprises several ribs 113 about the internal circumference. The ribs 113 contact the outer edges of the tiered drip flanges 108a-108d such that fluid is wicked between the narrow circumferential spaces defined by the tiered drip flanges 108a-108d without the assistance of, and in opposition to, external forces like gravity. The fluid contacts the ribs 113 causing the fluid to drain into an internal space 160 defined by the drip cup 110. Thus, excess fluid collected between tiered drip flanges 108a-108d is drained into drip cup 110.

Figure 7:
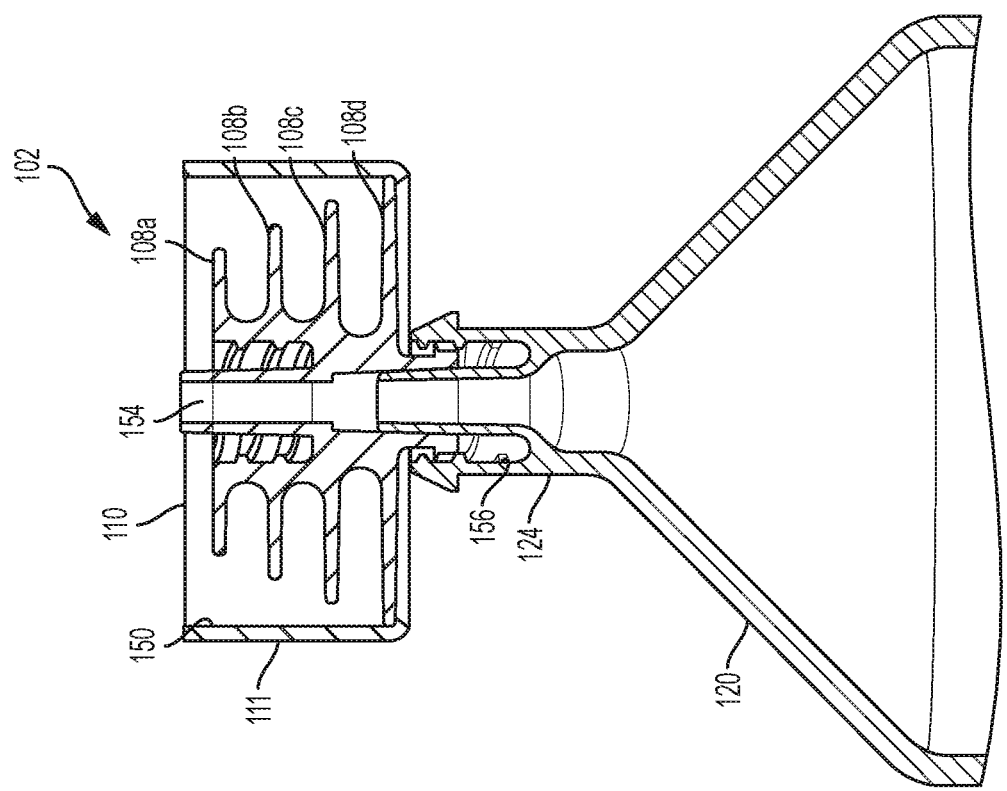
FIG. 7 is a sectional view of a drip cup fluidly coupled to the fluid wicking tip shown in FIG. 6, according to one aspect of the present disclosure.
Figure 9:
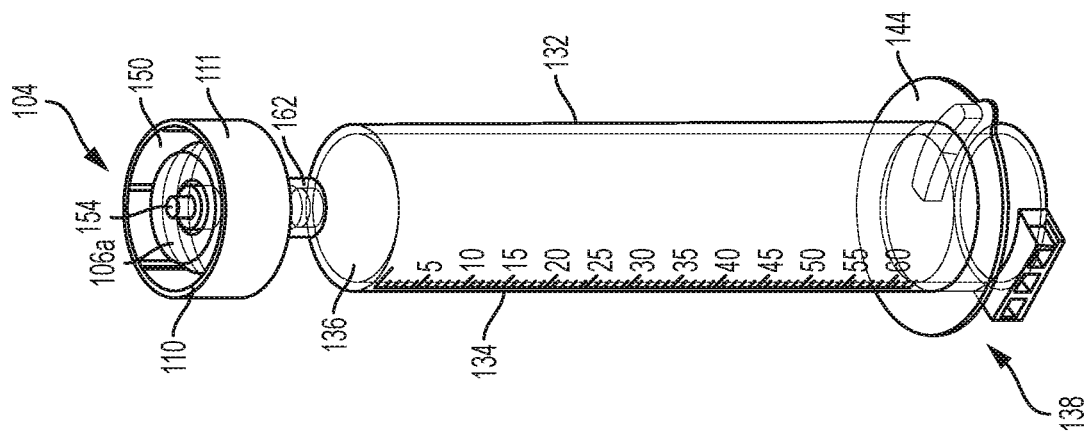
FIG. 9 illustrates a drip cup fluidly coupled to the fluid wicking tip shown in FIG. 8, according to one aspect of the present disclosure.
Figure 8:
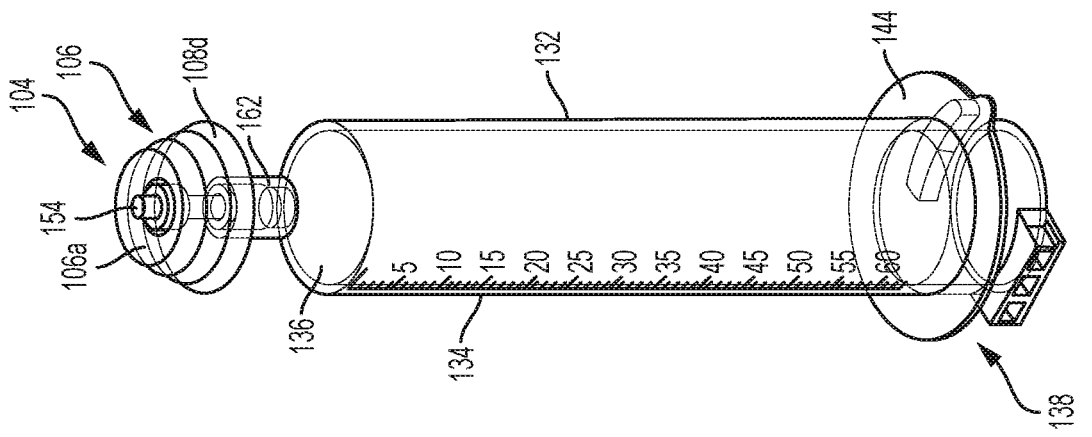
FIG. 8 illustrates a second syringe fluidly coupled to a fluid wicking tip, according to one aspect of the present disclosure.
Figure 11:
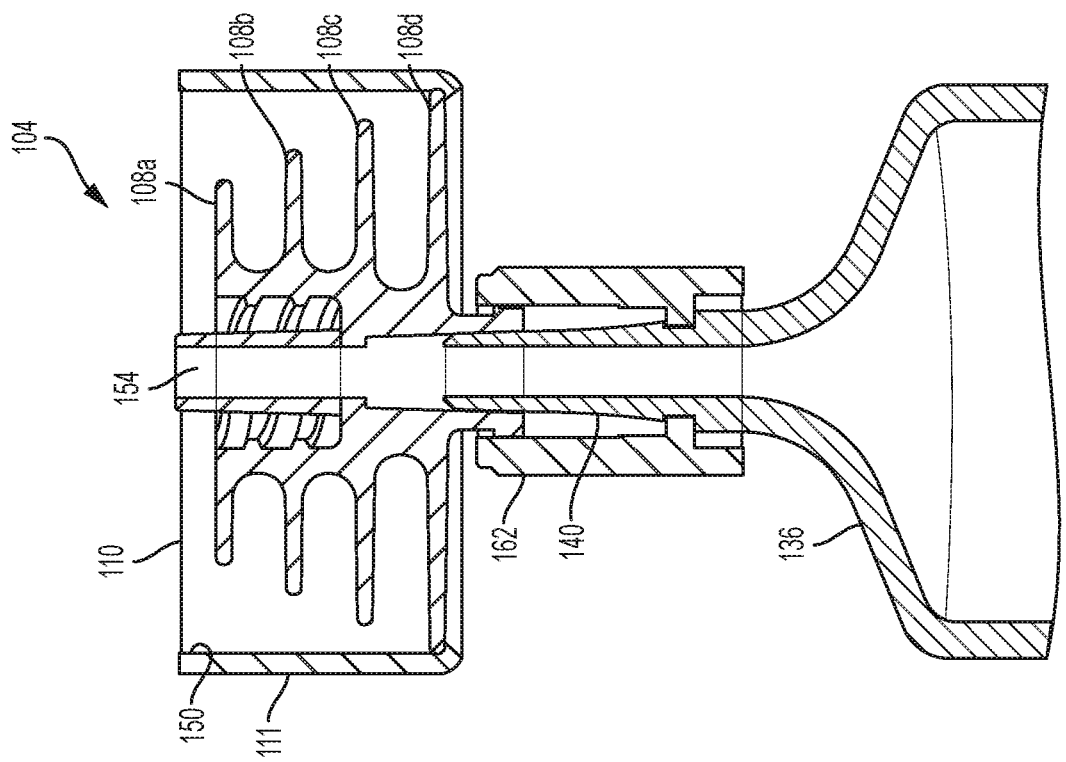
FIG. 11 is a sectional view of a drip cup fluidly coupled to the fluid wicking tip shown in FIG. 10, according to one aspect of the present disclosure.
Figure 10:
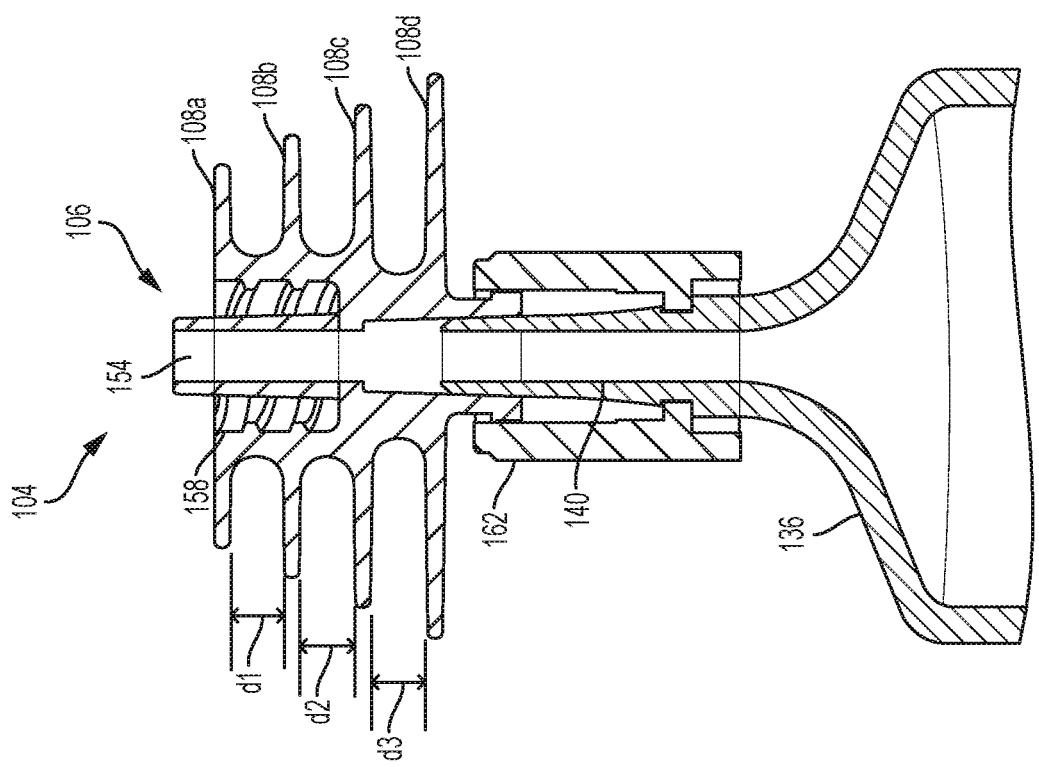
FIG. 10 is a sectional view of a distal portion of a second syringe fluidly coupled to a fluid wicking tip, according to one aspect of the present disclosure.

FIG. 8 illustrates a second syringe 104 fluidly coupled to a fluid wicking tip 106, according to one aspect of the present disclosure. FIG. 9 illustrates a drip cup 110 fluidly coupled to the fluid wicking tip 106 shown in FIG. 8, according to one aspect of the present disclosure. FIG. 10 is a sectional view of a distal portion of the second syringe 104 fluidly coupled to the fluid wicking tip 106, according to one aspect of the present disclosure. FIG. 11 is a sectional view of the drip cup 110 fluidly coupled to the fluid wicking tip 106 shown in FIG. 10, according to one aspect of the present disclosure. The fluid wicking tip 106 is adapted to fluidly couple to the distal tip 140 of the second syringe 104 as shown in FIG. 7, which illustrates the second syringe 104 fluidly coupled to the fluid wicking tip 106, according to one aspect of the present disclosure. The fluid wicking tip 106 is fluidly coupled to the distal tip 140 of the second syringe 104 by way of a threaded luer coupling 162, for example a threaded swivel nut. As shown in the sectional view of FIG. 10, a distal portion of the second syringe 104 is fluidly coupled to the fluid wicking tip 106, according to one aspect of the present disclosure. The fluid wicking tip 106 is threadably engaged with a threaded luer coupling 162 provided at the distal tip 140 of the second syringe 104. The fluid wicking tip 106 also defines an orifice 154 for transferring fluids into and out of the syringe 104. As shown more clearly in the section view of FIG. 10, the fluid wicking tip 106 also comprises a threaded luer fitting 158 configured to fluidly couple the second syringe 104 to a corresponding fitting of a flexible tube assembly used to deliver the fluid to a patient.

Figure 6:
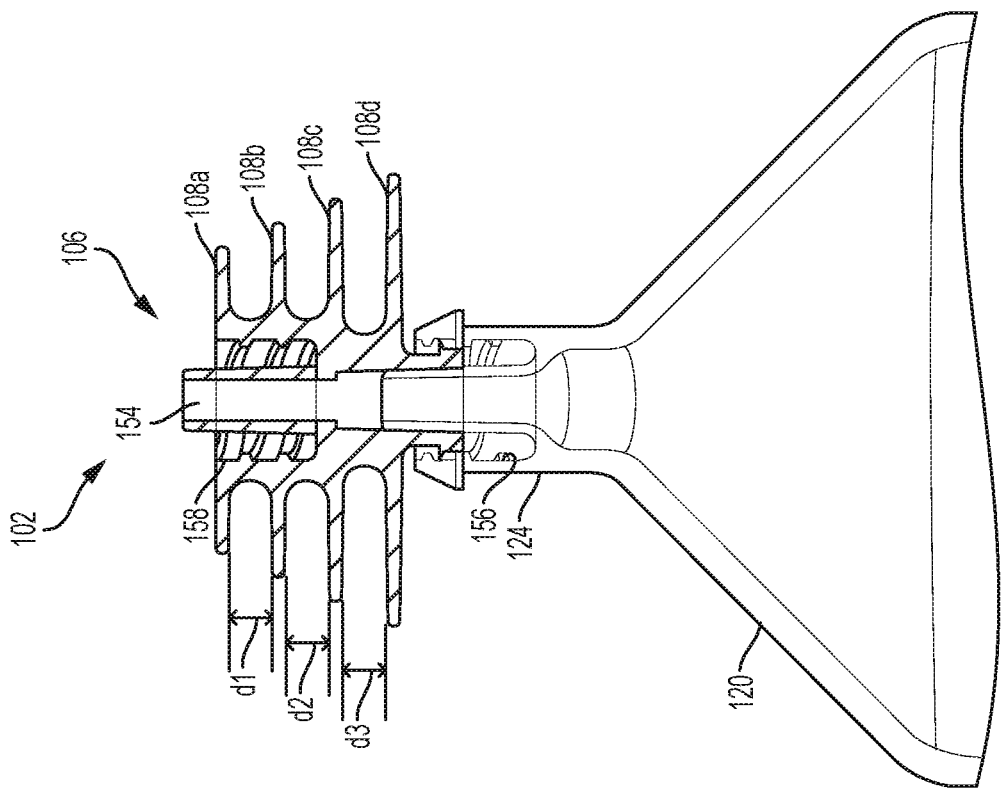
FIG. 6 is a sectional view of a distal portion of a first syringe fluidly coupled to a fluid wicking tip, according to one aspect of the present disclosure.

As shown in FIGS. 6 and 10, the gap width between the tiered drip flanges 108a-108d is referenced by d1, d2, d3, where is some aspects the gap width is constant such that d1=d2=d3 and in other aspects the gap width is variable such that d1≠d2≠d3. In regard to the latter aspects d1<d2<d3 or d1>d2>d3 or the gap width can be determined in some other manner, without limitation.

Figure 12:
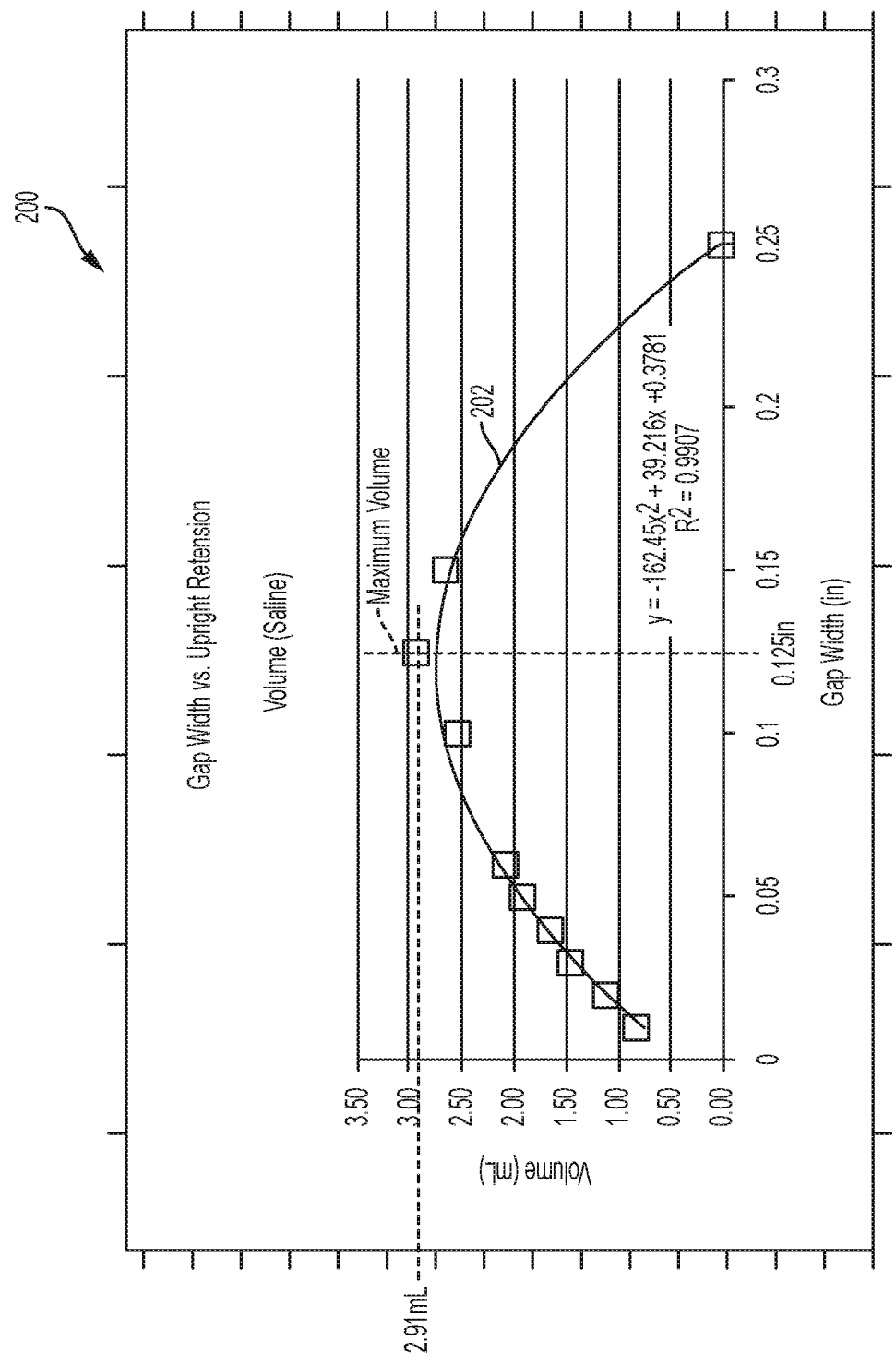
FIG. 12 is a graphical depiction of a curve representative of gap width "d" versus upright retention volume, according to one aspect of the present disclosure.
Figure 15:
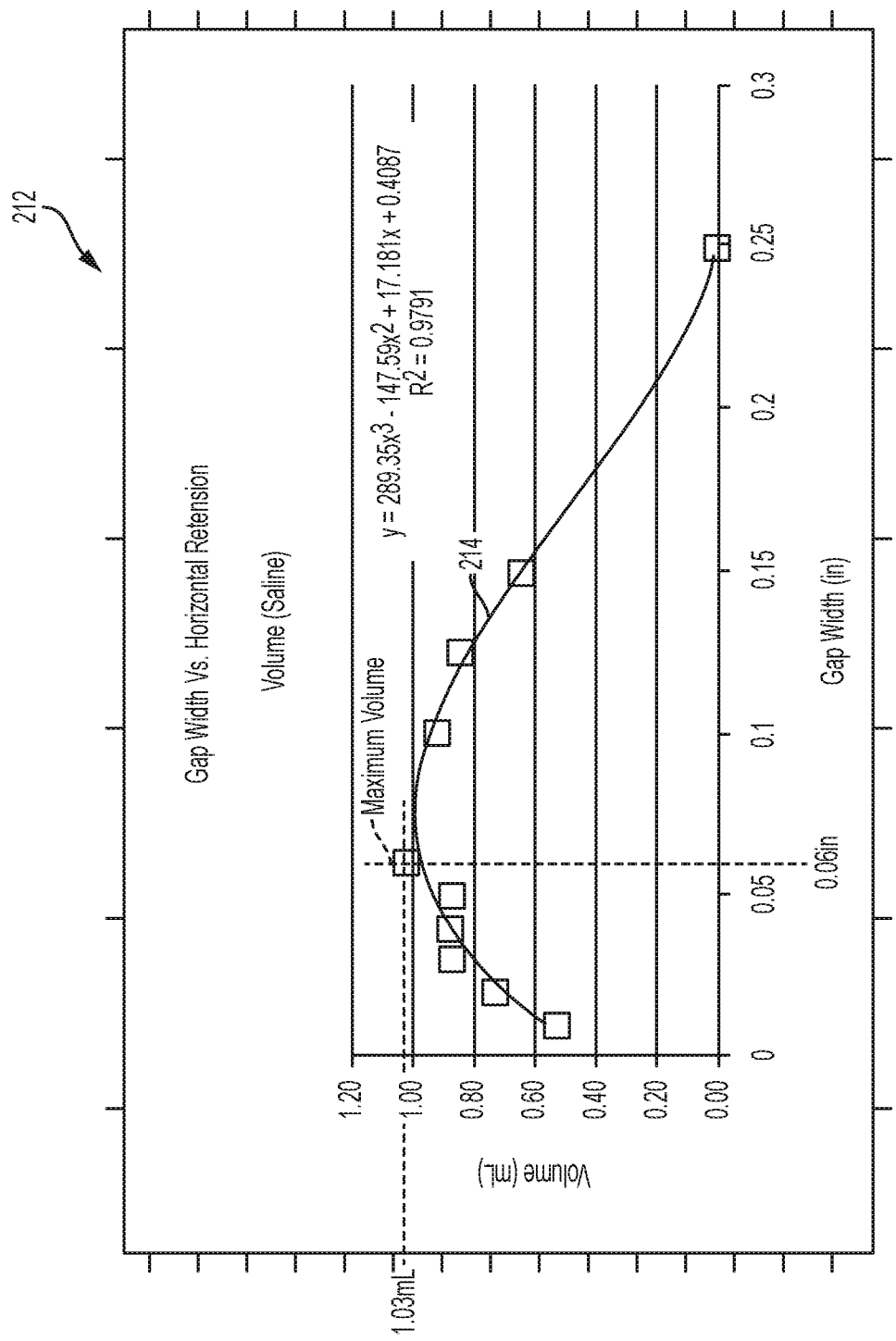
FIG. 15 is a graphical depiction of a curve representative of gap width "d" versus horizontal retention volume, according to one aspect of the present disclosure.
Figure 16:
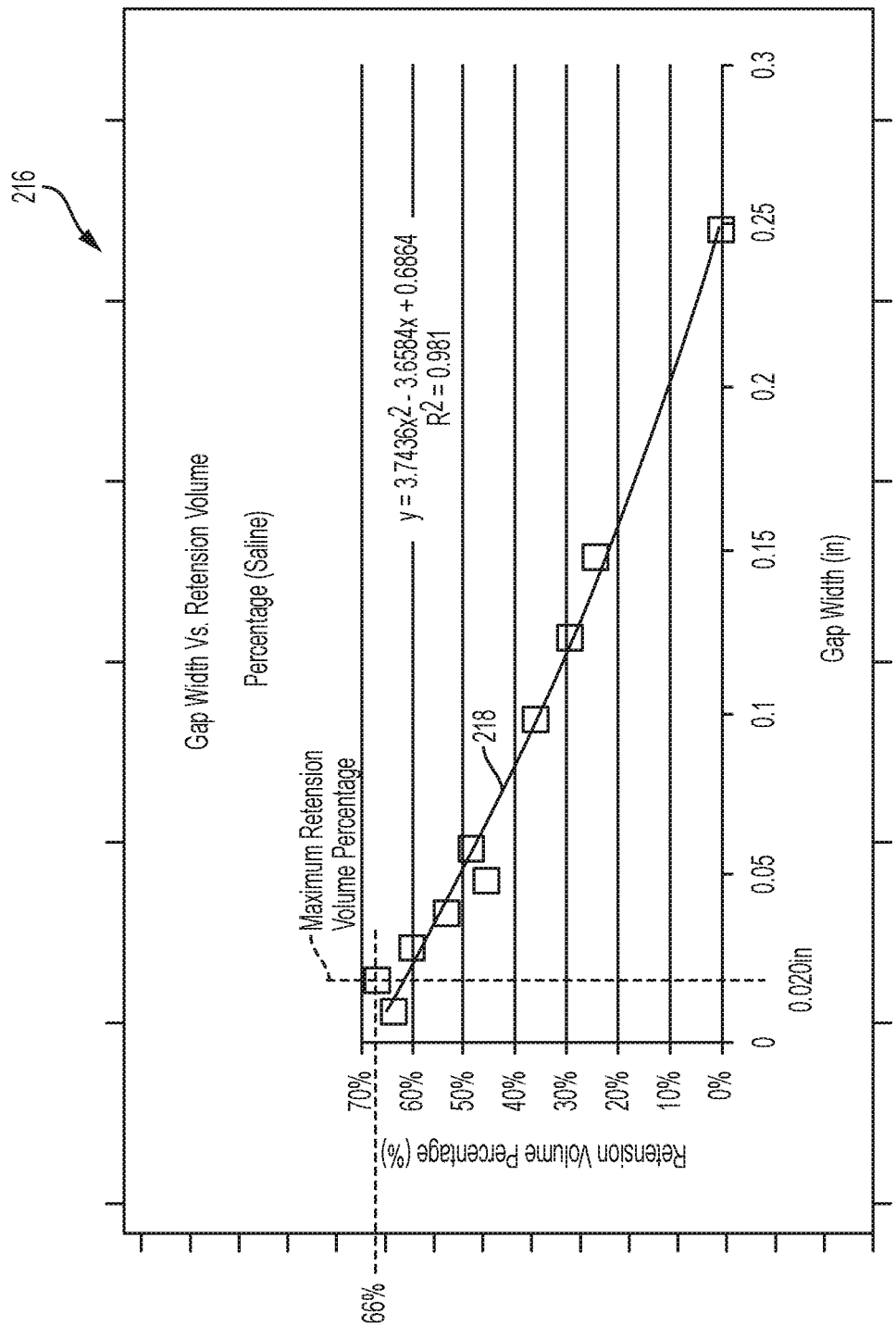
FIG. 16 is a graphical depiction of a curve representative of gap width "d" versus retention volume percentage, according to one aspect of the present disclosure.
Figure 17:
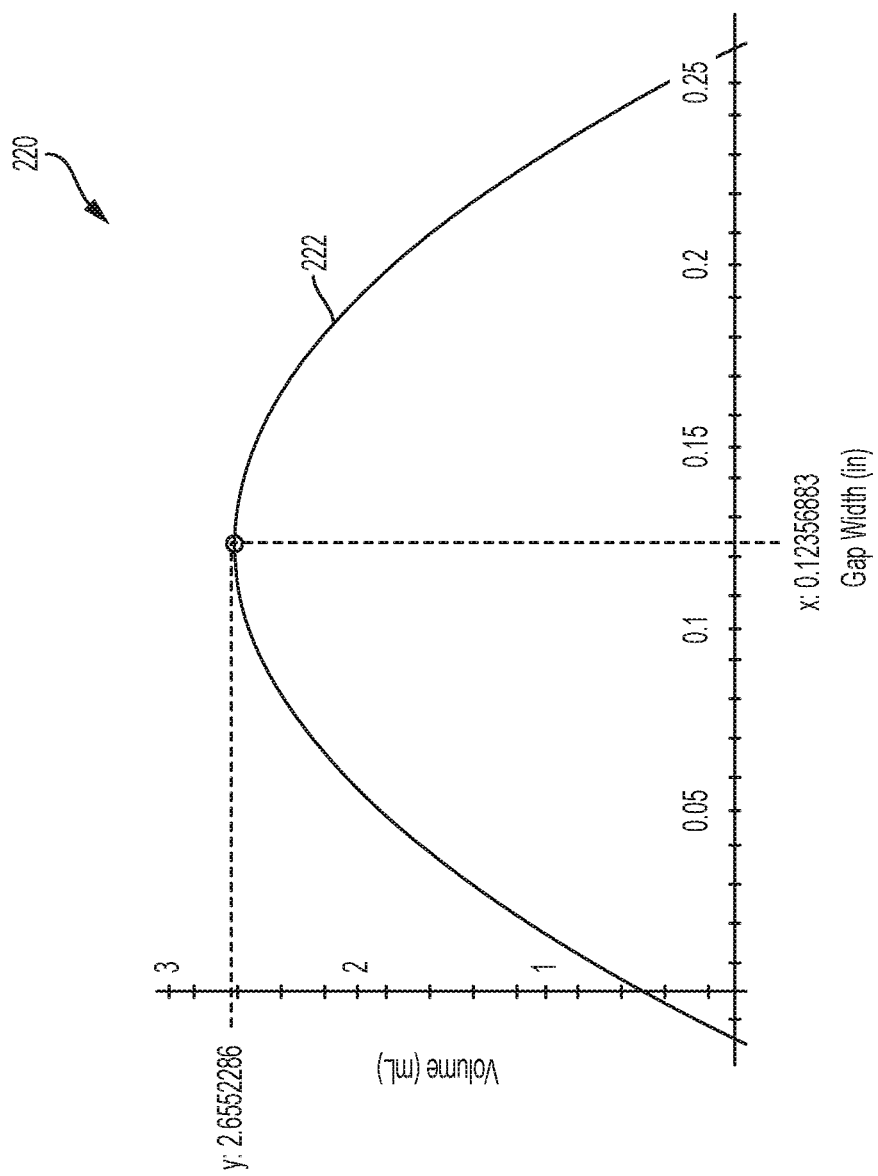
FIG. 17 is a graphical depiction of a curve representative of gap width "d" versus horizontal retention volume, according to one aspect of the present disclosure.

Having disclosed several examples of syringe tips comprising drip flanges arranged in a manner to facilitate wicking fluid in a space defined between the drip flanges by capillary action, the disclosure now turns to a theoretical analysis of capillary action and in particular the formation of capillary bridges and capillary-bridge forces created between flat planes. The analysis is facilitated by reference to several graphical illustrations in FIGS. 12, 15, 16, and 17, where FIG. 12 is a graphical illustration of gap width "d" versus upright retention volume, FIG. 15 is a graphical illustration of gap width "d" versus horizontal retention volume, FIG. 16 is a graphical representation of gap width "d" versus retention volume percentage, and FIG. 17 is a graphical representation of theoretical gap width "d" versus horizontal retention volume calculated as described herein.

Studies regarding capillary bridges have been conducted and documented in Chapter II in the book: P. A. Kralchevsky and K. Nagayama, "Particles at Fluid Interfaces and Membranes" (Attachment of Colloid Particles and Proteins to Interfaces and Formation of Two-Dimensional Arrays) or Elsevier, Amsterdam, 2001; pp. 469-502, the contents of which are herein incorporated by reference; and http://lcpe.uni-sofia.bg/files/punblications/2001/2001-26-Book11.pdf, the contents of which are incorporated herein by reference. Excerpts from this reference are provided hereinbelow under the headings CAPILLARY BRIDGES AND CAPILLARY-BRIDGE FORCES and the ROLE OF THE CAPILLARY BRIDGES IN VARIOUS PROCESSES AND PHENOMENA.

Capillary Bridges and Capillary-Bridge Forces

Capillary bridges have been recognized for many systems and phenomena including, for example, consolidation of granules and soils, wetting of powders, capillary condensation and bridging in the atomic-force-microscope measurements, etc. The capillary bridge force is oriented normally to the plane of the three-phase contact line and consists of contributions from the capillary pressure and surface tension. A toroid (circle) approximation can be applied to quantify the shape of capillary bridges and the capillary-bridge force. More reliable results can be obtained using the exact profile of the capillary bridge, which is determined by the Plateau sequence of shapes: (I) nodoid with "neck", (2) catenoid, and (3) unduloid with "neck". For the shapes (1-3) the capillary-bridge force is attractive and can be described by the equations listed in TABLE 1 below. Two plane-parallel plates are considered as an example. The treatment is similar for fluid-in-fluid bridges between two hydrophilic plates and for gas-in-fluid bridges between two hydrophobic plates. Nucleation of capillary bridges is possible when the distance between the plates is smaller than a certain limiting value. See P. A. Kralchevsky et al.

TABLE 1

Bridges With Neck, See P.A. Kralchevsky et al.

Bridges with "neck"

| $-\infty < p < 0$<br>Nodoid | $p = 0$<br>Catenoid | $0 < p < \frac{1}{2}$<br>Unduloid |
|---|---|---|
| $L_{nn}$, see Eq. (11.59) | $L/r_c = 1.3255$<br>$L/2r_0 = 1.200$ | $L_{nn}$, see Eq. (11.59) |

Notation: $q_1 = (1 - \rho_0^2/\rho_1^2)^{1/2}$,
$\sin\phi_1 = q_1^{-1}(1 - \rho_0^2/\rho_1^2)^{1/2}$
$\varepsilon = -1$ for nodoid, $\varepsilon = +1$ for unduloid Shape: $(\rho_0 \le \rho \le \rho_1)$
$|k_1|z(\rho) = \pm(\rho_1 E(\phi_1, q_1) + \varepsilon\rho_0 F(\phi_1, q_1) - [(\rho^2 - \rho_0^2)(\rho_1^2 - \rho^2)^{1/2}/\rho\}$ Area: 
$$A(r) = 2\pi \int_{r_0}^{r} dr\, r(1 + z_r^2)^{\frac{1}{2}} = \frac{2\pi}{k_1^2}\left\{\rho_1 E(\phi_1, q_1) - [(\rho^2 - \rho_0^2)(\rho_1^2 - \rho^2)]^{\frac{1}{2}}/\rho\right\}$$

Volume:
$$V(r) = \pi\int_{r_0}^{r} dr\, r^2 dz/dr = \frac{\pi\rho_1}{3|k_1^3|}\left\{\beta E(\phi_1, q_1) - \rho_0^2 F(\phi_1, q_1) - (\beta + \rho^2)[(\rho^2 - \rho_0^2)(\rho_1^2 - \rho^2)]^{\frac{1}{2}}/(\rho\rho_1)\right\}$$

$\beta = (2\rho_0^2 + 2\rho_1^2 + 3\,\varepsilon\rho_0\rho_1)$

Running Slope: $\tan\varphi = dz/dr$
$\cos^2\varphi = (\rho^2 - \rho_0^2)(\rho_1^2 - \rho^2)/\rho^2$ Role of the Capillary Bridges in Various Processes and Phenomena Adhesion of spherical beads to a flat plate have been studied experimentally and it has been established that in clean dry air the adhesion was negligible, but in a humid atmosphere, marked adhesion has been observed, particularly with hydrophilic glass surfaces. At saturated humidity the adhesion was the same as that observed if a small drop of water was placed between the surfaces. Similar results were obtained in the earlier experimental studies. The formation of a fluid bridge between two solid surfaces can lead to the appearance of attractive (adhesive) force between them owing to the decreased pressure inside the fluid bridge and the direct action of the surface tension force exerted around the annulus of the meniscus. In some cases the force due to capillary bridge can be also repulsive. In all cases this force is perpendicular to the planes of the three-phase contact lines (circumferences) on the solid surfaces. See P. A. Kralchevsky et al.

The importance of the capillary bridges has been recognized in many experimental and practical systems. For example, the effect of capillary bridges may be considered for the assessment of the water saturation in soils and the adhesive forces in any moist unconsolidated porous media. The action of capillary-bridge force is often detected in the experiments with atomic force microscopy. The capillary-bridge force is also one of the major candidates for explanation of the attractive hydrophobic surface force. See P. A. Kralchevsky et al.

Pioneering studies (both experimental and theoretical) of capillary bridges have been undertaken and have been classified in accordance with the shapes of the capillary bridges (the surfaces of constant mean curvature) and investigated their stability. The study of the instability of cylindrical fluid interfaces was further extended by consideration also of jets of viscous fluid. The shapes of capillary bridges between two solid spheres and between sphere and plate also have been experimentally investigated. Exact solutions of the Laplace equation of capillarity for the respective bridges also have been obtained. All these studies deal with capillary bridges between two solids. See P. A. Kralchevsky et al.

Capillary bridges can appear also between solid and fluid phases and have been studied (both theoretically and experimentally) by the formation and stability of holes in a sheet of fluid. Also examined theoretically was the appearance of a capillary bridge, which "jumps" from a fluid film to wet the tip of the atomic force microscope. It has been investigated experimentally the nucleation and growth of fluid bridges between a horizontal fluid interface and a horizontal solid plate at a short distance apart. P. A. Kralchevsky et al.

With the theoretical and experimental framework summarized above and discussed by P. A. Kralchevsky et al., the present disclosure now turns to various experimental results obtained by the present applicant. A first experiment was conducted employing two solid parallel plates positioned in a vertical (upright) orientation and spaced apart by a predetermined gap width. The experiment was configured such that the gap between the parallel plates could be varied. Once a gap was set, a drop of saline was introduced between the plates and the retention volume of the drop of saline was measured. The measurements were repeated for gap thicknesses between 0.01 in to 0.25 in. At each gap thickness setting, a drop of saline was introduced between the plates and as the gap width was varied the upright retention volume was measured. These results are tabulated in TABLE 2 and are graphically depicted in FIG. 12.

TABLE 2

| Gap Thickness (in) | Max Vol (mL) | Ret Vol (mL) | Ret % |
|---|---|---|---|
| 0.010 | 0.83 | 0.523 | 63% |
| 0.020 | 1.10 | 0.723 | 66% |
| 0.030 | 1.45 | 0.867 | 60% |
| 0.040 | 1.63 | 0.870 | 53% |
| 0.050 | 1.89 | 0.860 | 45% |
| 0.060 | 2.08 | 1.010 | 49% |
| 0.100 | 2.53 | 0.910 | 36% |
| 0.125 | 2.91 | 0.840 | 29% |
| 0.150 | 2.65 | 0.640 | 24% |
| 0.250 | 0.00 | 0.000 | 0% |

Figure 14:
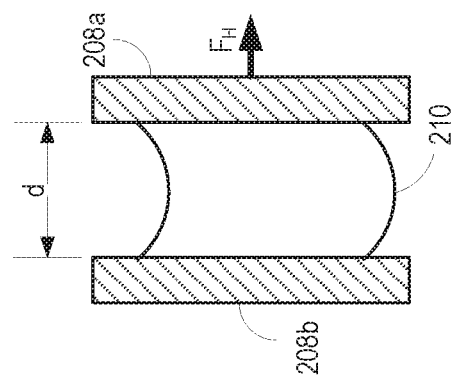
FIG. 14 is a schematic representation of a concave capillary bridge between two planes in a horizontal orientation defining a horizontal retention volume versus gap width "d".
Figure 13:
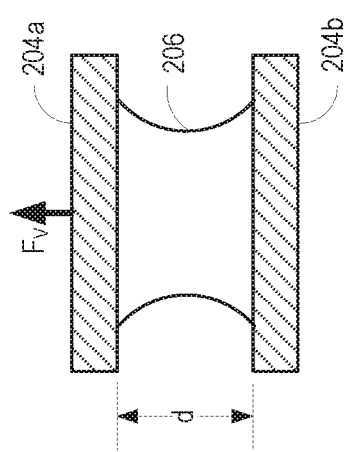
FIG. 13 is a schematic representation of a concave capillary bridge between two planes in an upright orientation defining an upright retention volume versus gap width "d".

FIG. 12 is a graphical depiction 200 of a curve 202 representative of gap width "d" versus upright retention volume, according to one aspect of the present disclosure. The vertical axis represents Volume (mL) and the horizontal represents Gap Width (in). FIG. 13 is a schematic representation of a concave capillary bridge between two planes in an upright orientation (i.e., when the syringe tip is oriented vertically upright) defining an upright retention volume versus gap width "d". As shown in FIG. 13, two solid plates 204a, 204b are positioned parallel to each other in a horizontal position and spaced apart by a gap width "d" in an upright orientation. A drop of saline 206 is introduced between the two solid plates 204a, 204b and defines an upright retention volume. A vertical (upright) capillary force "Fv" retains the drop of saline 206 between the two solid plates 204a, 204b. As indicated in TABLE 2, the gap thickness "d" was varied from 0.01 in to 0.25 in as shown in the first column, labeled "Gap Thickness." At each gap width setting, a new saline drop was introduced between the two solid plates 204a, 204b positioned in parallel orientation relative to each other and the maximum volume (Max Vol) as well as the retention volume (Ret Vol) were measured. The retention volume is also expressed as a percentage (Ret %). These results are plotted in FIG. 12 as a curve 202. Referring to FIG. 12 and TABLE 2, the maximum volume 2.91 mL is observed at a gap thickness of 0.125 in and the maximum retention volume FIG. 14 is a schematic representation of a concave capillary bridge between two planes in a horizontal orientation (i.e., when the syringe tip is oriented horizontally) defining a horizontal retention volume versus gap width "d". A second experiment was conducted with two solid plates 208a, 208b positioned parallel to each other in a vertical orientation and horizontally spaced apart by a gap width "d" as shown in FIG. 14. A drop of saline 210 was introduced between the two solid plates 208a, 208b and the maximum volume (Max Volume [mL]) and the retention volume (Retention Volume [mL]) was measured at each gap width "d" setting. A horizontal capillary force "FH" retains the drop of saline 210 between the two plates 208a, 208b, while acting against the force of gravity. As the gap width setting "d" was varied, a new drop of saline 210 was introduced between the two plates 208a, 208b. It should be noted that the two solid plates 208a, 208b positioned in a parallel orientation relative to each other are positioned in a horizontal orientation when the drop of saline 210 is introduced therebetween and is subsequently rotated 90° to a vertical orientation. As shown in TABLE 3, three samples were tested from a gap width "d" of 0.01 in to 0.06 in. With the two solid plates 208a, 208b in the horizontal orientation, the initial weight (Initial Weight [g]) of the two solid plates 208a, 208b was measured and the weight after introducing the drop of saline 210 between the two solid plates 208a, 208b was measured (Weight after Fill [g]). After filling and weighing, the two solid plates 208a, 208b arranged in a parallel configuration relative to each other were rotated 90° to a vertical orientation and the weight was again measured (Weight after Horizontal [g]). With the two solid plates 208a, 208b now in the vertical orientation shown in FIG. 14, the maximum volume (Max Volume [mL]) and the retention volume (Retention Volume [mL]) were measured. The retention volume is also expressed as a percentage (%) of maximum volume (Max Vol [mL]). The results are tabulated in TABLE 3 and are graphically depicted in FIG. 15.

FIG. 15 is a graphical depiction 212 of a curve 214 representative of gap width "d" versus horizontal retention volume, according to one aspect of the present disclosure. The vertical axis represents Volume (mL) and the horizontal represents Gap Width (in). As shown in TABLE 3 and FIG. 15, the maximum retention volume of 1.03 mL is observed at a gap thickness of 0.06 in.

FIG. 16 is a graphical depiction 216 of a curve 218 representative of gap width "d" versus retention volume percentage in vertical (i.e., upright) orientation, according to one aspect of the present disclosure. The vertical axis represents Retention Volume Percentage (%) and the horizontal axis represents Gap Width (in). Retention Volume Percentage % (Ret %) with respect to (Gap Width (in) (Gap Thickness [in]) is provided in TABLE 2. The resulting curve 218 is plotted in FIG. 16, where the maximum retention volume percentage of 66% is observed at a gap width of 0.020 in. From the maximum retention volume percentage of 66% the retention volume percentage decreases as the gap width (e.g., thickness) increases until the gap width reaches 0.25 in at which point the retention percentage decreases to 0%.

FIG. 17 is a graphical depiction 220 of a curve 222 representative of theoretical gap width "d" versus horizontal retention volume, according to one aspect of the present disclosure. The curve was generated using a theoretical equation based on a catenoid as shown in TABLE 1. As shown in FIG. 17, the maximum retention volume 2.655 mL is observed at a gap width of 0.124 in. These results match quite well with the experimental results depicted in FIG. 12.

TABLE 3

| Gap Thickness (in) | Sample Number | Initial Weight (g) | Weight After Fill (g) | Weight After Horizontal (g) | Max Volume (mL) | Retention Volume (mL) | Retention % |
|---|---|---|---|---|---|---|---|
| 0.01 | 1 | 2.43 | 3.37 | 3.03 | 0.94 | 0.60 | 64% |
|  | 2 | 2.47 | 3.22 | 2.94 | 0.75 | 0.47 | 63% |
|  | 3 | 2.37 | 3.16 | 2.87 | 0.79 | 0.50 | 63% |
| 0.02 | 1 | 2.40 | 3.52 | 3.12 | 1.12 | 0.72 | 64% |
|  | 2 | 2.41 | 3.39 | 3.20 | 0.98 | 0.79 | 81% |
|  | 3 | 2.39 | 3.60 | 3.05 | 1.21 | 0.66 | 55% |

TABLE 3-continued

| Gap Thickness (in) | Sample Number | Initial Weight (g) | Weight After Fill (g) | Weight After Horizontal (g) | Max Volume (mL) | Retention Volume (mL) | Retention % |
|---|---|---|---|---|---|---|---|
| 0.03 | 1 | 2.45 | 3.89 | 3.31 | 1.44 | 0.86 | 60% |
|  | 2 | 2.41 | 3.91 | 3.28 | 1.50 | 0.87 | 58% |
|  | 3 | 2.40 | 3.81 | 3.27 | 1.41 | 0.87 | 62% |
| 0.04 | 1 | 2.47 | 4.06 | 3.23 | 1.59 | 0.76 | 48% |
|  | 2 | 2.47 | 4.19 | 3.37 | 1.72 | 0.90 | 52% |
|  | 3 | 2.50 | 4.09 | 3.45 | 1.59 | 0.95 | 60% |
| 0.05 | 1 | 2.47 | 4.48 | 3.44 | 2.01 | 0.97 | 48% |
|  | 2 | 2.50 | 4.46 | 3.35 | 1.96 | 0.85 | 43% |
|  | 3 | 2.64 | 4.35 | 3.40 | 1.71 | 0.76 | 44% |
| 0.06 | 1 | 2.47 | 4.55 | 3.50 | 2.08 | 1.03 | 50% |
|  | 2 | 2.56 | 4.59 | 3.52 | 2.03 | 0.96 | 47% |
|  | 3 | 2.53 | 4.66 | 3.57 | 2.13 | 1.04 | 49% |

Figure 19:
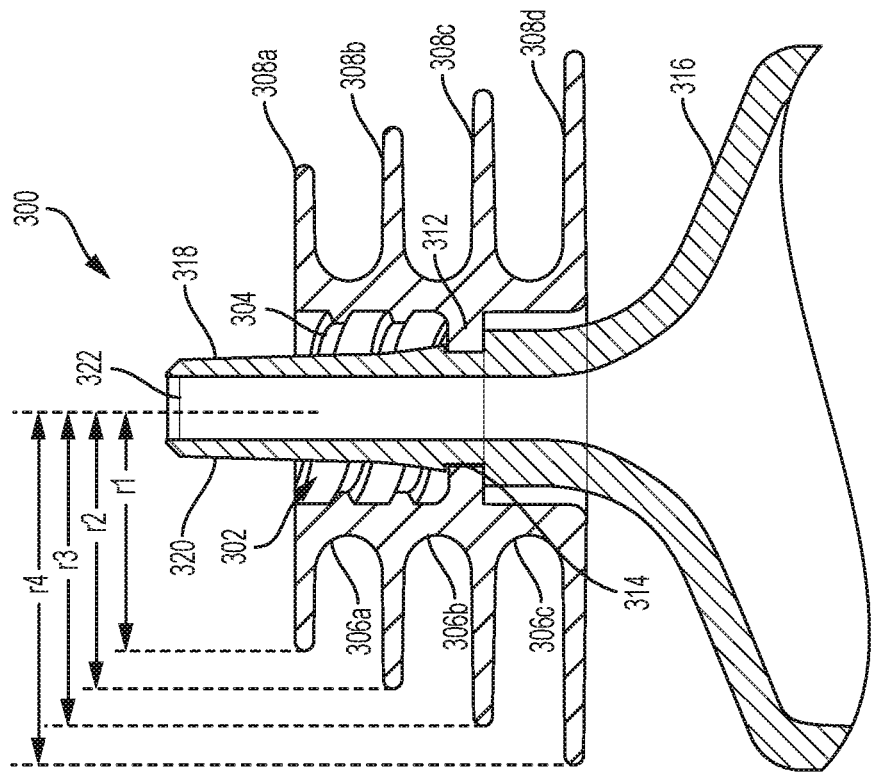
FIG. 19 illustrates the fluid wicking nut comprising a plurality of tiered drip flanges arranged to wick fluid by capillary action shown in FIG. 18, coupled to a tip of a syringe, according to one aspect of the present disclosure.
Figure 18:
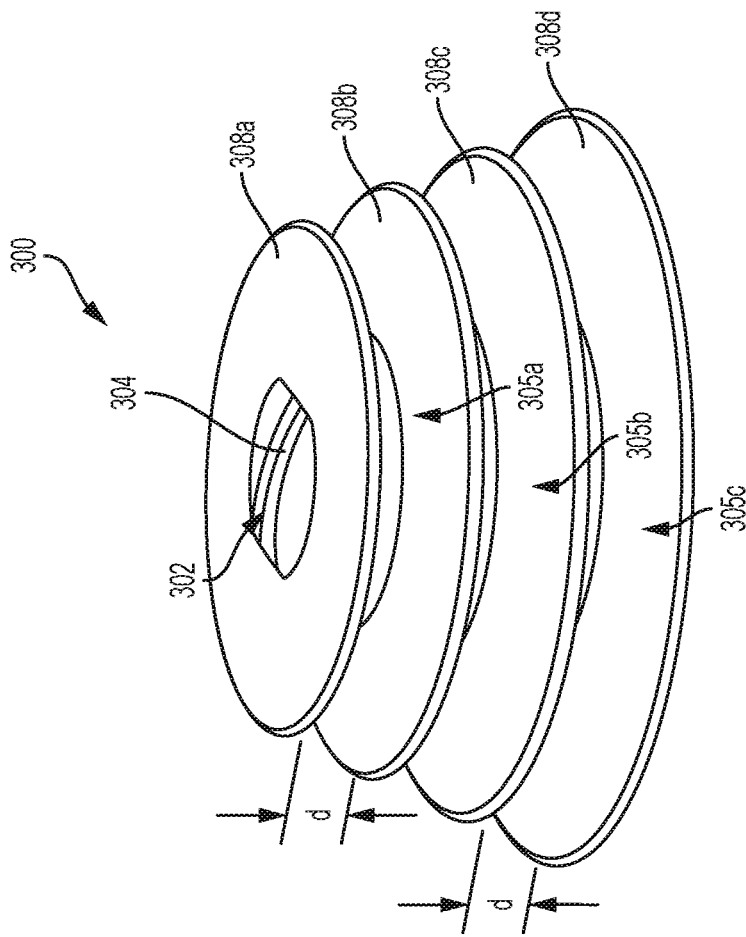
FIG. 18 is a perspective view of a fluid wicking nut comprising a plurality of tiered drip flanges arranged to wick fluid by capillary action configured to couple to a tip of a syringe, according to one aspect of the present disclosure.

Having provided a theoretical and experimental context for volume retention facilitated by wicking fluid in a space defined between parallel drip flanges by capillary action, FIGS. 18-47 provide several examples of fluid wicking tips comprising tiered drip flanges arranged in a manner to facilitate wicking fluid by capillary action in a narrow circumferential space defined between any two tiers of the tiered drip flanges. The various aspects may be utilized with or without a drip cup 110 as shown in aspects related to FIGS. 1-11. Accordingly, FIG. 18 illustrates a fluid wicking swivel nut 300 comprising tiered drip flanges configured to couple to a tip of a syringe, according to one aspect of the present disclosure. FIG. 19 illustrates the fluid wicking nut 300 shown in FIG. 18, coupled to a tip 318 of a syringe 316, according to one aspect of the present disclosure. With reference now to FIGS. 18 and 19, it can be seen that the tiered drip flange of the fluid wicking nut 300 comprises an aperture 302 for receiving the tip 318 of the syringe 316. The aperture 302 defines a threaded aperture 304 for fluidically coupling the syringe 316 to a flexible tube assembly, not shown. In one aspect, the threaded aperture 304 is configured as a threaded luer fitting to fluidly couple the tip 318 of the syringe 316 to a flexible tube assembly. The fluid wicking nut 300 also comprises a plurality of tiered drip flanges 308a, 308b, 308c, 308d that are positioned in parallel at a gap width "d". Although in some aspects the gap width "d" between the tiered drip flanges 308a-308d remains constant, it is contemplated that in various aspects the gap width "d" between the tiered drip flanges 308a-308d may vary. The tiered drip flanges 308a-308d are solid plates or planes that are configured to retain a predetermined volume of fluid. The surface area of each of the tiered drip flanges 308a-308d is smooth and continuous, although at least partially roughened surfaces, at least partially hydrophobic surfaces, and/or at least partially hydrophilic surfaces, or combinations of any surface arrangement are also contemplated.

In the configuration shown in FIGS. 18 and 19, the retention volume between the tiered drip flanges 308a-308d define a toroidal volume. Spaces 305a, 305b, 305c are defined between corresponding tiered drip flanges 308a-308b, 308b-308c, and 308c-308d for wicking fluid that drips from the tip 318 of syringe 316. Interior walls 306a, 306b, 306c are located between corresponding tiered drip flanges 308a-308b, 308b-308c define a radius of curvature to facilitate the flow of fluid between the spaces 305a-305c defined between the drip flanges 308a-308d. Each of the spaces 305a-305c defines a toroidal retention volume.

As shown in the example of FIG. 19, the tiered drip flanges 308a-308d define different radii "r". The first drip flange 308a has a first radius $r_1$, the second drip flange 308b has a second radius $r_2$, the third drip flange 308c has a third radius $r_3$, and the fourth drip flange 308d has a fourth radius $r_4$, where $r_1 < r_2 < r_3 < r_4$. It will be appreciated that in some aspects the radii may be constant such that $r_1 = r_2 = r_3 = r_4$. In other aspects the radii may vary such that $r_1 > r_2 > r_3 > r_4$. In other aspects, the radii may be selected such that the radii of the middle tiered drip flanges 308b, 308c is greater than the radii of the top and bottom drip flanges 308a, 308d. Other combinations also should be considered to be within the scope of the present disclosure.

Also shown in FIG. 19, the syringe tip 318 includes a circumferential groove 314 to receive a circumferential projection 312 defined by an internal portion of the wicking nut 300. This configuration enables the fluid wicking nut 300 to snap fit connect or couple to the tip 318 of the syringe 316. In other aspects, instead of the circumferential groove 314 and circumferential projection 312 snap fit connection, the fluid wicking nut 300 and the tip 318 may be configured with threads such that the fluid wicking nut 300 can be threadably engaged with the tip 318.

In operation, as saline or contrast fluid drips from the opening 322 defined in the tip 318 and flows down the sidewall 320, the fluid will contact the first surface of the first drip flange 308a and as more fluid drips, it will flow into the first space 305a defined between the first and second tiered drip flanges 308a-308b. As fluid continues to drip from the opening 322 and the first space 305a reaches its maximum retention volume $v_1$, excess fluid will flow into the second space 305b defined between the second and third tiered drip flanges 308b-308c. As the second space 305b reaches the maximum retention volume $v_2$ for the second space 305b, excess fluid will flow into the third space 305c until the maximum retention volume $v_3$ is reached. In this manner, the plurality of spaces 305a-305c fill to the maximum retention volume $v_{max} = v_1 + v_2 + v_3$ for the wicking nut 300. As additional fluid drips, the excess will drip from the fourth drip flange 308d. While three spaces 305a-305c are illustrated in FIGS. 18-19, fluid wicking tips with fewer or more spaces 305 are contemplated and within the scope of the present disclosure.

Figure 21:
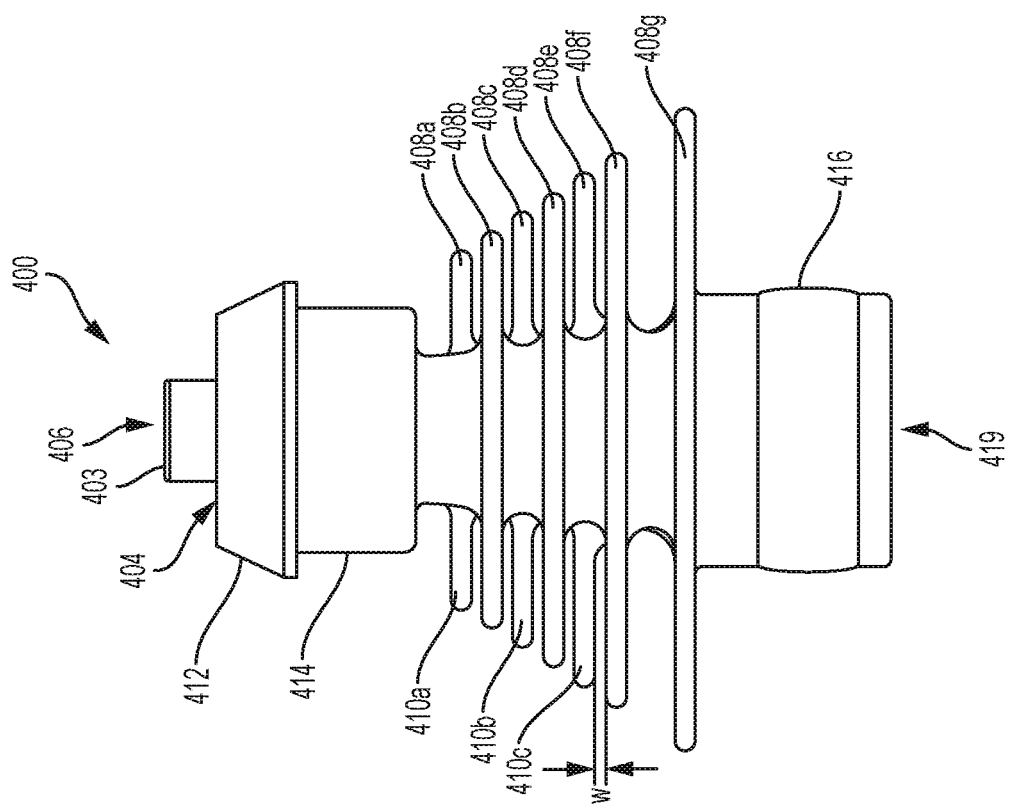
FIG. 21 is a side view of the fluid wicking tip comprising a plurality of staggered tiered drip flanges shown in FIG. 20, according to one aspect of the present disclosure.
Figure 20:
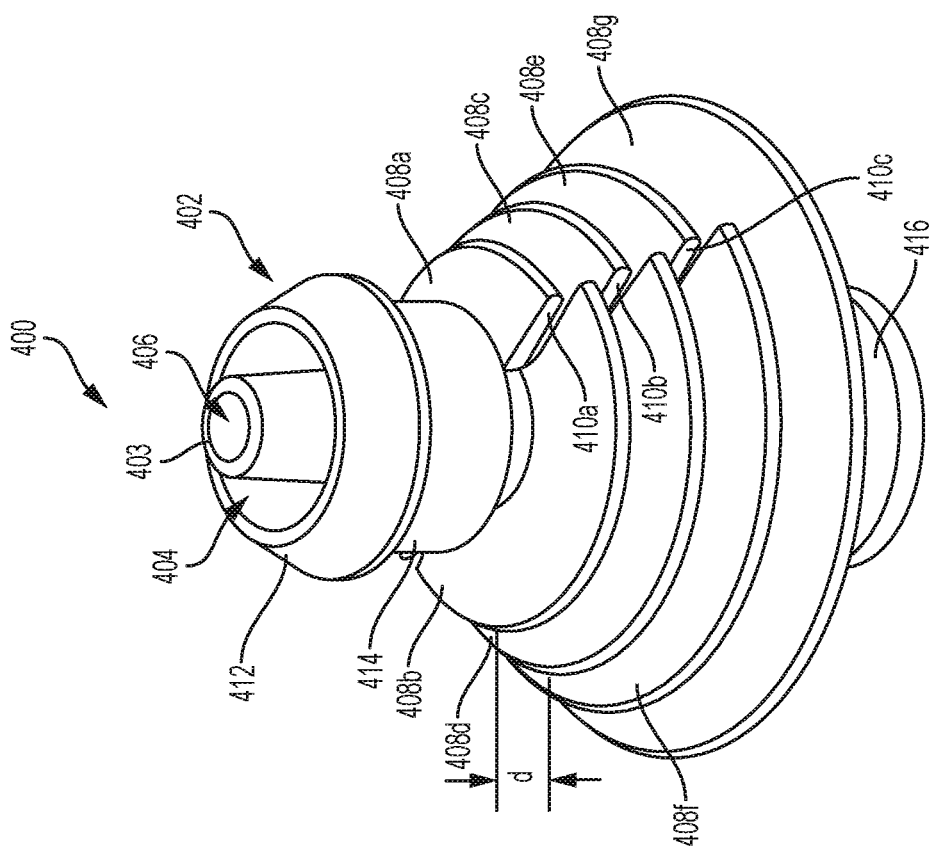
FIG. 20 is a perspective view of a fluid wicking tip comprising a plurality of staggered tiered drip flanges arranged to wick fluid by capillary action and configured to couple to a tip of a syringe, according to one aspect of the present disclosure.

FIGS. 20-22 illustrate a fluid wicking tip 400 comprising a plurality of staggered tiered drip flanges configured to couple to a tip of a syringe, according to one aspect of the present disclosure. FIG. 20 is a perspective view of the fluid wicking tip 400. FIGS. 21 and 22 are different side views of the fluid wicking tip 400. With reference now to FIGS.

20-22, in one aspect, the fluid wicking tip 400 also comprises a connector tip 402 defining a circumferential tapered surface 412 and a cylindrical wall 414, which may be threaded on an interior surface or otherwise configured to attach to a fluid transfer assembly with a fluid tight connection. For example, a tip 403 is provided to fluidly couple to a flexible fluid assembly. A space 404 is defined between the tip 403 and the connector tip 402. The volume defined by the space 404 is suitable for partial containment of a fluid spill. The tip 403 defines an aperture 406 that extends through the body of the staggered tiered fluid wicking tip 400 and defines a fluid channel 419. The fluid channel 419 is fluidly coupled to a syringe tip via a syringe tip coupling adapter 416, which may be attached to the syringe tip by conventional means such as adhesive bonding or laser welding, and is fluidly coupled to a flexible tube assembly via the tip 403. Accordingly, the staggered tiered fluid wicking tip 400 fluidly couples a syringe with a flexible tube assembly to enable the transfer of fluid to and from the syringe via the fluid channel 419 and aperture 406 in the tip 403.

Below the connector tip 402, the fluid wicking tip 400 comprises a plurality of staggered tiered drip flanges 408a, 408b, 408c, 408d, 408d, 408e, 408f. The drip flanges are rounded on an outer perimeter and define walls 410a, 410b, 410c, as shown, corresponding to staggered tiered drip flanges 408a, 408c, 408e. Similar walls, not shown, are defined by the staggered tiered drip flanges 408b, 408d, 408f. A gap width "d" is defined between the drip flanges corresponding to the same tier and a gap width "w" is defined between the drip flanges of two subsequent tiered drip flanges, where the gap width d>w. The smaller gap width "w" facilitates the fluid to flow between staggered tiers. A continuous circumferential base drip flange 408g is disposed between the syringe tip coupling adapter 416 and the staggered tiered drip flange 408f. Below the continuous circumferential base drip flange 408g is a syringe tip coupling adapter 416 that is configured to couple to a tip of a syringe. Due to the nature of the staggered tiered configuration, a gap width "D" is defined between the continuous circumferential base drip flange 408g and the staggered tiered drip flange 408e, where the gap width D>d.

Narrow circumferential spaces 418a, 418b, 418c, 418d, 418e, 418f are defined between the staggered tiered drip flanges 408a-408g between any two tiers. The narrow circumferential spaces 418a-418f each define a unique predetermined volume and are arranged to facilitate wicking fluid that may spill from the tip 403 and/or from the containment connector tip 402. Spilled fluid flows down the circumferential tapered surface 412, the cylindrical wall 414, and collects on the surface areas of top staggered tiered drip flanges 408a, 408b nearest the tip 403. As fluid continues to spill, the fluid flows from the surfaces of first staggered tiered drip flanges 408a, 408b and by way of capillary action is wicked into either the narrow circumferential space 418a defined between the two staggered tiered drip flanges 408a, 408c or the narrow circumferential space 418b defined between the two staggered tiered drip flanges 408b, 408d, or some combination thereof, depending on the particular orientation of the fluid wicking tip 400. Each of the narrow circumferential spaces 418a, 418b defines a unique predetermined volume. As previously described, the volume defined by the narrow circumferential spaces 418a, 418b can hold or retain a maximum amount of fluid, which is known as the maximum retention volume. When a maximum retention volume is reached, excess spilled fluid continues to flow to fill the narrow circumferential space 418c defined between the staggered tiered drip flanges 408c, 408e, the space, 418d defined between the staggered tiered drip flanges 408d, 408f, the narrow circumferential space 418e defined between the staggered tiered drip flanges 408e, 408g, and the narrow circumferential space 418f defined between tiered drip flanges 408f, 408g.

Figure 24:
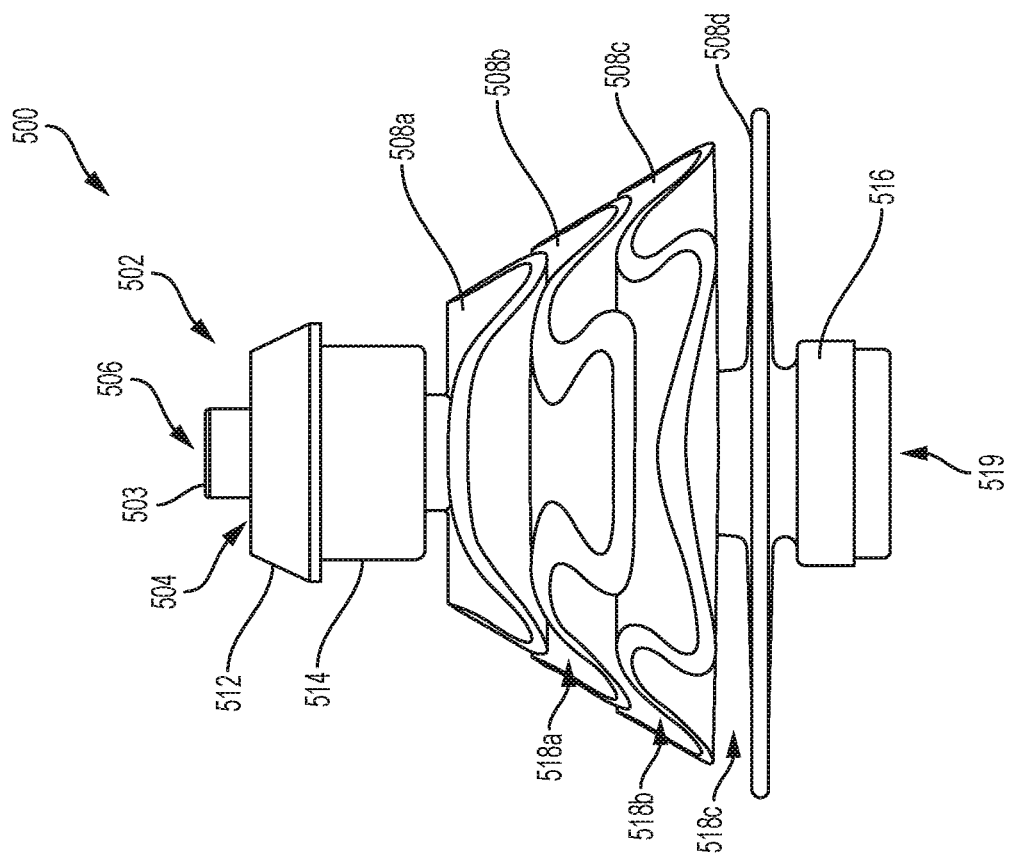
FIG. 24 is a side view of the fluid wicking tip comprising a plurality of ruffled tiered drip flanges shown in FIG. 23, according to one aspect of the present disclosure.
Figure 23:
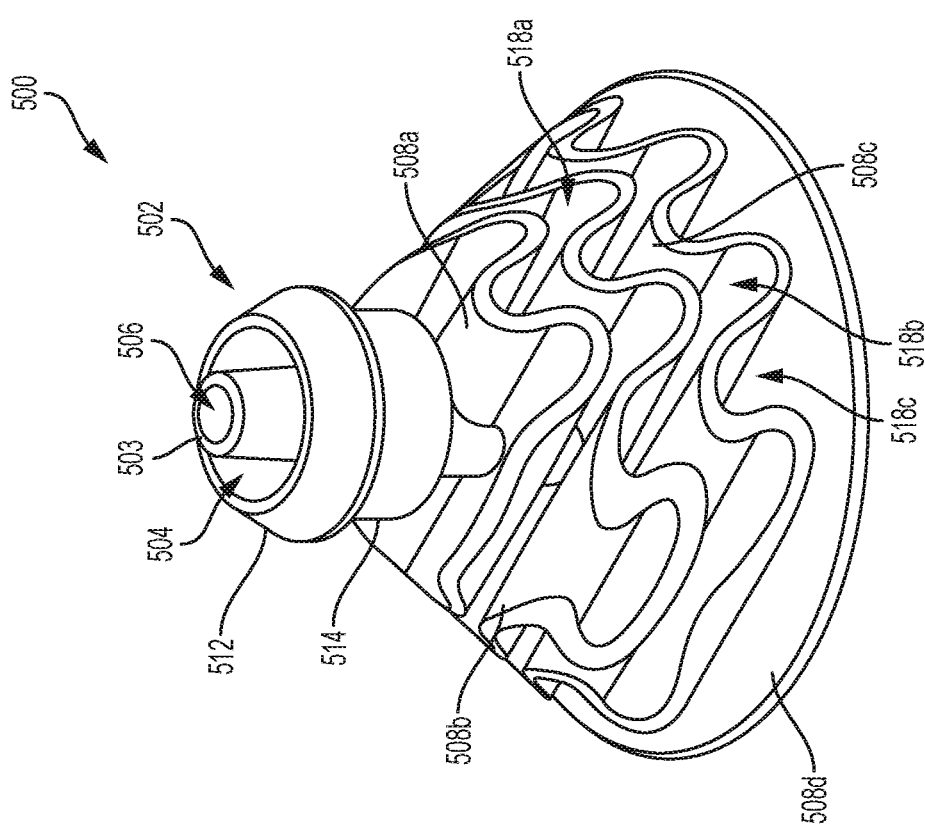
FIG. 23 is a perspective view of a fluid wicking tip comprising a plurality of ruffled tiered drip flanges arranged to wick fluid by capillary action and configured to couple to a tip of a syringe, according to one aspect of the present disclosure.
Figure 26:
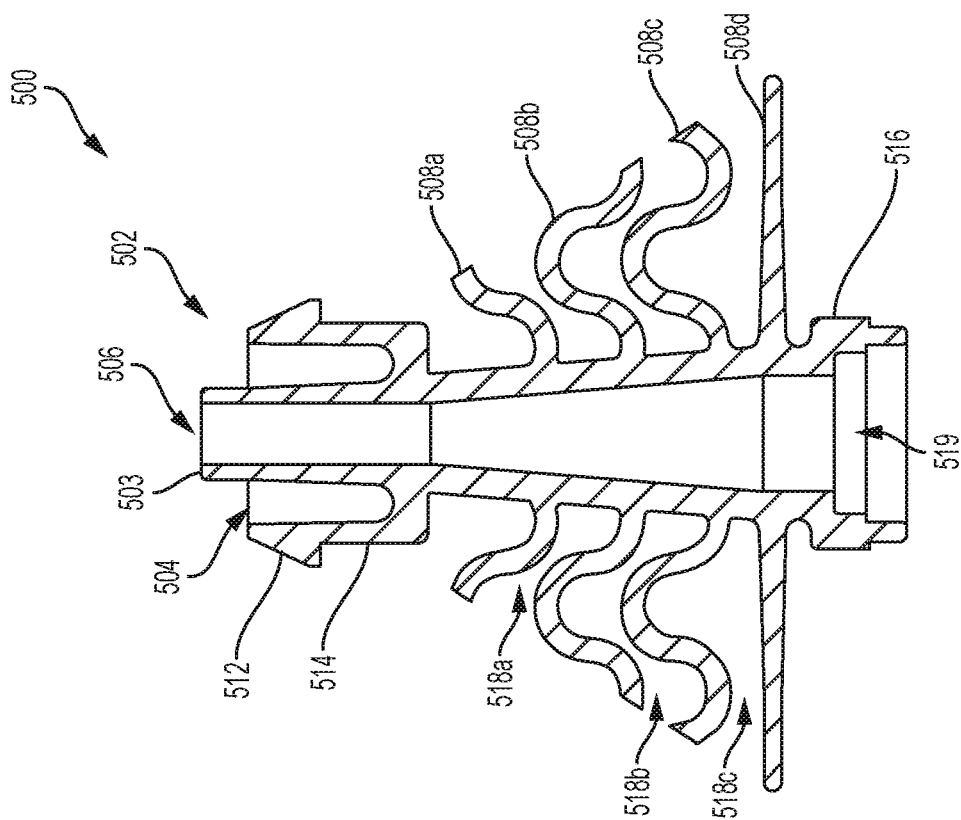
FIG. 26 is a sectional view of the fluid wicking tip comprising a plurality of ruffled tiered drip flanges shown in FIG. 25, according to one aspect of the present disclosure.
Figure 25:
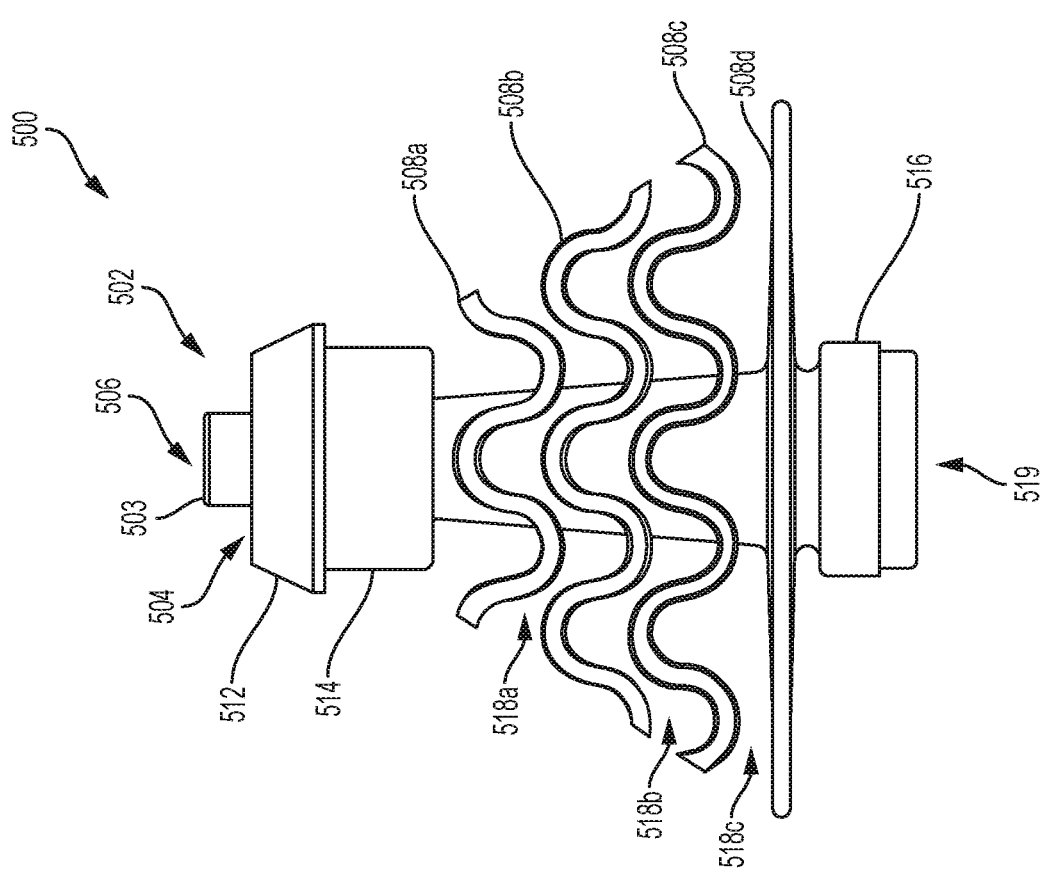
FIG. 25 is a sectional view of the fluid wicking tip comprising a plurality of ruffled tiered drip flanges shown in FIG. 24, according to one aspect of the present disclosure.

FIGS. 23-27 illustrate a fluid wicking tip 500 comprising a plurality of ruffled tiered drip flanges arranged to wick fluid by capillary action and configured to couple to a tip of a syringe, according to one aspect of the present disclosure. FIG. 23 is a perspective view of one aspect of the fluid wicking tip 500. FIG. 24 is a side view of the fluid wicking tip 500 shown in FIG. 23. FIG. 25 is a sectional view of the fluid wicking tip 500 shown in FIG. 24. FIG. 26 is a sectional view of the fluid wicking tip 500 shown in FIG. 25. FIG. 27 is a sectional view of the fluid wicking tip 500 shown in FIG. 26. With reference now to FIGS. 23-27, in one aspect, the fluid wicking tip 500 comprises a connector tip 502 defining a tapered surface 512 and a cylindrical wall 514. A tip 503 is provided to fluidly couple to a flexible fluid assembly. A narrow circumferential space 504 is defined between the tip 503 and the connector tip 502. The volume defined by the space 504 is suitable for partial containment of a fluid spill. The tip 503 defines an aperture 506 that extends through the body of the fluid wicking tip 500 and defines a fluid channel 519. The fluid channel 519 is fluidly coupled to a syringe tip via a syringe tip coupling adapter 516, which may be attached to the syringe tip by conventional means such as adhesive bonding or laser welding, and is fluidly coupled to a flexible tube assembly via the tip 503. Accordingly, the fluid wicking tip 500 fluidly couples a syringe with a flexible tube assembly to enable the transfer of fluid to and from the syringe via the fluid channel 519 and aperture 506 in the tip 503.

Below the connector tip 502, the fluid wicking tip 500 comprises a plurality of ruffled tiered drip flanges 508a, 508b, 508c. A smooth continuous circumferential base drip flange 508d is disposed between the syringe tip coupling adapter 516 and the ruffled tiered drip flange 508c. Below the smooth continuous circumferential base drip flange 508d is a syringe tip coupling adapter 516 that is configured to couple to a tip of a syringe. The ruffled tiered drip flanges 508a-508c are ruffled and define a periodic wavelike structure as best seen in the sectional views depicted in FIGS. 25-26. The ruffled wavelike structure defined a larger surface area that enables the retention of more volume than the flat drip flange counterparts shown in FIGS. 2, 18, and 20-22, and may retain greater fluid volumes due to the ruffling when the syringe is in the horizontal position.

The narrow circumferential spaces 518a, 518b, 518c defined between the drip flanges 508a-508d define predetermined volumes for wicking fluid spilling from the tip 503 and/or from the connector tip 502. Spilled fluid flows down the tapered surface 512, the cylindrical wall 514, and collects on the surface area of first ruffled drip flange 508a. As the fluid continues to spill, the fluid flows from the surface of first ruffled drip flange 508a and by way of capillary action is wicked into either the narrow circumferential space 518a defined between the ruffled tiered drip flanges 508a, 508c. The narrow circumferential space 518a defines a unique predetermined volume. As previously described, the narrow circumferential space 518a can hold or retain a maximum amount of fluid, which is known as the maximum retention volume. When maximum retention volume is reached, excess spill fluid continues to flow and fills the narrow circumferential space 518b defined between the ruffled tiered drip flanges 508b, 508c and ultimately the narrow circumferential space 518c define between the ruffled tiered drip flange 508c and smooth continuous circumferential base drip flange 508d.

FIGS. 28-32 illustrate a sleeved modular syringe system 600, according to one aspect of the present disclosure. FIG. 28 is a perspective view of a sleeved modular syringe system 600 comprising one aspect of a syringe 602 and one aspect of a sleeve 604 having a plurality of tiered drip flanges 614a-614c, slidably disposed over the syringe. FIG. 29 is a partial sectional view of the sleeved modular syringe system 600. FIG. 30 is an exploded view of the sleeved modular syringe system 600 with the sleeve 604 shown separated from the syringe 602. FIG. 31 is a perspective view of the syringe 602. FIG. 32 is a perspective view of the sleeve 604. With reference now to FIGS. 28-32, in one aspect, a sleeved modular syringe system 600 is provided. The sleeved modular syringe system 600 comprises a syringe 602 and a sleeve 604 configured to be slidably disposed over the syringe 602. While illustrated as a modular system, in other aspects, the sleeve 604 and/or tiered drip flanges 614a-614c may be directly molded as part of the cylindrical body 606 of the syringe 602.

In one aspect, the syringe 602 comprises a cylindrical body 606, a conical or tapered portion 608 extending from the cylindrical body 606, and a distal tip 610 located at the distal end extending from the tapered portion 608. The distal tip 610 is configured to fluidly couple to a flexible tube assembly, for example with a wicking drip tip according to various aspects described herein. The distal tip 610 may be employed to draw fluid into the syringe 602 and expel fluid from the syringe 602. The proximal end of the cylindrical body 606 comprises tabs 622a, 622b, 622c that define a space therebetween for receiving the proximal end of the sleeve 604 and rotatably couple the syringe 602 and the sleeve 604.

In one aspect, the sleeve 604 comprises a cylindrical body 612 defining an opening 624 sized and configured to enable the sleeve 604 to be slidably disposed over the cylindrical body 606 of the syringe 602. The sleeve 604 comprises a plurality of tiered drip flanges 614a, 614b, 614c disposed about the outer circumference of the cylindrical body 612 of the sleeve 604. As shown in FIG. 29, for example, the tiered drip flanges 614a, 614b, 614c are disposed along the cylindrical body 612 of the sleeve 604 and extend progressively further away from the cylindrical body 612 such that the tiered drip flange 614c located closer to the proximal end has a greater outer diameter than the drip flange 614a located closer to the distal end of the sleeve 604. The first and second spaces 626a, 626b defined between the corresponding tiered drip flanges 614a, 614b and tiered drip flanges 614b, 614c defines a predetermined volume to hold or retain fluid that spills from the tip 610 of the syringe 602, for example by capillary action and/or surface tension as detailed herein. Spilled fluid flows along the cylindrical body 606 of the syringe 602 and by way of capillary action it is wicked into the first space 626a until the volume of fluid retained in the space reaches the maximum retention volume. Excess fluid flows in to the second space 626b until the maximum retention volume is reached. The outer portion of the cylindrical body 612 of the sleeve 604 also comprises engagement lugs 616a, 616b, 618a for engaging the sleeved modular syringe system 600 to an injector.

As shown in FIGS. 28 and 30-32, the sleeve 604 can be placed in rotational locking engagement with the syringe 602 by way of locking tabs 620a, 620b, 620c (and others if necessary). The sleeve 604 is slidably disposed over the cylindrical body 606 of the syringe 602 such that the tabs 620a-620c are positioned in the gaps defined between the tabs 622a, 622b, 622c such that the syringe 602 is rotatably coupled to the sleeve 604. The sleeve 604 may be attached to the outer surface of syringe 602, for example by a friction fit or snap fit, or alternatively may be adhered by an adhesive or laser welded to syringe 602.

Figure 33:
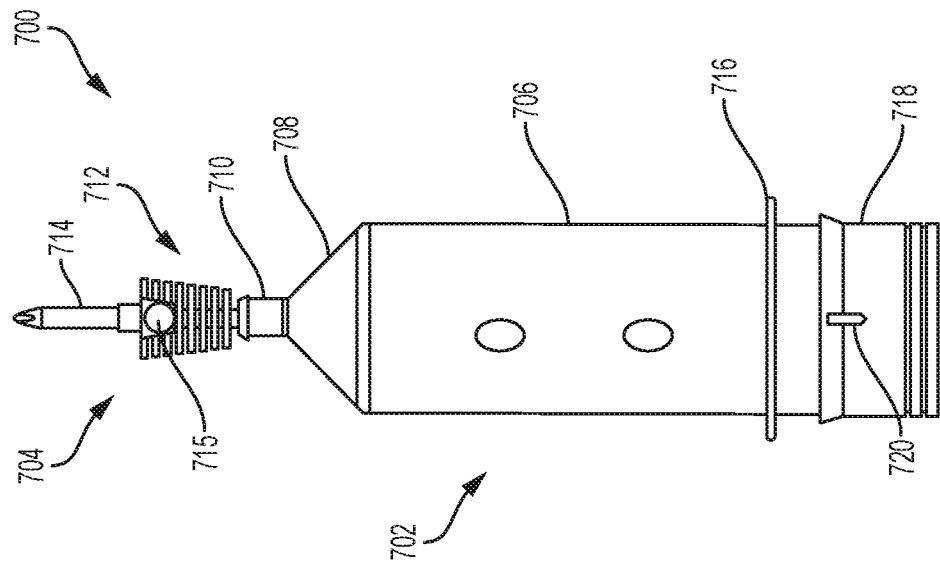
FIG. 33 is a perspective view of a fluid dispensing system, according to one aspect of the present disclosure.
Figure 34:
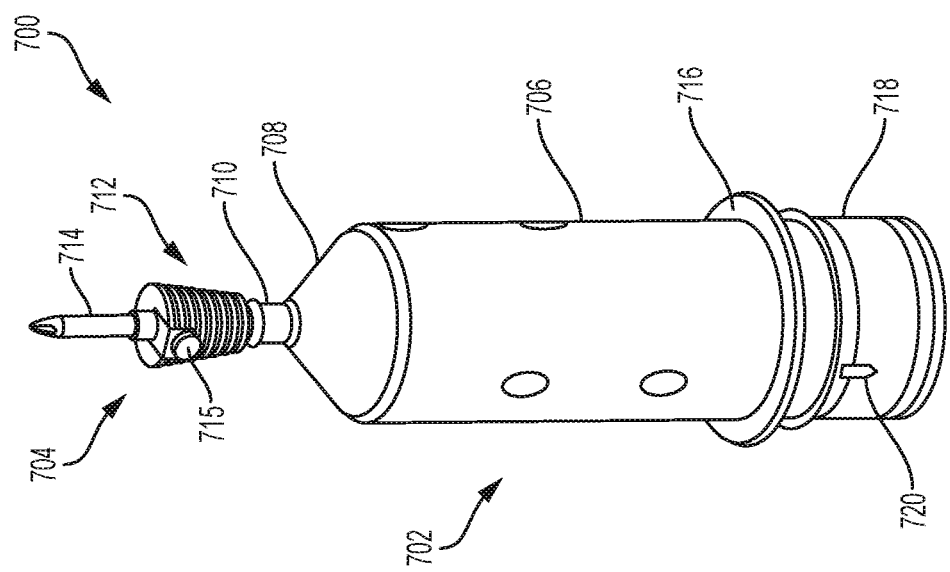
FIG. 34 is a front view of the fluid dispensing system shown in FIG. 33, according to one aspect of the present disclosure.
Figure 36:
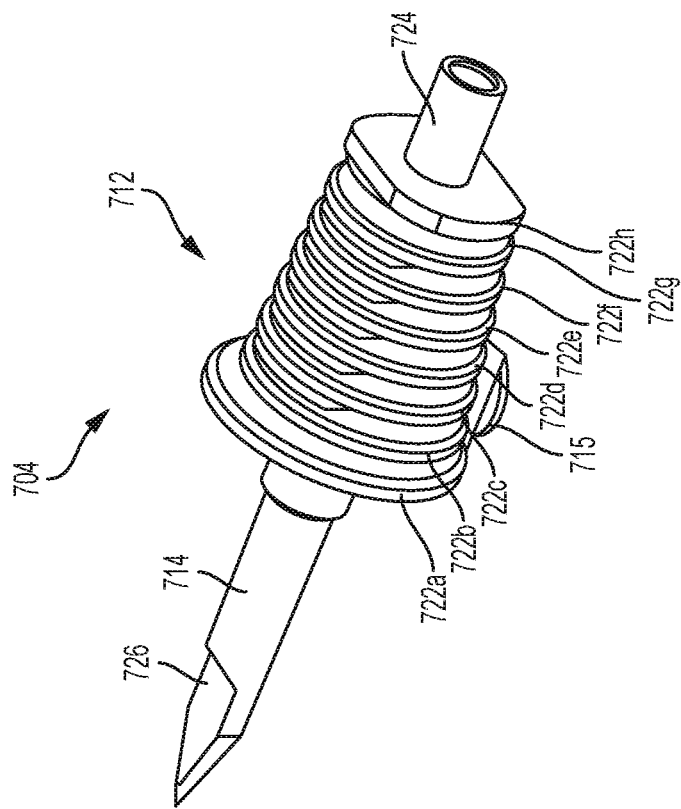
FIG. 36 is a perspective view of the spike tip comprising a plurality of tiered drip flanges shown in FIG. 35, according to one aspect of the present disclosure.
Figure 35:
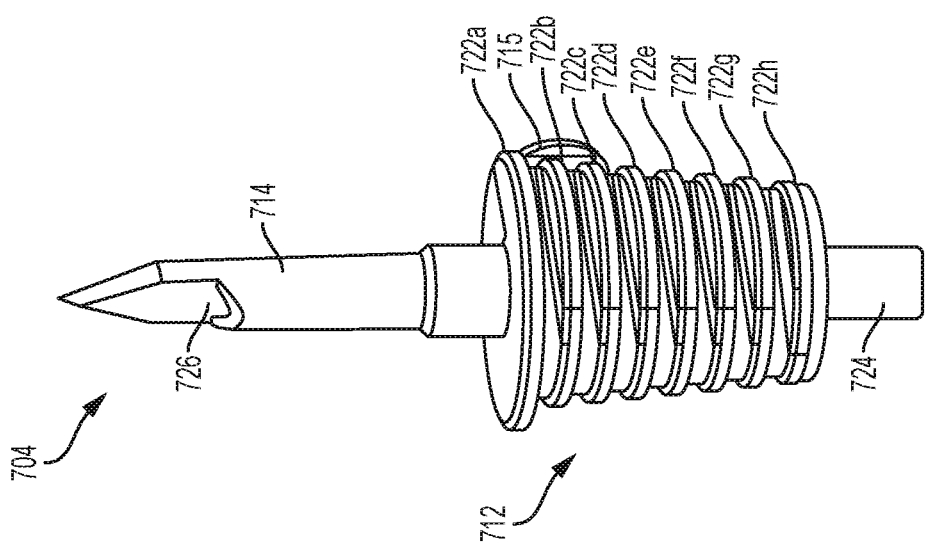
FIG. 35 is a perspective view of a spike tip comprising a plurality of tiered drip flanges, according to one aspect of the present disclosure.

FIGS. 33-34 illustrate a fluid dispensing system 700 comprising a syringe 702 fluidly coupled to a spike tip 704 comprising a fluid wicking tip 712 comprising a plurality of tiered drip flanges, according to one aspect of the present disclosure. FIG. 33 is a perspective view of the fluid dispensing system and FIG. 34 is a front view of the fluid dispensing system 700. With reference to FIGS. 33-34, in one aspect, the fluid dispensing system 700 comprises a syringe 702 fluidly coupled to a spike tip 704 comprising a fluid wicking tip 712. The syringe 702 comprises a cylindrical body 706, a tapered conical portion 708 extending from the cylindrical body 706, and a tip 710 extending from the tapered conical portion 708. The tip 710 is sized and configured to fluidly couple to the spike tip 704. The cylindrical body 706 comprises a circumferential drip flange 716. A proximal end of the cylindrical body 706 comprises a cylindrical portion 718 configured to operatively couple to an injector. An engagement lug 720 is provided for engaging the syringe 702 to the injector. The spike tip 704 comprises a piercing tip 714 and a fluid wicking tip 712. The piercing tip 714 comprises a vent button 715. The fluid wicking tip 712 wicks fluid spills within the tiered flanges as described according to various aspects herein. Any excess fluid is caught below by the circumferential drip flange 716 on the cylindrical body 706.

FIGS. 35-38 illustrate various perspective views of the spike tip 704 comprising a plurality of tiered drip flanges, according to one aspect of the present disclosure. The spike tip 704 comprises a piercing tip 714 defining an aperture 726 that is in fluid communication with a syringe tip coupling adapter 724 configured to fluidly couple to the tip 710 of the syringe (FIGS. 33, 34). The spike tip 704 also comprises a fluid wicking tip 712 comprising a plurality of tiered drip flanges configured to wick fluid by capillary action and to retain spilled fluid between any two tiers of the plurality of tiered drip flanges 722a, 722b, 722c, 722d, 722e, 722f, 722g, 722h by surface tension and capillary action. As shown in FIGS. 35-38, the diameter of the tiered drip flanges 722a-772h decrease from the top tiered drip flange 722a to the bottom tiered drip flange 722h, whereas in other aspects the diameter may increase from the top tiered drip flange to the bottom tiered drip flange. As previously discussed, the space defined between the tiered drip flanges 722a-722h defines a predetermined volume and are configured to wick spilled fluid in those spaces by way of capillary action. Each of the spaces defines a particular volume and can retain or hold a predetermined amount of fluid until a maximum retention volume is reached. The spilled fluid cascades down the tiered drip flanges 722a-722h as the spill volume increases and each of the spaces defined between the tiered drip flanges 722a-722h reaches its maximum retention volume, the fluid flows to the next drip flange. Any excess spill fluid is ultimately caught by the circumferential drip flange 716 on body 706 of the syringe 702 (FIGS. 33-34).

Figure 39:
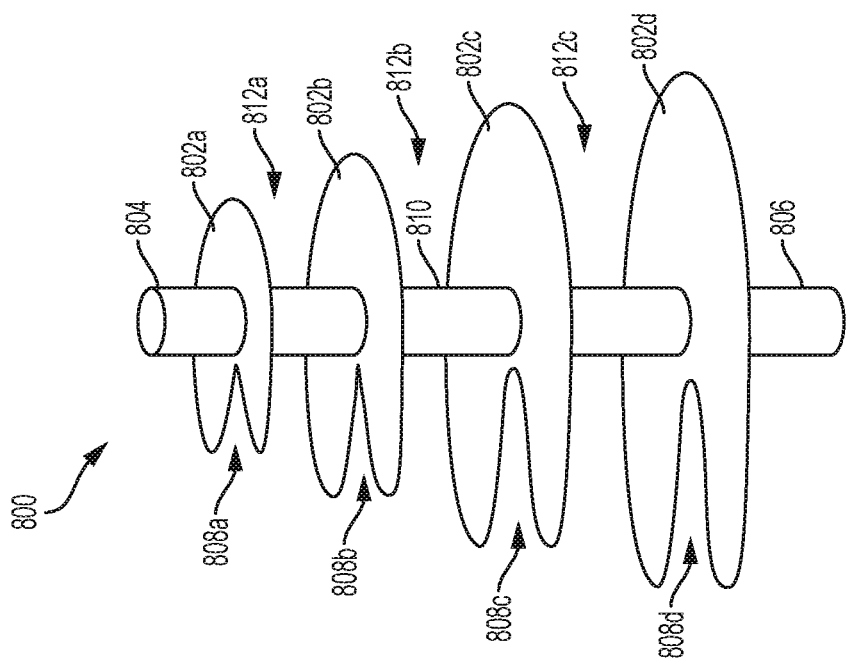
FIG. 39 illustrates a fluid wicking tip comprising a plurality of tiered drip flanges, according to one aspect of the present disclosure.

FIG. 39 illustrates a fluid wicking tip 800 comprising a plurality of tiered drip flanges, according to one aspect of the present disclosure. The fluid wicking tip 800 comprises a plurality of tiered flanges 802a, 802b, 802c, 802d each progressively larger from the top to the bottom. The tiered drip flanges 802a-802d are formed about a channel 810 which fluidly couples a tip 804 with a syringe tip coupling adapter 806. The tip 804 is sized and configured to fluidly couple to a flexible tube assembly. In one aspect, the tip 804 may be a threaded luer fitting. The syringe tip coupling adapter 806 is sized and configured to fluidly couple to a tip of a syringe.

Narrow circumferential spaces 812a, 812b, 812c are defined between the tiered drip flanges 802a-802b, 802b-802c, and 802c-802d. The narrow circumferential spaces 812a-812c define a predetermined unique volume and are configured for wicking fluid by capillary action and for holding or retaining fluid that is wicked in the narrow circumferential spaces 812a-812c. Fluid is wicked in the defined narrow circumferential spaces 812a-812c by capillary action. Once a fluid volume exceeds the maximum retention volume, the fluid flows to a drip flange on a lower tier until all the narrow circumferential spaces 812a-812c are filled with fluid to the maximum retention volume if necessary. The tiered drip flanges 802a-802d each comprise an opening 808a, 808b, 808c, 808d to facilitate draining fluid from an upper drip flange to a lower drip flange. For example, the opening 808a facilitates drainage of from the upper surface of the top tiered drip flange 802a to the lower tiered drip flange 802b. Likewise, the opening 808b facilitates drainage of fluid held in the narrow circumferential space 812a from the upper tiered drip flange 802b to the lower tiered drip flange 802c, and so on. The opening 808d facilitates drainage of fluid held in the narrow circumferential space 812c from the tiered drip flange 802d to a syringe located therebelow. Ideally a drip cup or continuous drip flange may be located below the lowest tiered drip flange 802d to catch excess fluid that drains therefrom. Examples of drip cups that may be adapted to fluid wicking tip 800 are shown in FIGS. 1, 3, 5, 7, 9, 11, and 20-27, for example.

Figure 40:
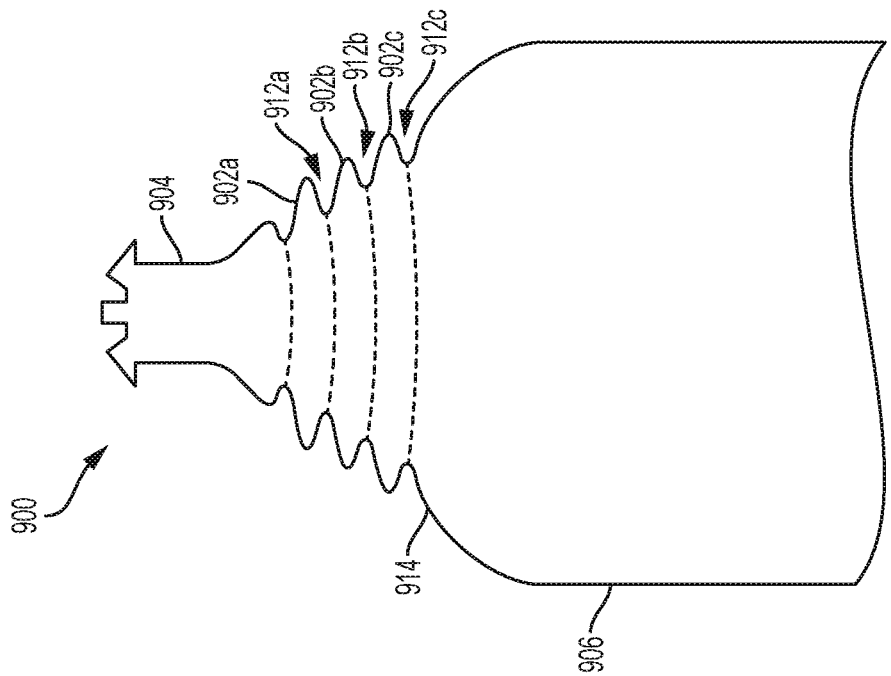
FIG. 40 illustrates a syringe comprising an integrally formed tiered drip flange fluid wicking structure, according to one aspect of the present disclosure.

FIG. 40 illustrates a syringe 900 comprising an integrally formed tiered drip flange fluid wicking structure, according to one aspect of the present disclosure. The syringe 900 comprises a body 906 and a tip 904 sized and configured to fluidly couple to a flexible tube assembly. In one aspect, the tip 904 may be a threaded luer fitting. A plurality of tiered drip flanges 902a, 902b, 902c are formed between the tip 904 and the body 906 of the syringe 900. Narrow circumferential spaces 912a, 912b, 912c are defined between the tiered drip flanges 902a-902c. Fluid is wicked into the narrow circumferential spaces 912a-912c without the assistance of, and in opposition to, external forces like gravity by way of capillary action and retained by surface tension and capillary action. A narrow circumferential space 912a is defined between tiered drip flanges 902a and 902b. A narrow circumferential space 912b is defined between tiered drip flanges 902b and 902c. A narrow circumferential space 912c is defined between tiered drip flange 902c and a tapered portion 914 of the body 906. The narrow circumferential spaces 912a-912c are configured to wick fluid that spills from the tip 904. The fluid is wicked into the spaces 912a-912c by capillary action. The defined narrow circumferential spaces 912a-912c hold a predetermined volume of fluid. When the fluid volume held between a narrow circumferential space 912a-912c exceeds the maximum retention volume, the fluid flows to a lower tier flange until all the narrow circumferential spaces 912a-912c have reached the maximum retention volume.

FIG. 41 illustrates a fluid wicking connector 1000 comprising a plurality of tiered drip flanges arranged to facilitate wicking fluid by capillary action, according to one aspect of the present disclosure. In one aspect, the fluid wicking connector 1000 comprises a body 1006 that defines a fluid channel therethrough. The distal end of the fluid wicking connector 1000 comprises a male threaded luer fitting 1004 sized and configured to fluidly couple to a flexible tube assembly. The proximal end of the fluid wicking connector 1000 comprises a male connector coupling adapter 1008. In one aspect, the connector coupling adapter 1008 may comprise a threaded female 1012 luer fitting sized and configured to fluidly couple to a male luer assembly with a threaded outer receptor. A plurality of tiered drip flanges 1002a, 1002b, 1002c are disposed about the body 1006 of the fluid wicking connector 1000. A narrow circumferential space 1010a is defined between the top tiered drip flange 1002a and the middle tiered drip flange 1002b. A narrow circumferential space 1010b is defined between the middle tiered drip flange 1002b and the bottom drip flange 1002. The narrow circumferential spaces 1010a, 1010b each define a unique fluid retention volume. Fluid that drips from the male threaded luer fitting 1004 runs down the body 1006 of the fluid wicking connector 1000 and collects on a top surface of the top tiered drip flange 1002a. Excess fluid that spills over the sides of the top tiered drip flange 1002a is wicked into the narrow circumferential space 1010a defined between any two tiers of the tiered drip flanges 1002a-1002b by capillary action. Once the circumferential space reaches the maximum retention volume, excess fluid spills over the sides of the middle tiered drip flange 1002b and is wicked into the narrow circumferential space 1010b defined between the tiered drip flanges 1002b-1002c by capillary action. Once the narrow circumferential space 1010b reaches the maximum retention volume, excess fluid spills over the sides of the bottom tiered drip flange 1002c, and so on. The fluid wicking connector 1000 has an interchangeable orientation such that the female threaded luer fitting 1012 can be fluidly coupled to a male luer connector, such as a tip of a syringe or male end of a flexible tube assembly, and male coupling adapter 1004 can be fluidly coupled to a female luer fitting on a flexible tube assembly or spike.

Figure 43:
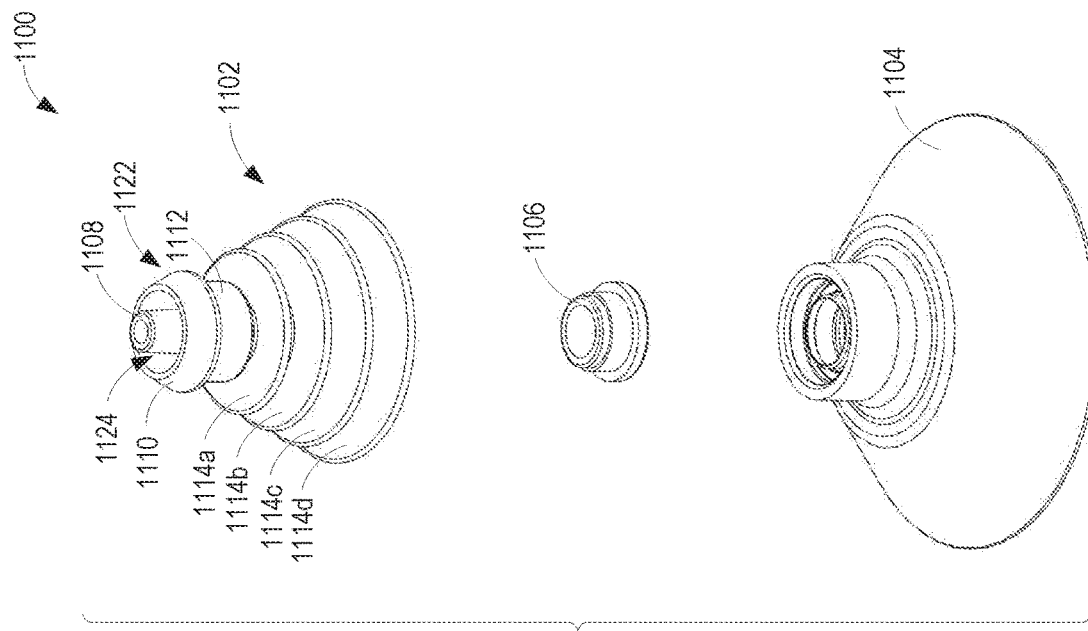
FIG. 43 is an exploded view of the fluid wicking assembly shown in FIG. 42, according to one aspect of the present disclosure.
Figure 42:
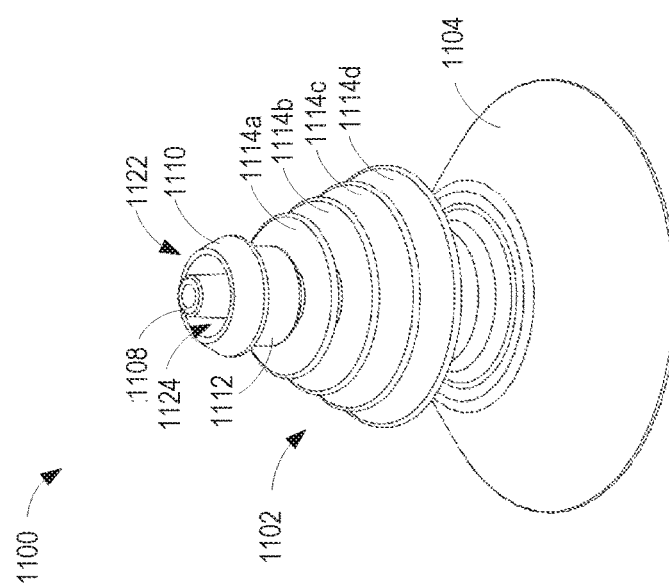
FIG. 42 is a perspective view of a fluid wicking assembly comprising a fluid wicking tip, a diverter, and a neck, according to one aspect of the present disclosure.

FIGS. 42-46 illustrate a fluid wicking assembly 1100 comprising a fluid wicking tip 1102, a flow diverter 1106, and a neck 1104, according to aspect of the present disclosure. FIG. 42 is a perspective view of the fluid wicking assembly 1100 comprising a fluid wicking tip 1102 comprising a plurality of tiered drip flanges arranged to facilitate wicking fluid by way of capillary action. FIG. 43 is an exploded view of the fluid wicking assembly 1100 shown in FIG. 42. With reference to FIGS. 42-43, in one aspect, the fluid wicking assembly 1100 comprises a fluid wicking tip 1102, a neck 1104, and a flow diverter 1106. The fluid wicking tip 1102 comprises a distal tip 1108 sized, configured, and adapted to fluidly couple to a flexible tubing assembly. The fluid wicking tip 1102 also comprises a connector tip 1122 comprising a tapered surface 1110 and a cylindrical body 1112. The connector tip 1122 defines an opening 1124 for retaining some of the spilled fluid. Below the connector tip 1122, the fluid wicking tip 1102 comprises a plurality of tiered drip flanges 1114a, 1114b, 1114c, 1114c each having a progressively larger diameter according to their distal to proximal position. As shown in FIG. 43, the flow diverter 1106 is configured to attach to the fluid wicking tip 1102 and to seat within the neck 1104 The neck 1104 may be attached to a distal end of a syringe, for example by adhesion or laser welding, or may be integrally molded as part of a distal end of a syringe assembly.

Figure 45:
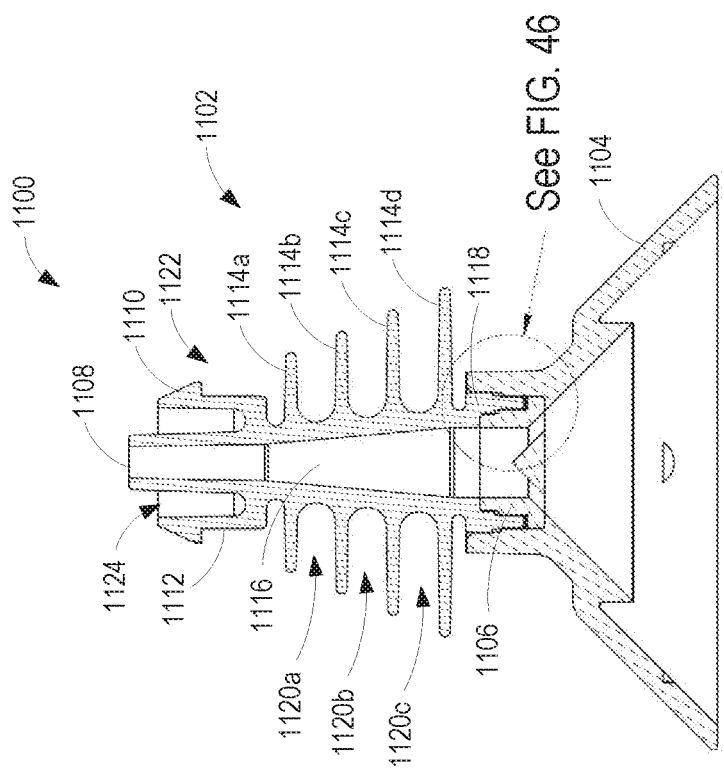
FIG. 45 is a sectional view of the fluid wicking assembly taken along section line 45-45 as shown in FIG. 44, according to one aspect of the present disclosure.
Figure 44:
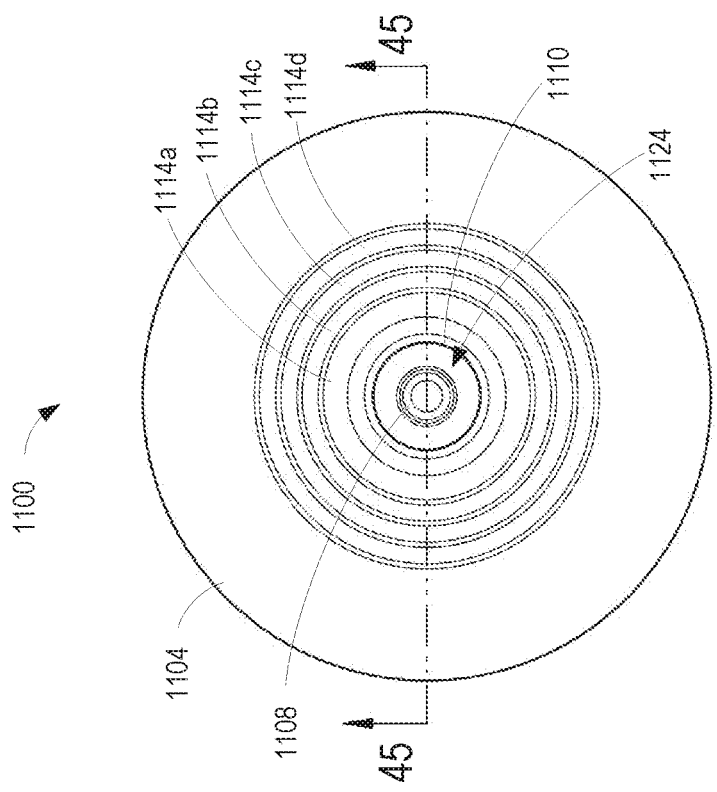
FIG. 44 is a top view of the fluid wicking assembly shown in FIG. 42, according to one aspect of the present disclosure.

FIG. 44 is a top view of the fluid wicking assembly 1100 shown in FIG. 42 and FIG. 45 is a sectional view of the fluid wicking assembly 1100 taken along section line 45-45 as shown in FIG. 44. FIG. 45 illustrates the three components of the fluid wicking assembly 1100 in an assembled state. As shown, the flow diverter 1106 is coupled to the fluid wicking tip 1102 and the neck 1104 such that the flow diverter 1106 is seated within a distal portion of the neck 1104. The fluid wicking tip 1102 comprises a body 1118 that defines a channel 1116 therethrough. The channel 1116 provides for fluid communication between the distal tip 1108 and the neck 1104, which is adapted and configured to couple to a syringe. Still with reference to FIG. 45, the tiered drip flanges 1114a-1114d define narrow circumferential spaces 1120a, 1120b, 1120c for wicking fluid therein without the assistance of, and in opposition to, external forces like gravity.

Figure 46:
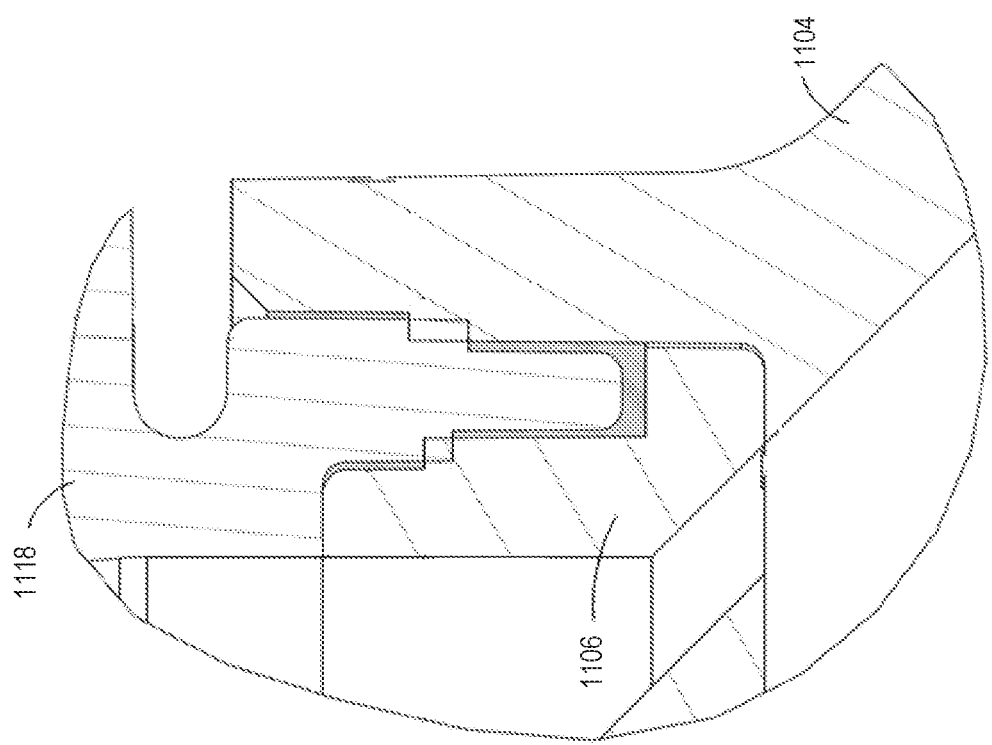
FIG. 46 is a detail view of a weld interface between a body of a fluid wicking tip, a diverter, and a neck, according to one aspect of the present disclosure.

FIG. 46 is a detail view of a weld or adhesive interface between the body 1118 of the fluid wicking tip 1102, the neck 1104, and the flow diverter 1106, according to one aspect of the present disclosure.

FIGS. 47-51 illustrate a fluid wicking assembly 1200 comprising a fluid wicking tip 1202, a diverter 1206, and a female luer adapter 1204, according to aspect of the present disclosure. FIG. 47 is a perspective view of a fluid wicking tip 1202 comprising a fluid wicking tip 1102, a diverter 1206, and a female luer adapter 1204. The fluid wicking tip 1202 comprises a plurality of tiered drip flanges arranged to facilitate wicking fluid by way of capillary action. FIG. 48 is an exploded view of the fluid wicking assembly 1200 shown in FIG. 47. With reference to FIGS. 47-48, in one aspect, the fluid wicking assembly 1200 comprises a fluid wicking tip 1202, a female luer adapter 1204, and a diverter 1206. The fluid wicking tip 1202 comprises a distal tip 1208 sized, configured, and adapted to fluidly couple to a flexible tubing assembly. The fluid wicking tip 1202 also comprises a connector tip 1222 comprising a tapered surface 1210 and a cylindrical body 1212. The connector tip 1222 defines an opening 1224 for retaining some of the spilled fluid. Below the connector tip 1222, the fluid wicking tip 1202 comprises a plurality of tiered drip flanges 1214a, 1214b, 1214c, 1214c each having a progressively larger diameter according to their distal to proximal position. As shown in FIG. 48, the diverter 1206 is configured to attach to the fluid wicking tip 1202 and to seat within the luer adapter 1204.

Figure 50:
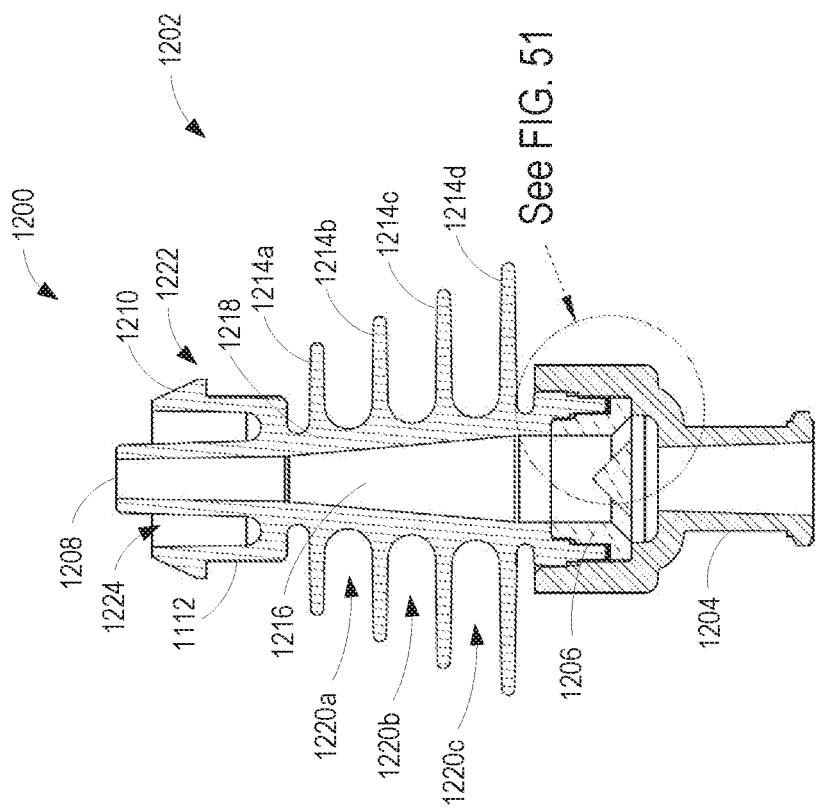
FIG. 50 is a sectional view of the fluid wicking assembly shown in FIG. 47 taken along section line 50-50 shown in FIG. 49, according to an aspect of the present disclosure.
Figure 49:
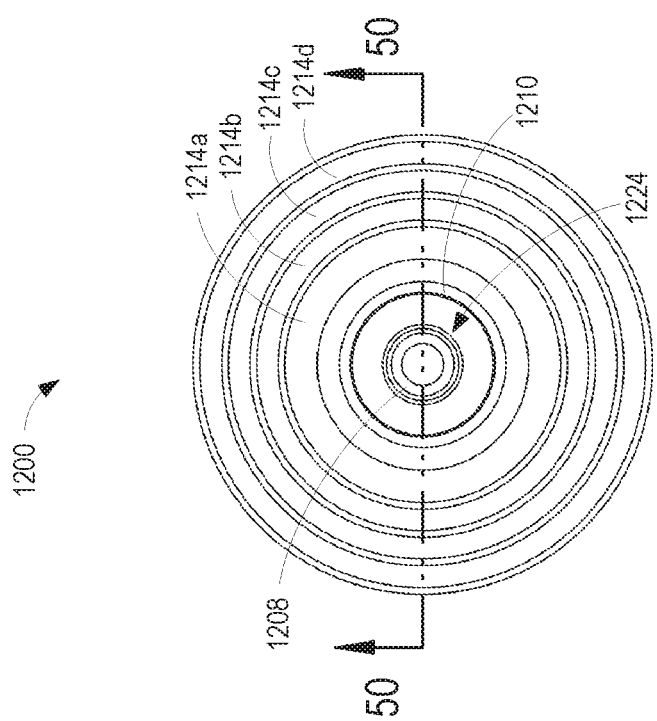
FIG. 49 is a top view of the fluid wicking assembly shown in FIG. 47, according to one aspect of the present disclosure.

FIG. 49 is a top view of the fluid wicking assembly 1200 shown in FIG. 47 and FIG. 50 is a sectional view of the fluid wicking assembly 1200 shown in FIG. 47 taken along section line 50-50 as shown in FIG. 49. FIG. 50 illustrates the three components of the fluid wicking assembly 1200 in an assembled state. As shown, the diverter 1206 is coupled to the fluid wicking tip 1202 and the luer adapter 1204 such that the diverter 1206 is seated within a distal portion of the luer adapter 1204. The fluid wicking tip 1202 comprises a body 1218 that defines a channel 1216 therethrough. The channel 1216 provides for fluid communication between the distal tip 1208 and the luer adapter 1204, which is adapted and configured to couple to a syringe. Still with reference to FIG. 50, the tiered drip flanges 1214a-1214d define narrow circumferential spaces 1220a, 1220b, 1220c for wicking fluid therein without the assistance of, and in opposition to, external forces like gravity.

Figure 51:
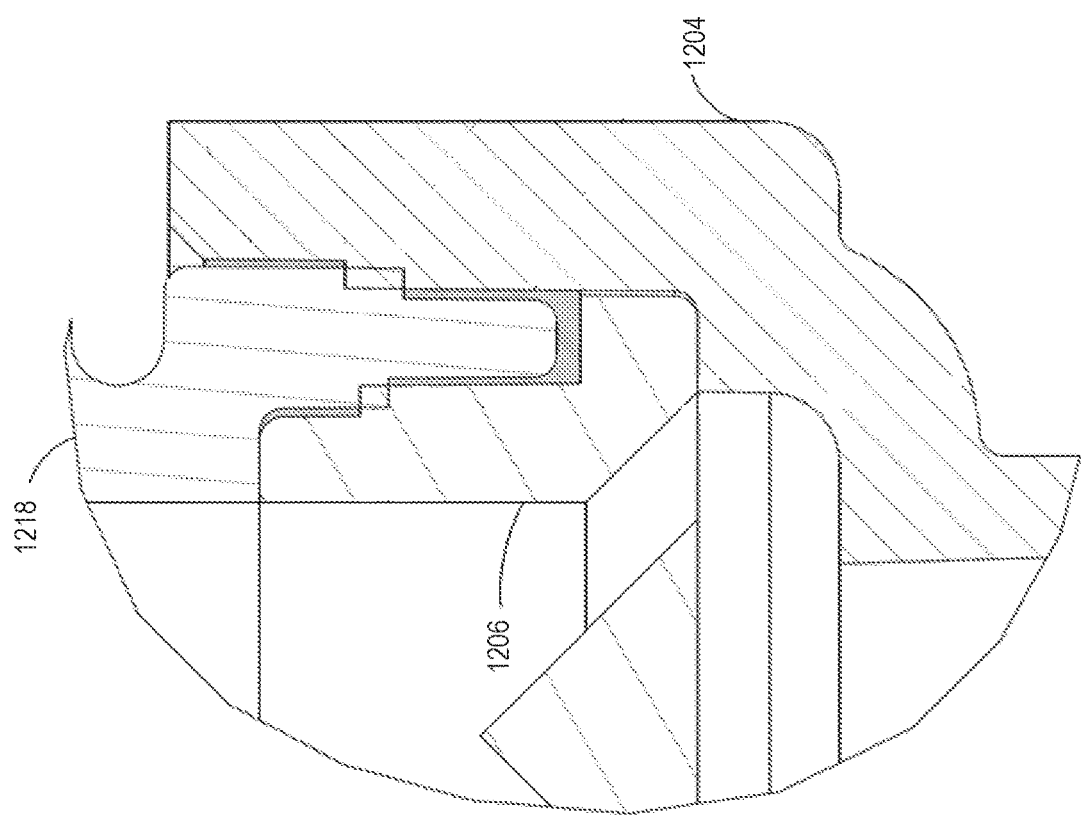
FIG. 51 is a detail view of a weld interface of the fluid wicking tip assembly shown in FIG. 47 between the body of the fluid wicking tip, the luer adapter, and the diverter as depicted in the sectional view shown in FIG. 50.

FIG. 51 is a detail view of a weld or adhesive interface of the fluid wicking assembly 1200 shown in FIG. 47 between the body 1218 of the fluid wicking tip 1202, the luer adapter 1204, and the diverter 1206 as depicted in the sectional view shown in FIG. 50.

Figure 52:
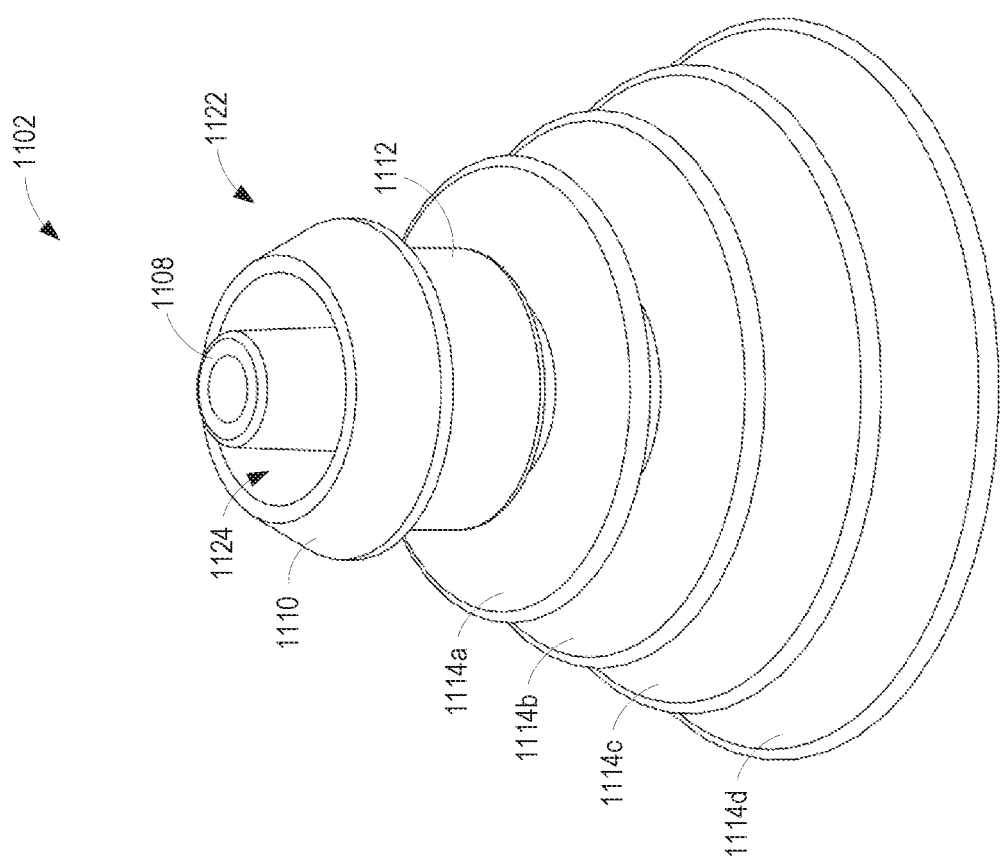
FIG. 52 is a perspective view of the fluid wicking tip, according to one aspect of the present disclosure.

FIGS. 52-56 are detailed views of the fluid wicking tip 1102 shown in FIGS. 42-46 and the fluid wicking assembly 1200 shown in FIGS. 47-51, according to one aspect of the present disclosure. For clarity of disclosure, the detailed view of the fluid wicking tip 1102 shown in FIGS. 52-56 will be described using the reference numbers associated with FIGS. 42-46. Accordingly, FIG. 52 is a perspective view of the fluid wicking tip 1102, according to one aspect of the present disclosure.

Figure 53:
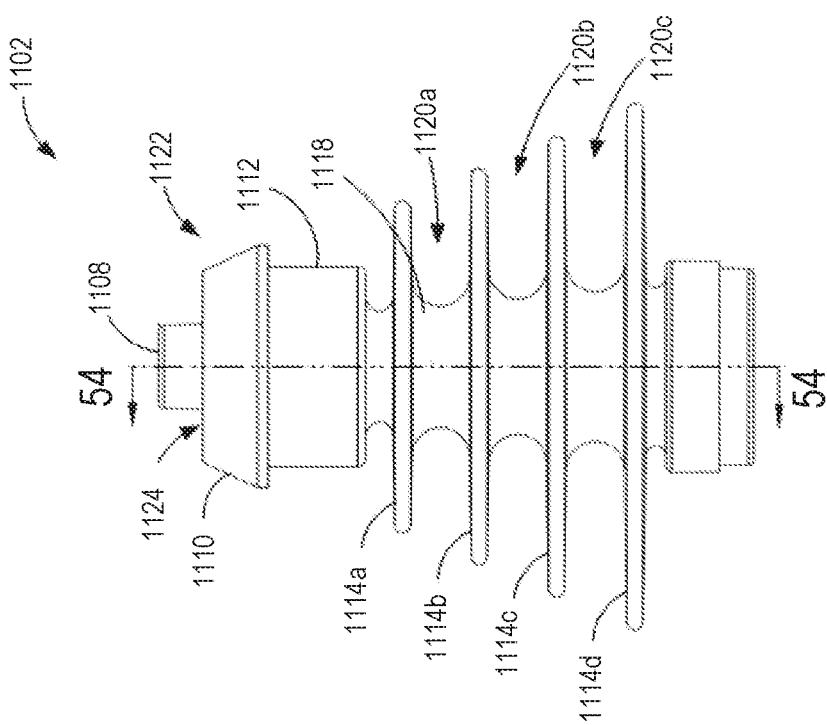
FIG. 53 is a side view of the fluid wicking shown in FIG. 52, according to one aspect of the present disclosure.

FIG. 53 is a side view of the fluid wicking tip 1102 shown in FIG. 52, according to one aspect of the present disclosure.

Figure 54:
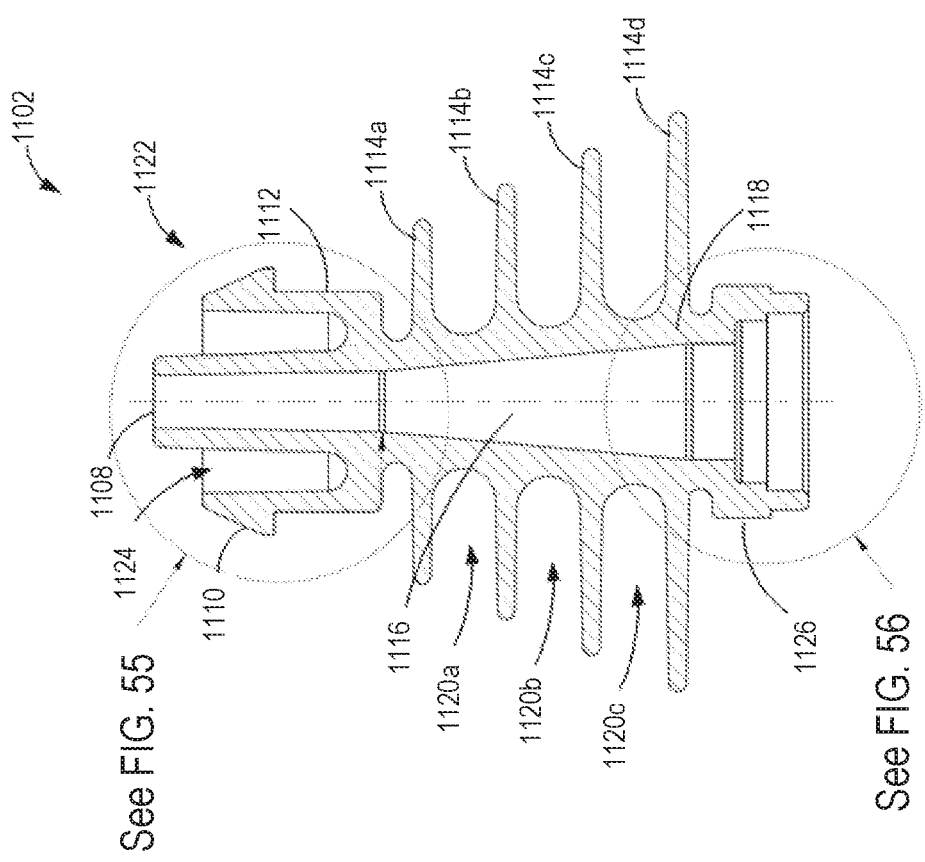
FIG. 54 is a sectional view of the fluid wicking tip shown in FIG. 52 taken along section line 54-54 as shown in FIG. 53.

FIG. 54 is a sectional view of the fluid wicking tip 1102 shown in FIG. 52 taken along section line 54-54 as shown in FIG. 53.

Figure 55:
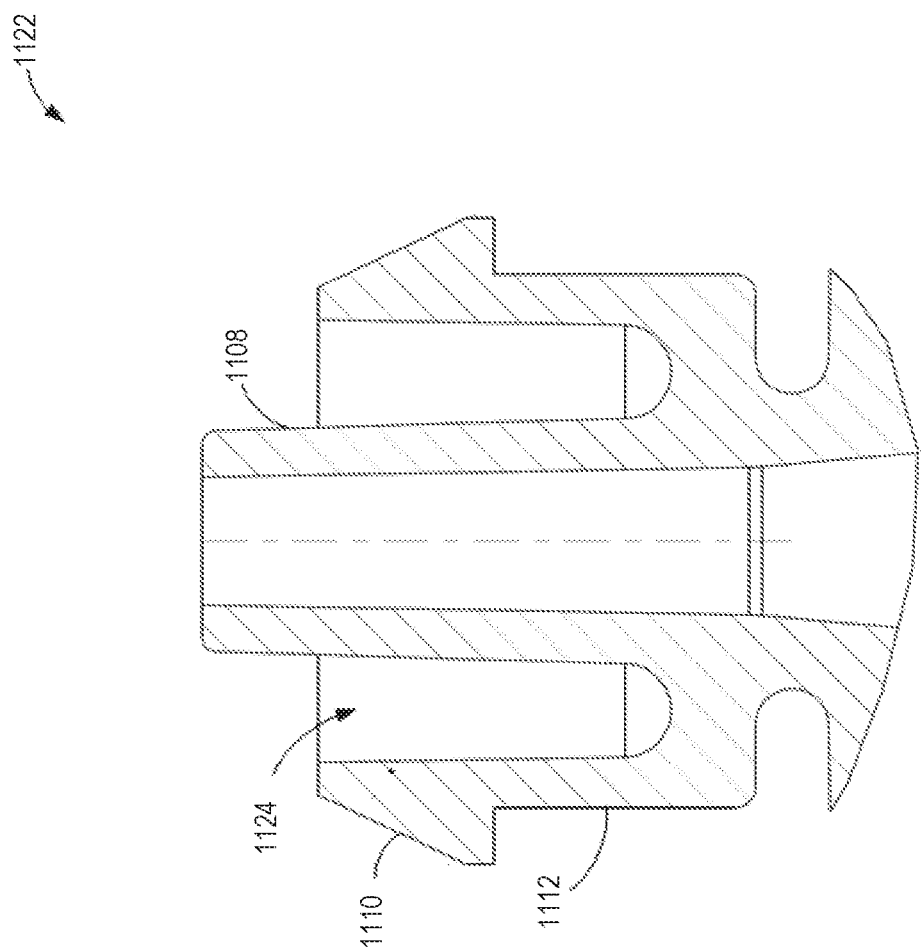
FIG. 55 is a detailed sectional view of the drip cup shown in FIG. 54, according to one aspect of the present disclosure.

FIG. 55 is a detailed sectional view of the connector tip 1122 shown in FIG. 54, according to one aspect of the present disclosure.

Figure 56:
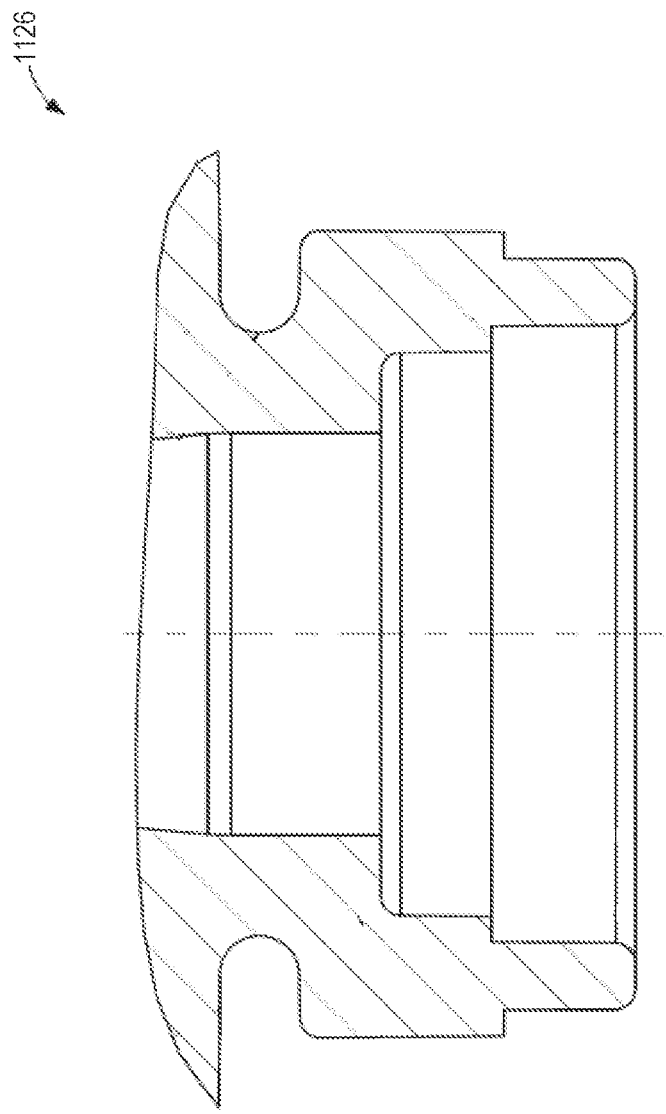
FIG. 56 is a detailed sectional view of the interface adapter shown in FIG. 54, according to one aspect of the present disclosure.

FIG. 56 is a detailed sectional view of the interface adapter 1126 shown in FIG. 54, according to one aspect of the present disclosure. The interface adapter 1126 is sized and configured to couple to the flow diverter 1106 and the neck 1104 shown in FIGS. 43, 45, and 45 or to couple to diverter 1206 and luer adapter 1204 shown in FIGS. 48, 50, and 51.

Figure 57:
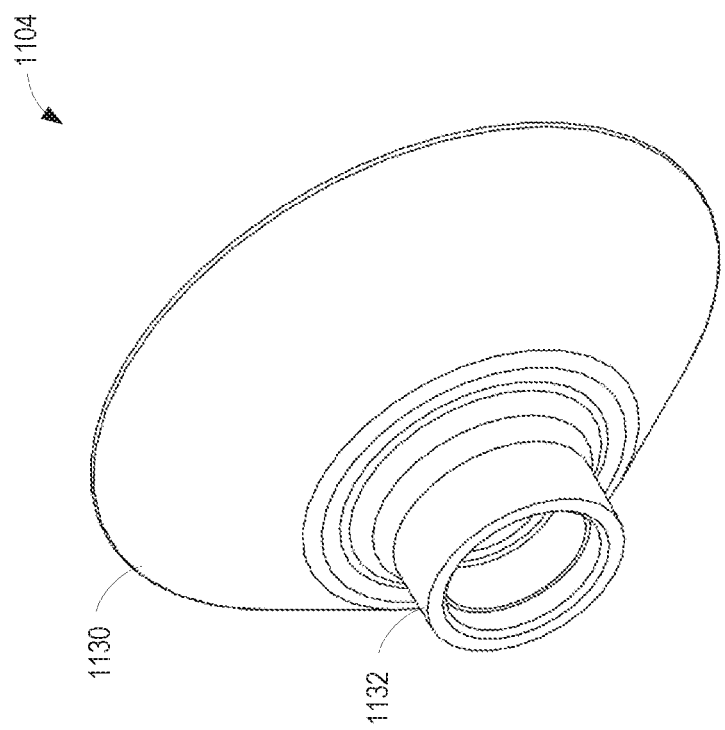
FIG. 57 is a perspective view of the neck component of the fluid wicking assembly shown in FIGS. 42-46, according to one aspect of the present disclosure.

FIGS. 57-62 are detailed views of the neck 1104 component of the fluid wicking assembly 1100 shown in FIGS. 42-46, according to one aspect of the present disclosure. FIG. 57 is a perspective view of the neck 1104 component of the fluid wicking assembly 1100 shown in FIGS. 42-46, according to one aspect of the present disclosure. The neck 1104 comprises a tapered portion 1130 and a cylindrical adapter portion 1132 to couple to the interface adapter 1126 of the fluid wicking assembly 1100 shown in FIG. 56.

Figure 58:
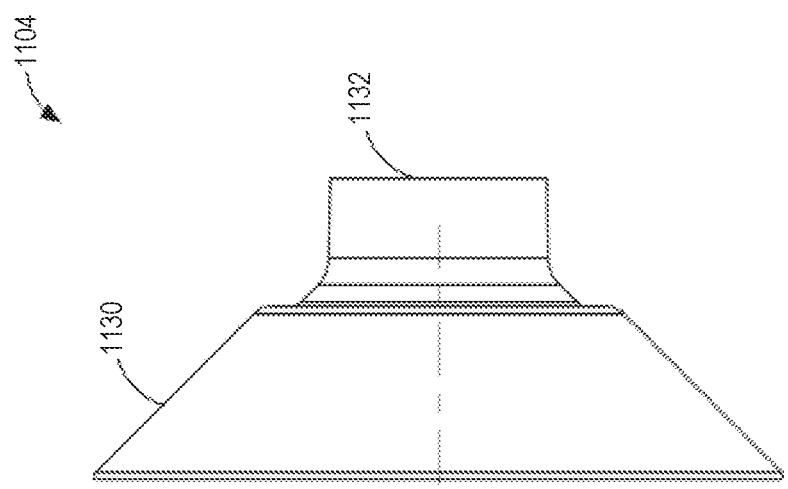
FIG. 58 is a side view of the neck component shown in FIG. 57, according to one aspect of the present disclosure.

FIG. 58 is a side view of the neck 1104 component shown in FIG. 57, according to one aspect of the present disclosure.

Figure 59:
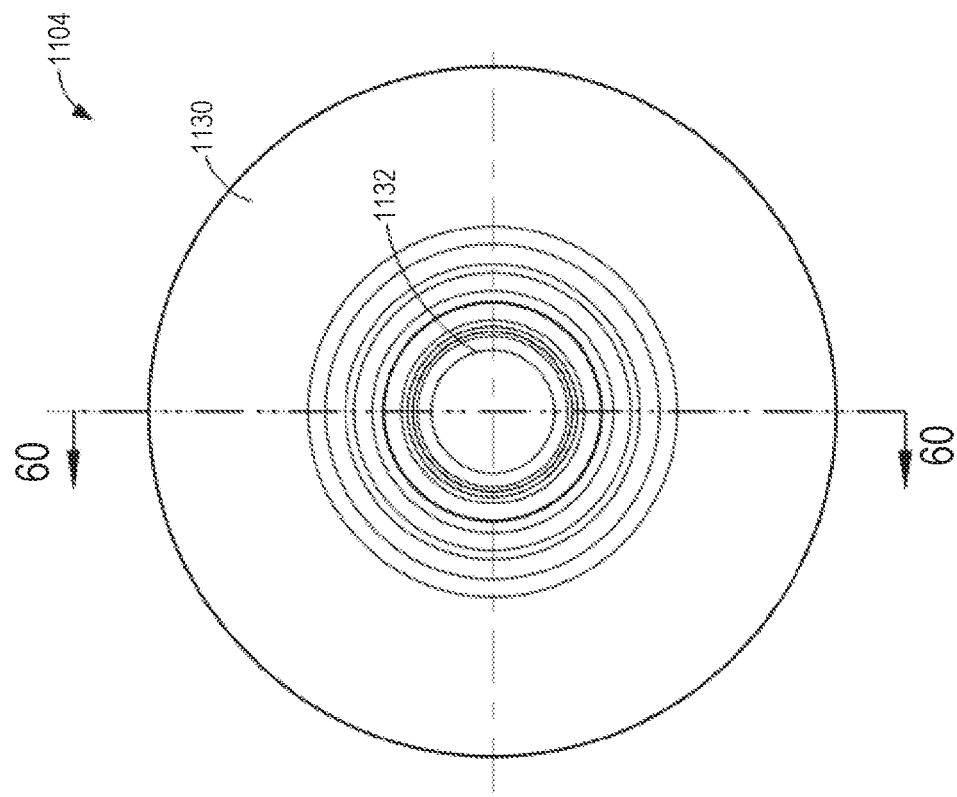
FIG. 59 is a top view of the neck component shown in FIG. 57, according to one aspect of the present disclosure.

FIG. 59 is a top view of the neck 1104 component shown in FIG. 57, according to one aspect of the present disclosure.

Figure 60:
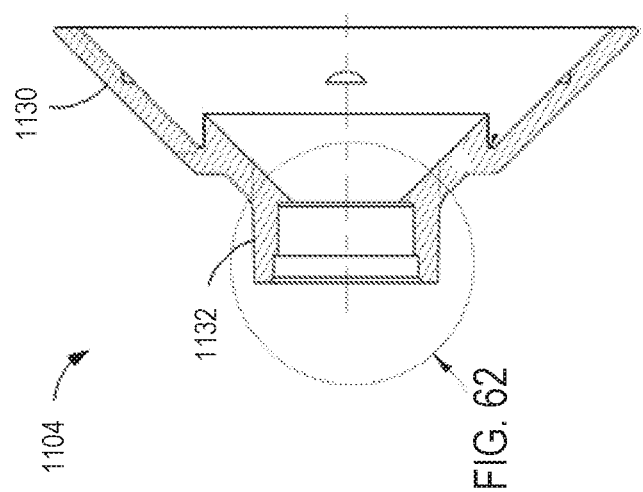
FIG. 60 is a section view of the neck component shown in FIG. 57 taken along section line 60-60 as shown in FIG. 59.

FIG. 60 is a section view of the neck 1104 component shown in FIG. 57 taken along section line 60-60 as shown in FIG. 59.

Figure 61:
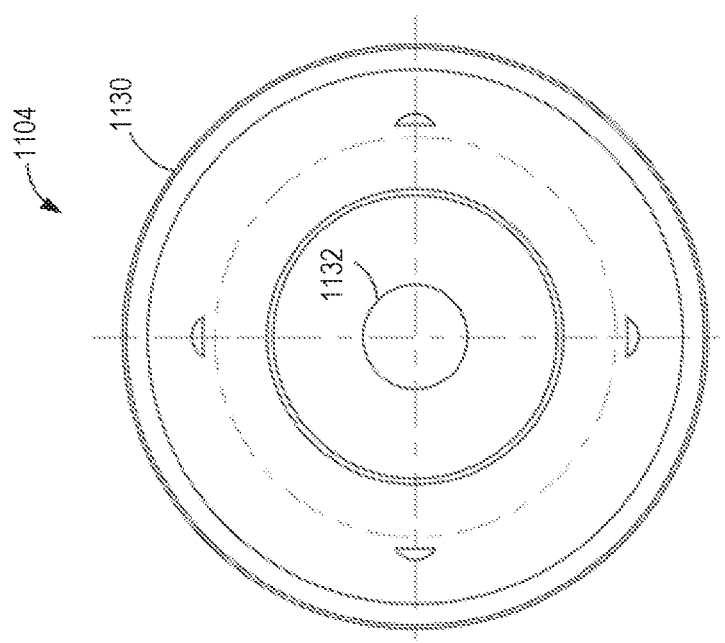
FIG. 61 is a top view of the neck component shown in FIG. 57, according to one aspect of the present disclosure.

FIG. 61 is a top view of the neck 1104 component shown in FIG. 57, according to one aspect of the present disclosure.

Figure 62:
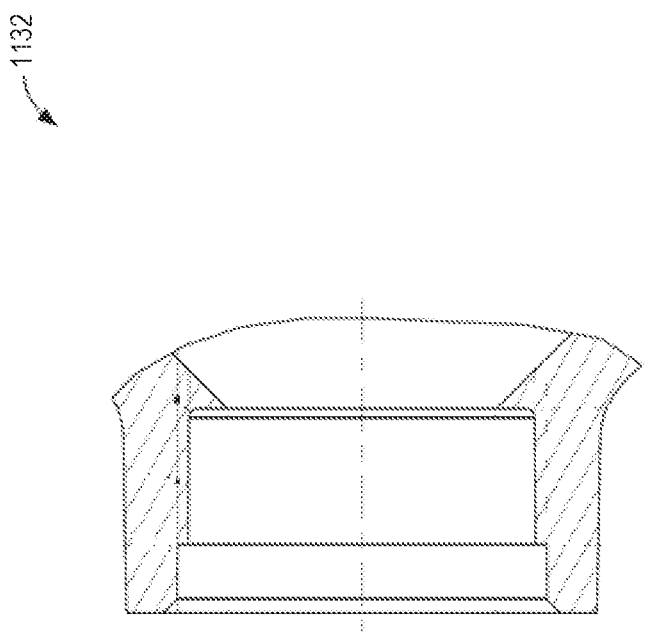
FIG. 62 is a detailed section view of the cylindrical adapter portion of the neck component shown in FIG. 57, according to one aspect of the present disclosure.

FIG. 62 is a detailed section view of the cylindrical adapter portion 1132 of the neck 1104 component shown in FIG. 57, according to one aspect of the present disclosure.

Figure 63:
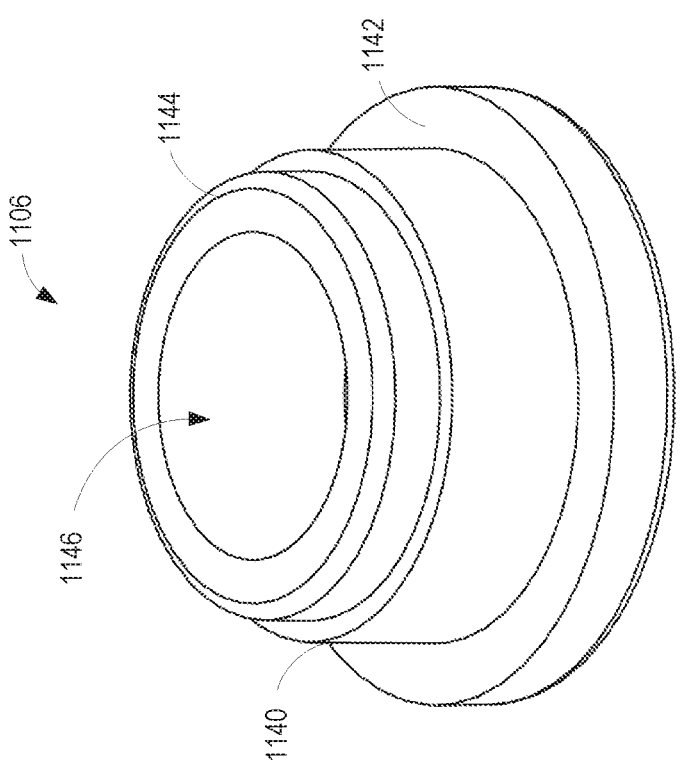
FIG. 63 is a perspective view of the diverter component shown in FIG. 43, according to one aspect of the present disclosure.

FIGS. 63-68 are detailed views of the flow diverter 1106 component shown in FIGS. 43, 45, and 45 and the diverter 1206 component shown in FIGS. 48, 50, 51, according to one aspect of the present disclosure. FIG. 63 is a perspective view of the flow diverter 1106 component shown in FIG. 43, according to one aspect of the present disclosure. The flow diverter 1106 component comprises a base portion 1142 that is sized and configured to seat within the neck 1104 as shown in FIG. 45 or the luer adapter 1204 as shown in FIG. 50. The flow diverter 1106 comprises a cylindrical wall 1140 and a rim 1144 configured to interface with the fluid wicking tip 1102 shown in FIG. 45 or the fluid wicking tip 1202 shown in FIG. 50. The diverter also defines an aperture 1146 to fluidly couple the fluid wicking tip 1102, 1202 with the either the neck 1104 or the luer adapter 1204. The flow diverter 1106 uses the Coanda effect to fill the syringe with fluid and minimize introduction of air bubbles.

Figure 64:
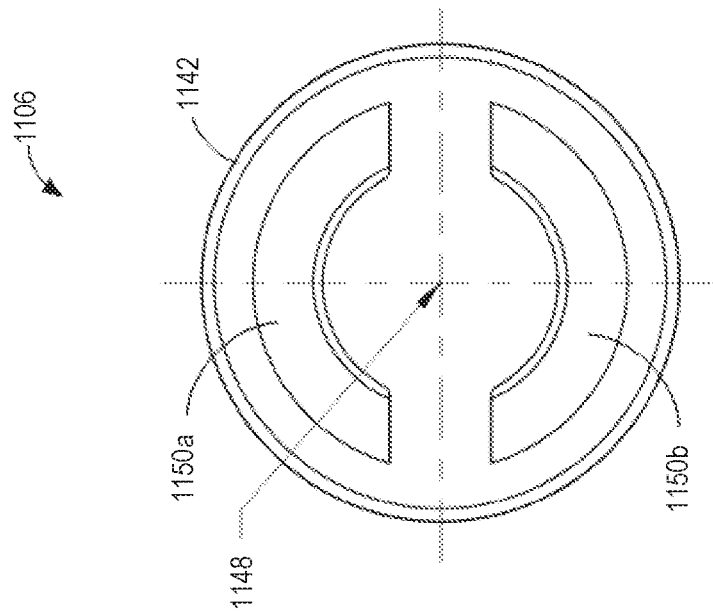
FIG. 64 is a bottom view of the diverter component shown in FIG. 63, according to one aspect of the present disclosure.

FIG. 64 is a bottom view of the flow diverter 1106 component shown in FIG. 63, according to one aspect of the present disclosure. The flow diverter 1106 comprises a diverter block 1148 and defines two diverter channels 1150a, 1150b in fluid communication with the aperture 1146 shown in FIG. 63.

FIG. 65 is a top view of the flow diverter 1106 component shown in FIG. 63, according to one aspect of the present disclosure. The view in FIG. 65 shows the two diverter channels 1150a, 1150b. The diverter block 1148 diverts fluid flow into the two diverter channels 1150a, 1150b. In this manner the fluid is diverted through the diverter channels 1150a, 1150b to fill the syringe with fluid using the Coanda effect, which is the tendency of a fluid jet to be attracted to a nearby surface. Introducing fluid in the syringe in this manner minimizes the introduction of air bubbles into the fluid.

FIG. 66 is a sectional view of flow diverter 1106 component shown in FIG. 63 taken along section line 66-66 shown in FIG. 65, according to an aspect of the present disclosure.

Figure 67:
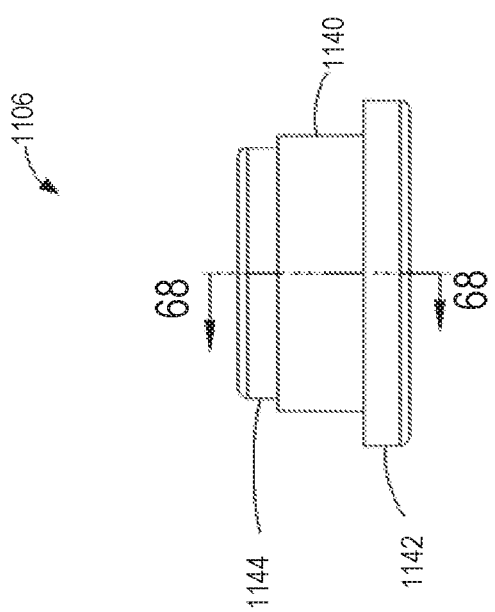
FIG. 67 is a side view of the diverter component shown in FIG. 63, according to one aspect of the present disclosure.

FIG. 67 is a side view of the flow diverter 1106 component shown in FIG. 63, according to one aspect of the present disclosure.

Figure 68:
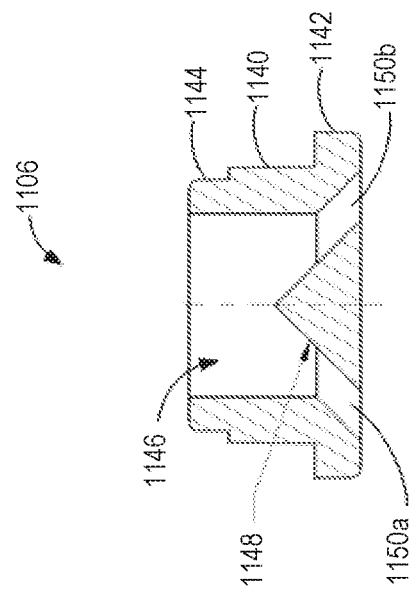
FIG. 68 is a section view of the diverter component shown in FIG. 63 taken along section line 68-68 as shown in FIG. 67.

FIG. 68 is a section view of the flow diverter 1106 component shown in FIG. 63 taken along section line 68-68 as shown in FIG. 67. FIG. 68 shows the diverter block 1148 and the two diverter channels 1150a, 1150b in fluid communication with the aperture 1146.

Figure 69:
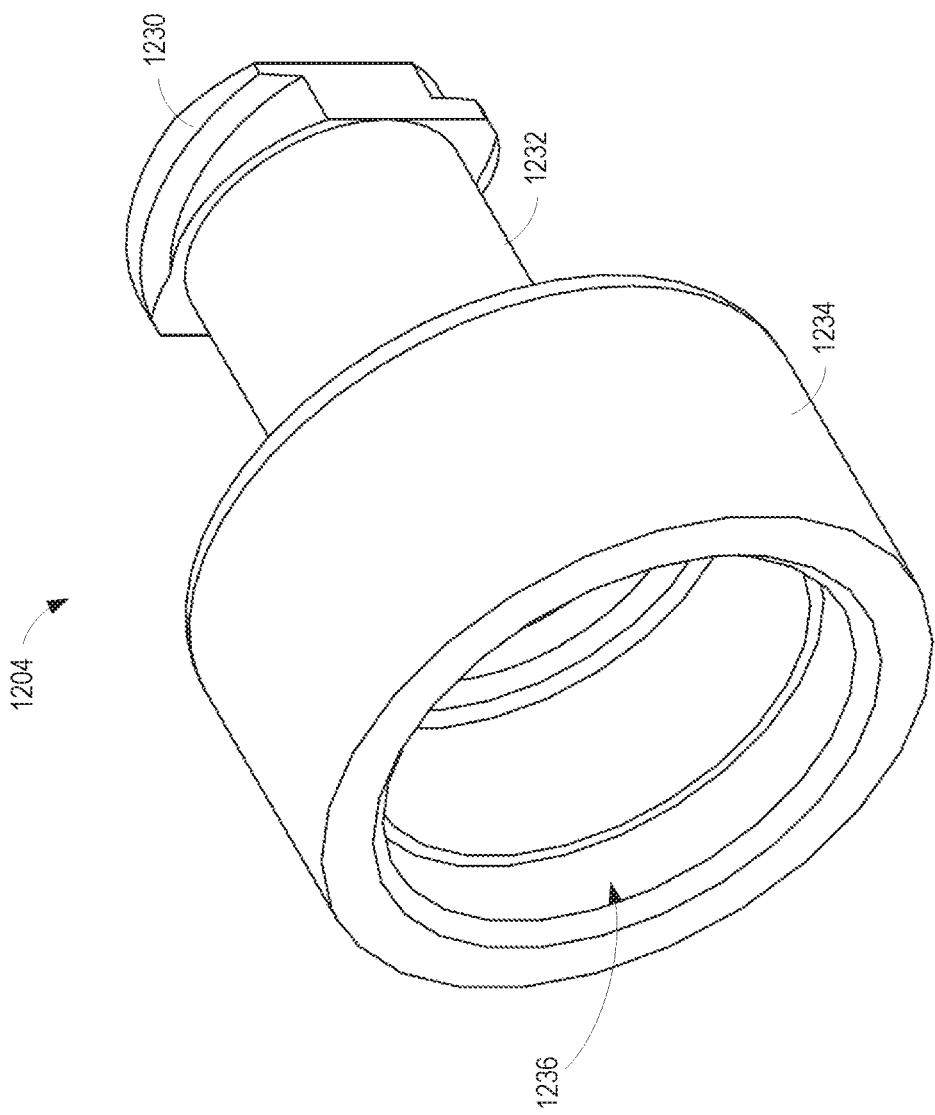
FIG. 69 is a perspective view of the luer adapter component shown in FIG. 48, according to one aspect of the present disclosure.

FIGS. 69-73 are detailed views of the luer adapter 1204 component shown in FIGS. 48 and 50, according to one aspect of the present disclosure. FIG. 69 is a perspective view of the luer adapter 1204 component shown in FIG. 48, according to one aspect of the present disclosure. In one aspect, the luer adapter 1204 comprises a threaded luer fitting 1230 and a stem section 1232 connecting the threaded luer fitting 1230 with an interface portion 1234 defining an aperture 1236. The interface portion 1234 is sized and configured to fluidly couple with the fluid wicking tip 1202 shown in FIGS. 48 and 50.

Figure 70:
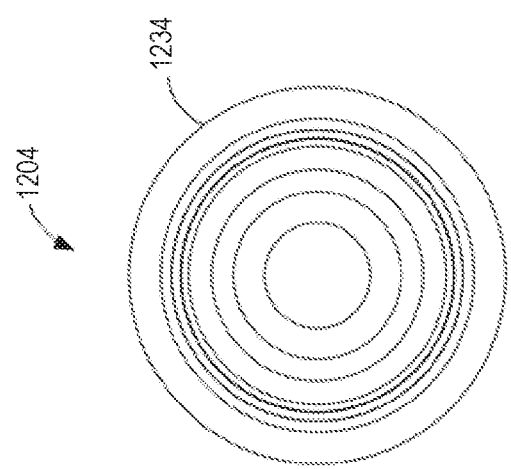
FIG. 70 is a top view of the luer adapter component shown in FIG. 69, according to one aspect of the present disclosure.

FIG. 70 is a top view of the luer adapter 1204 component shown in FIG. 69, according to ne aspect of the present disclosure.

Figure 71:
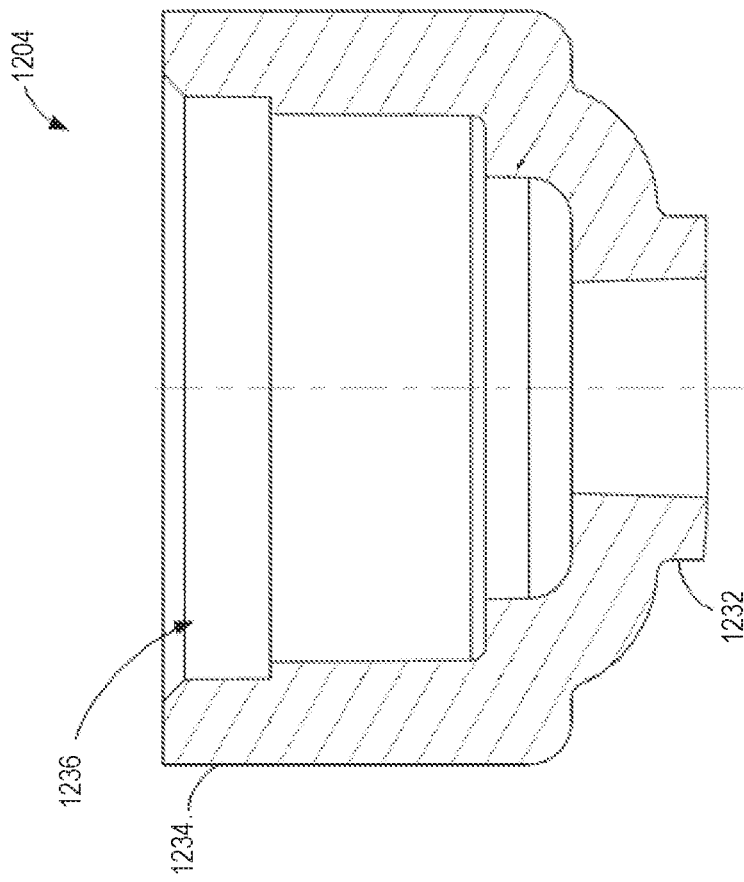
FIG. 71 is a detailed section view of the interface portion of the luer adapter component shown in FIG. 69 and the section view shown in FIG. 73 taken along section line 73-73 as shown in FIG. 72, according to one aspect of the present disclosure.
Figure 73:
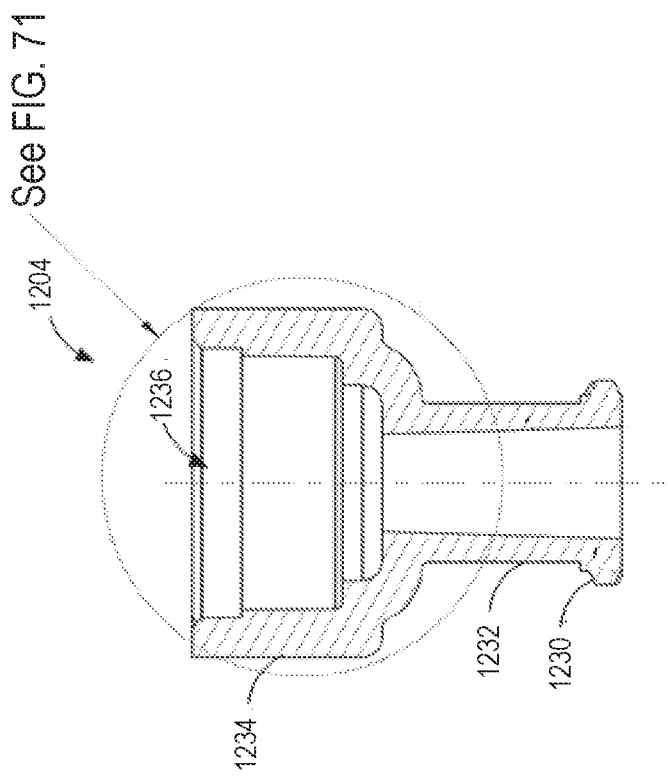
FIG. 73 is section view of the luer adapter component shown in FIG. 69 taken along section line 73-73 shown in FIG. 72, according to an aspect of the present disclosure.
Figure 72:
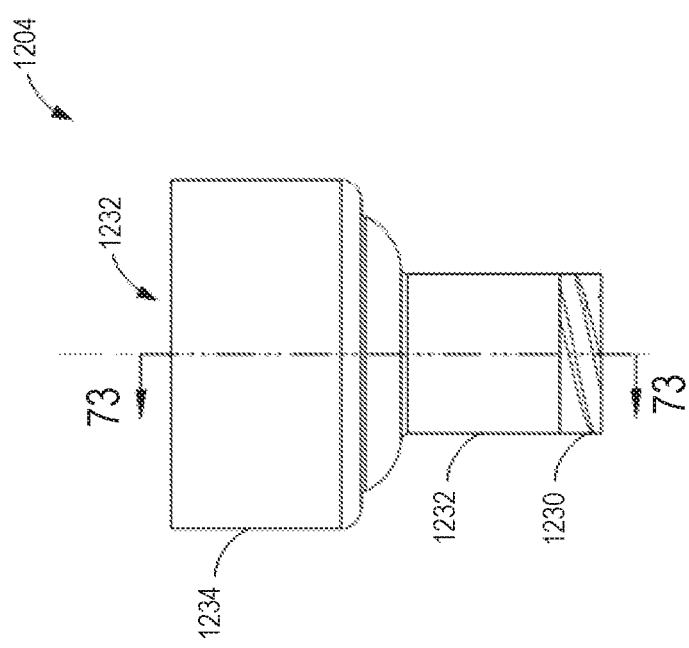
FIG. 72 is a side view of the luer adapter component shown in FIG. 69, according to one aspect of the present disclosure.

FIG. 71 is a detailed section view of the interface portion 1234 of the luer adapter 1204 component shown in FIG. 69 and the section view shown in FIG. 73 taken along section line 73-73 as shown in FIG. 72, according to one aspect of the present disclosure.

FIG. 72 is a side view of the luer adapter 1204 component shown in FIG. 69, according to one aspect of the present disclosure.

FIG. 73 is section view of the luer adapter 1204 component shown in FIG. 69 taken along section line 73-73 shown in FIG. 72, according to an aspect of the present disclosure.

Figure 74:
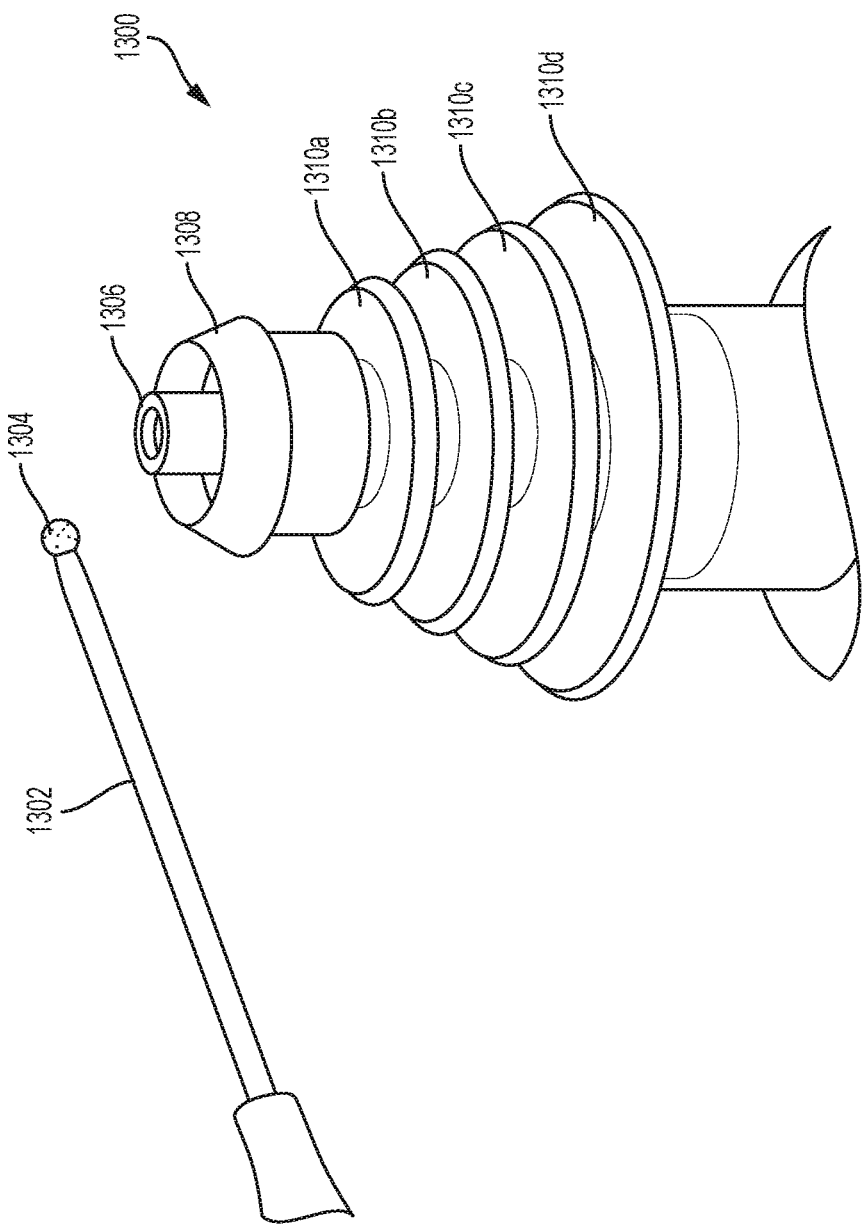
FIGS. 74-79 are a sequential set of frames illustrating a fluid wicking tip 1300 in the process of wicking fluid, in accordance with the present disclosure, where.

FIGS. 74-79 is a sequential set of frames illustrating a fluid wicking tip 1300 in the process of wicking fluid, in accordance with the present disclosure. FIG. 74 is the first frame of the sequence illustrating a pipette 1302 filled with a fluid 1304 to be dropped onto the fluid wicking tip 1300, according to one aspect of the present disclosure. The fluid wicking tip 1300 comprises a distal tip 1306, a drip cup 1308, and a plurality of tiered drip flanges 1310a, 1310b, 1310c, and 1310d. As described herein, the narrow circumferential spaces formed between any two of the tiered drip flanges 1310a-1310d wick the fluid 1304 without the assistance of, and in opposition to, external forces like gravity by way of capillary action as shown in the subsequent illustrations. In FIG. 74, no fluid 1304 has yet been dropped on the fluid wicking tip 1300.

Figure 75:
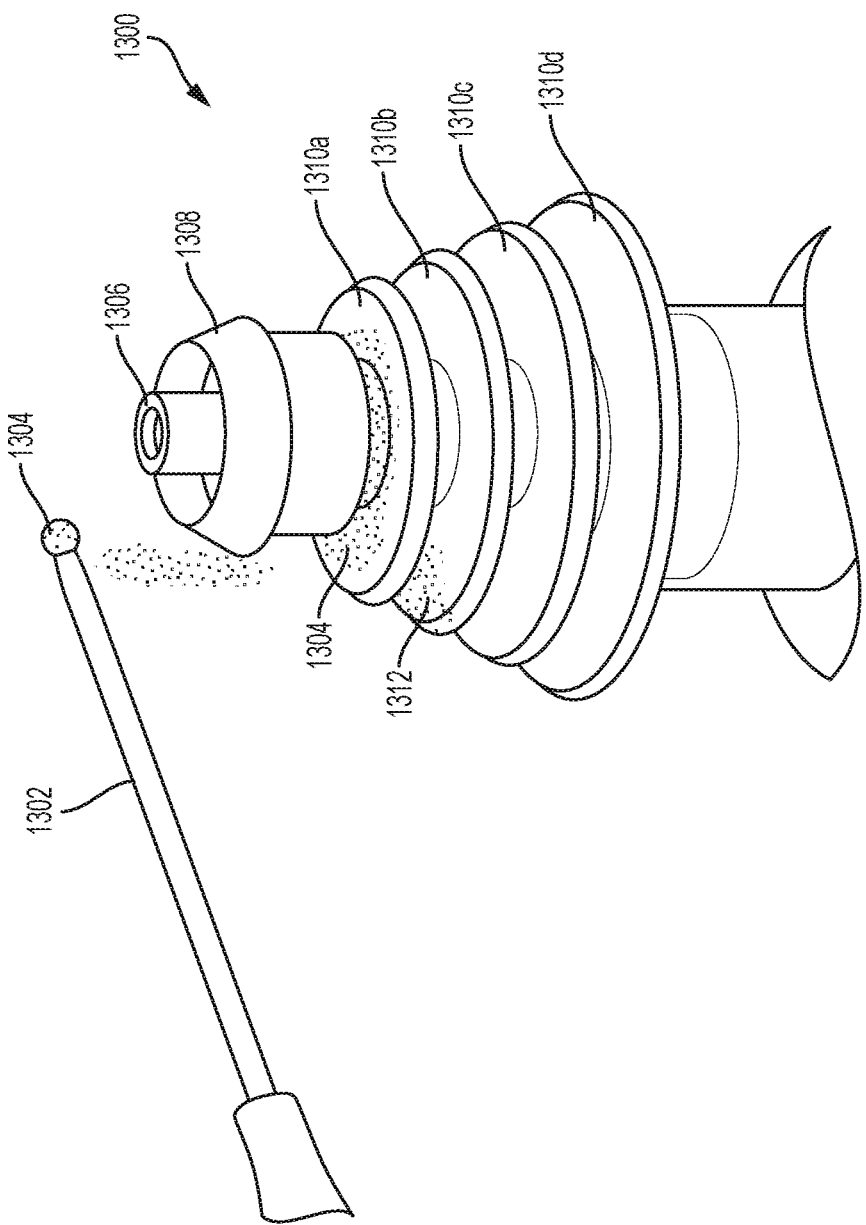

FIG. 75 is the second frame of the sequence after several drops of fluid 1304 have been dropped onto the fluid wicking tip 1300, according to one aspect of the present disclosure. As shown, the fluid 1304 has begun to accumulate on the surface of the top tiered drip flange 1310a with some fluid 1304 landing in the drip cup 1308 and one drop 1312 landing on the surface of the second tiered drip flange 1310b.

Figure 76:
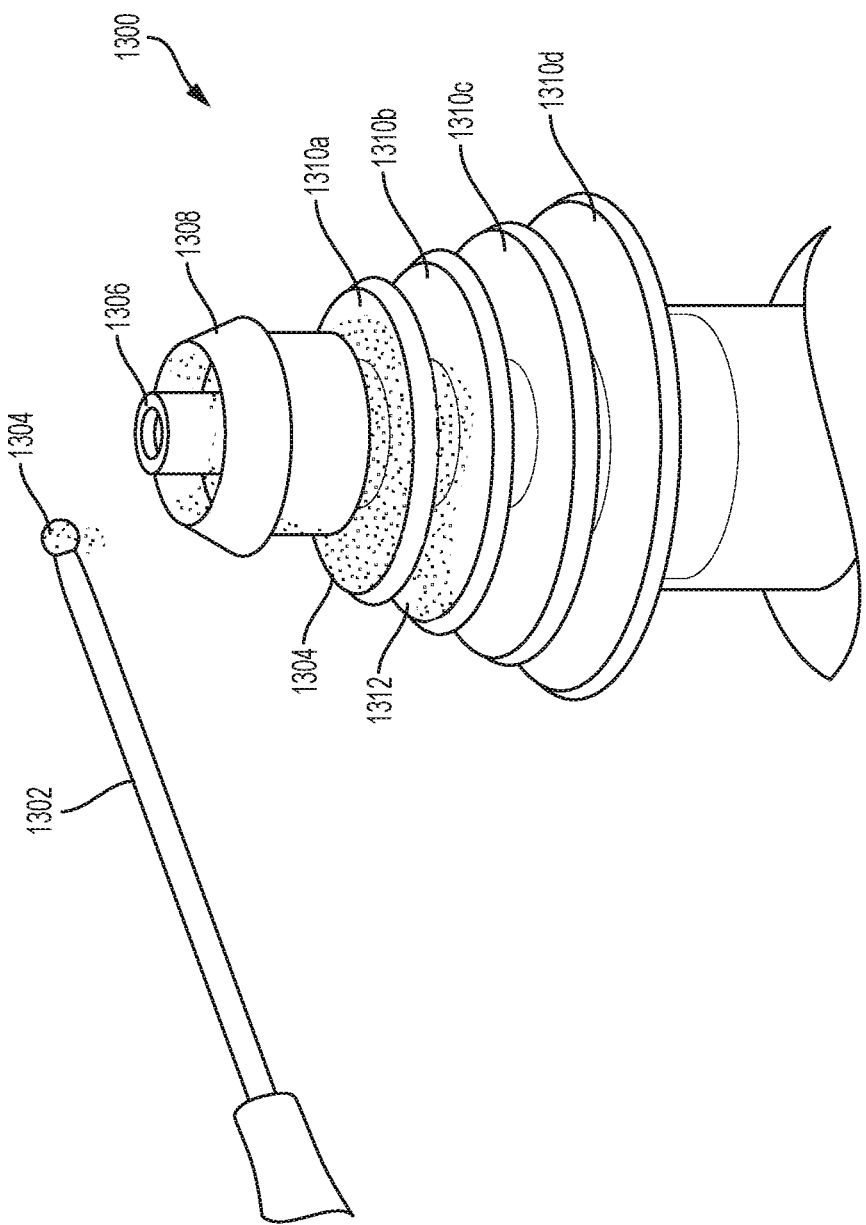

FIG. 76 is the third frame of the sequence after additional drops of fluid 1304 have been dropped onto the fluid wicking tip 1300, according to one aspect of the present disclosure. As clearly shown on the FIG. 76, the drop 1312 that was on the surface of the second tiered drip flange 1310b (see FIG. 75) has been wicked in the narrow circumferential space created between the first and second tiered drip flanges 1310a, 1310b by capillary action. The fluid will be retained in the narrow circumferential space by capillary action and surface tension until a maximum retention volume is reached.

Figure 77:
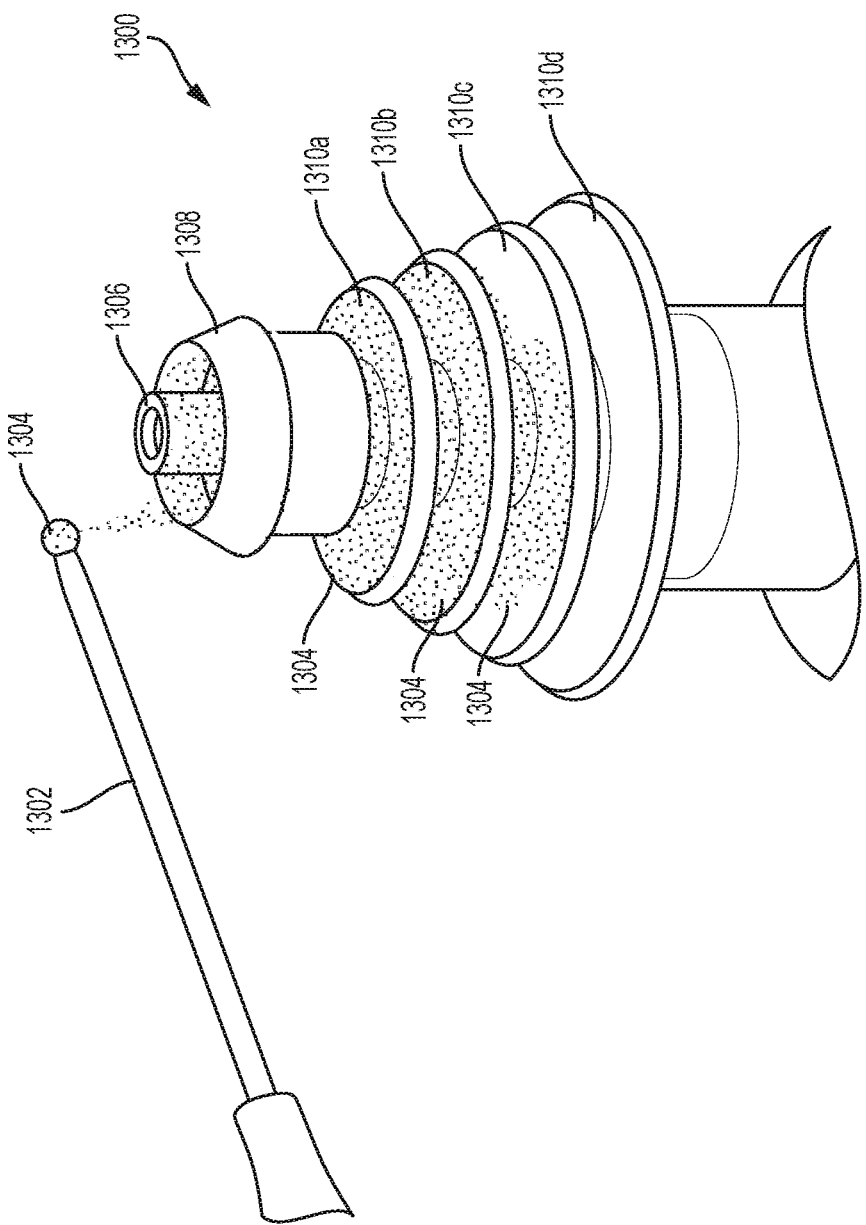

FIG. 77 is the fourth frame in the sequence after additional drops of fluids 1304 have been dropped onto the fluid wicking tip 1300, according to one aspect of the present disclosure. The fluid 1304 is now filling the drip cup 1308 and a substantial volume of fluid 1304 has collected on the surface of the first tiered drip flange 1310a. The narrow circumferential space between the first and second tiered drip flanges 1310a, 1310b has wicked a substantial amount of fluid 1304 and has reached the maximum retention volume. An amount of fluid 1314 is now starting to be wicked in the narrow circumferential space defined between the second and third drip flanges 1301b, 1310c.

Figure 78:
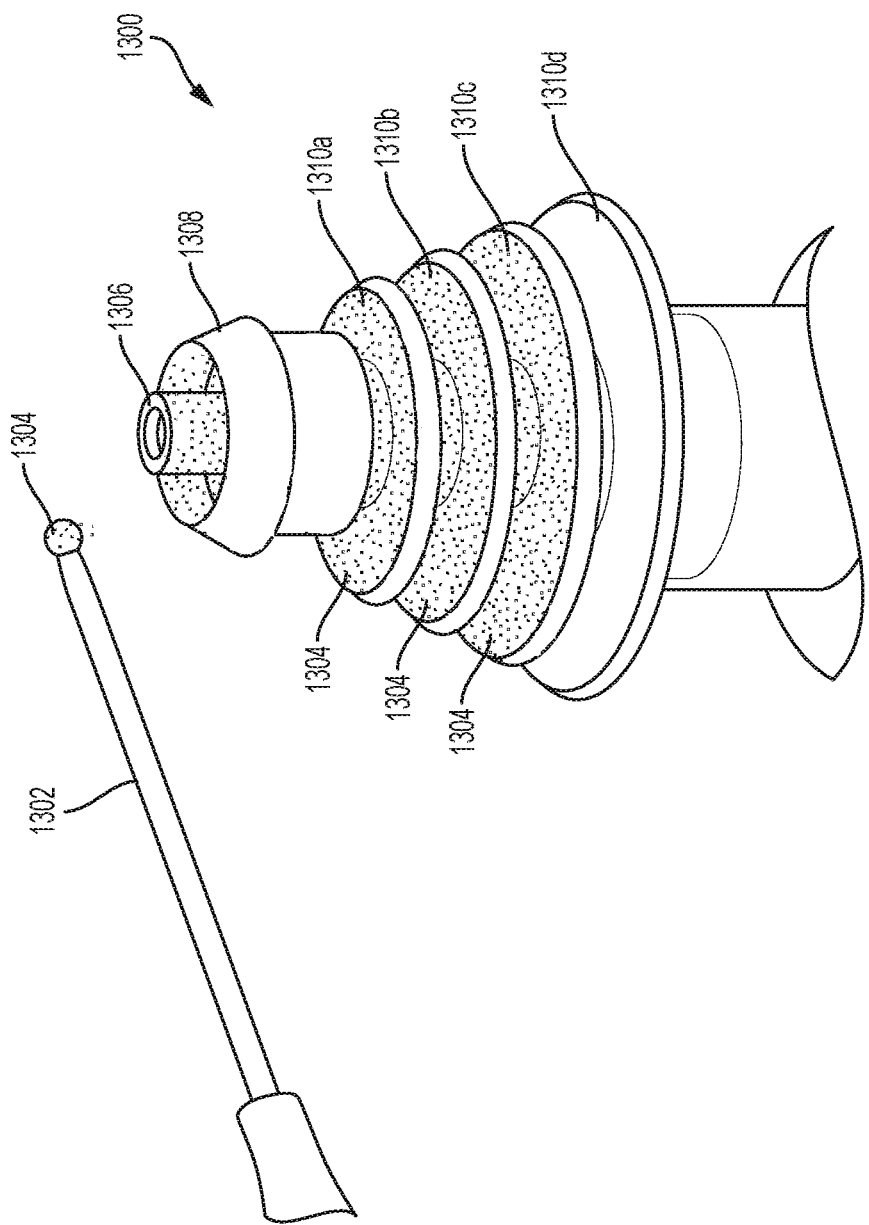

FIG. 78 is the fifth frame of the sequence after additional drops of fluid 1304, having a total volume of 3.0 mL added, have been dropped onto the fluid wicking tip 1300, according to one aspect of the present disclosure. The fluid 1304 now fills the drip cup 1308 and runs over the edge to the surface of the first tiered drip flange 1310a and has been wicked into the narrow circumferential space defined between the first and second tiered drip flanges 1301a, 1310b and the second and third tiered drip flanges 1310b, 1310c. This frame captures the both of these narrow circumferential spaces filled with fluid 1304 up to the maximum retention volume.

Figure 79:
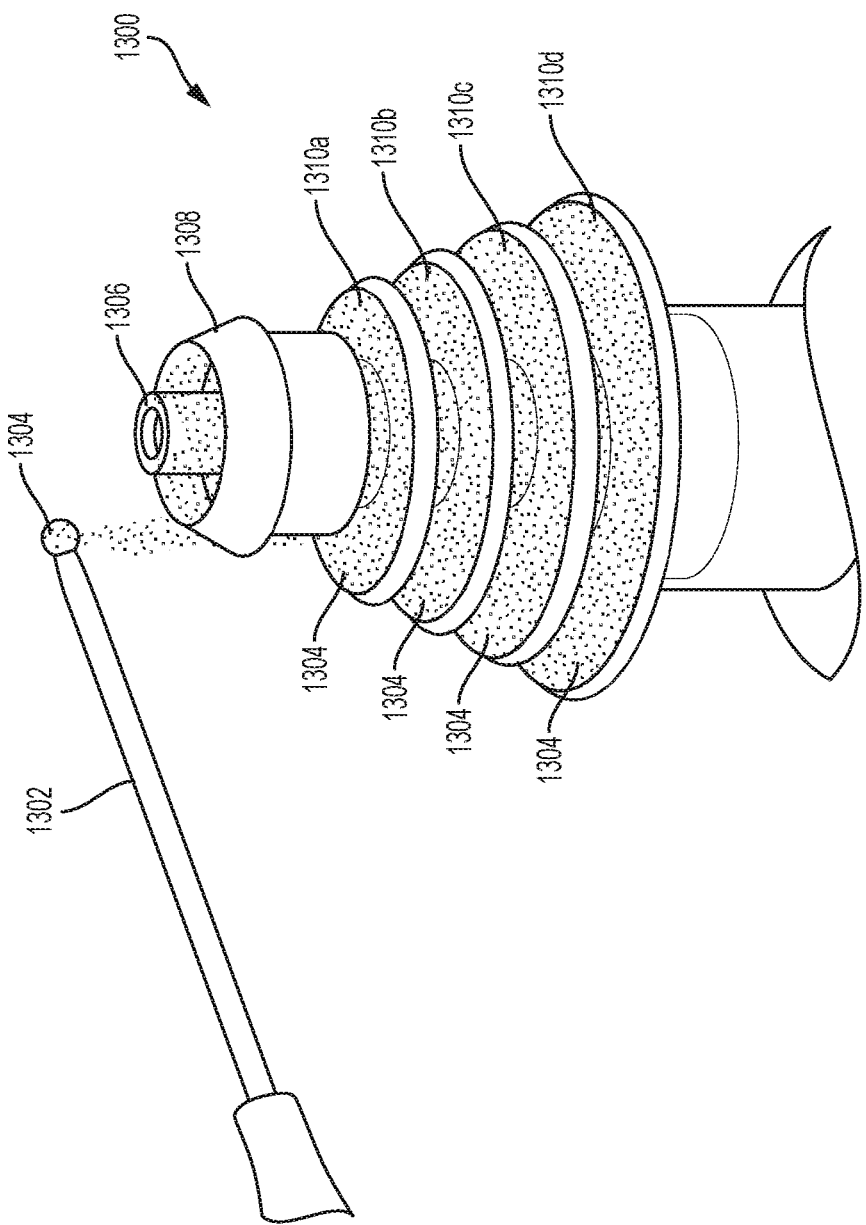

FIG. 79 is the sixth frame of the sequence after additional drops of fluid 1304 have been dropped onto the fluid wicking tip 1300, according to one aspect of the present disclosure. As shown in this frame, a third narrow circumferential space defined between the third and fourth drip flanges 1310c, 1310d. As shown in FIG. 79 the fluid wicking tip 1300 is completely full. The drip cup 1308 is full and all three narrow circumferential spaces defined by the tiered drip flanges 1310a-1310d are at the maximum retention limit. Excess fluid now will simply roll off the sides of the fluid wicking tip 1300. Drip cup 1308 retains its fluid 1304 and the narrow circumferential spaces retain fluid 1304 that has been wicked therebetween.

Figure 80:
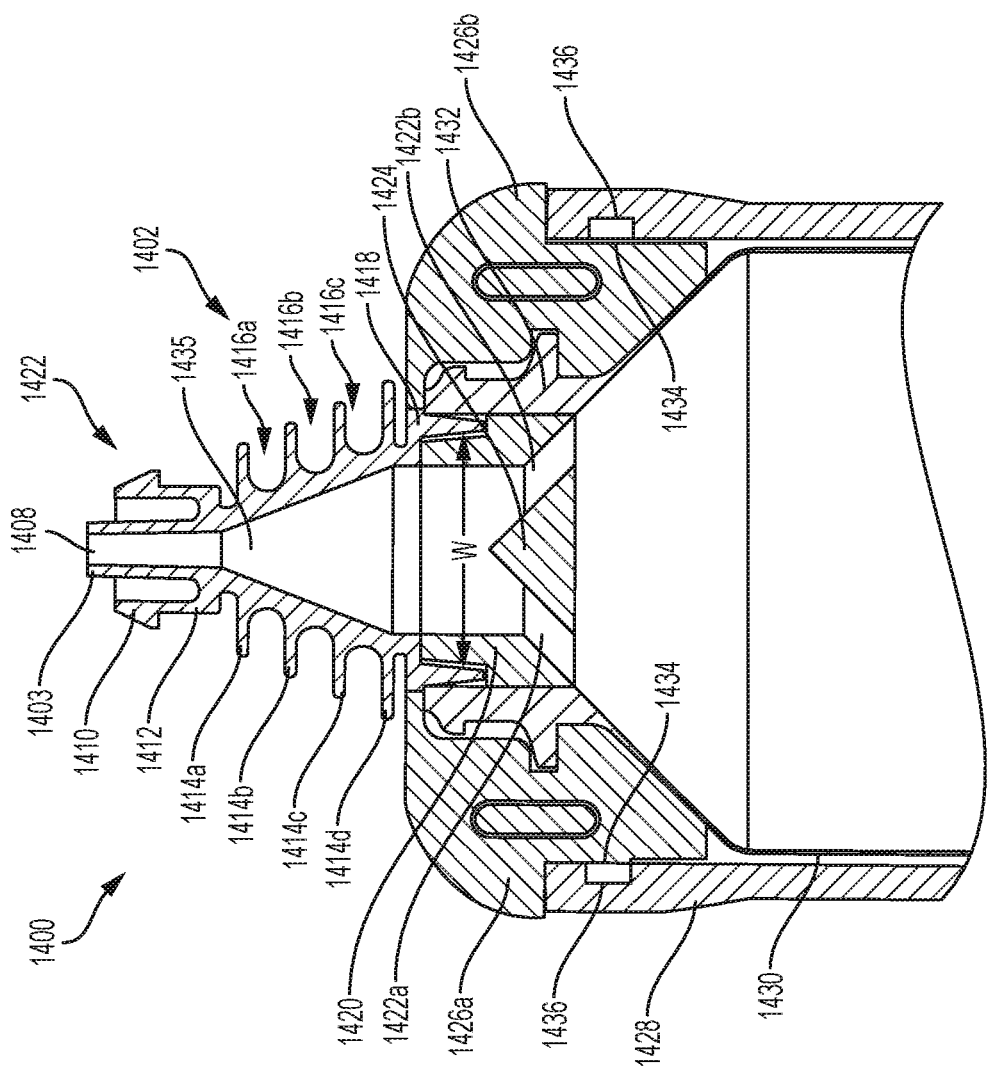
FIG. 80 is a section view of a rolling diaphragm syringe assembly, according to one aspect of the present disclosure.

FIG. 80 illustrates a rolling diaphragm syringe assembly 1400 comprising a fluid wicking tip 1402, first and second collars 1426a, 1426b, a flexible container 1430, a flow diverter 1420, and a pressure jacket 1428. The first and second collars 1426a, 1426b couple the flexible container 1430, the flow diverter 1420, and the fluid wicking tip 1402. Slots 1436 formed on the interior of the pressure jacket 1428 snap onto locking lugs 1434 formed on the exterior of each of the first and second collars 1426a, 1426b to lock the pressure jacket 1428 to the first and second collars 1426a, 1426b.

The fluid wicking tip 1402 comprises a connector tip 1422 fluidly coupled to the flow diverter 1420 and a neck 1432 portion of the flexible container 1430. The connector tip 1422 defines an aperture 1408 for the flow of fluid into and out of the flexible container 1430. The distal tip 1422 comprises a distal tip 1403, a tapered surface 1410, and a cylindrical wall 1410. The connector tip 1422 comprises threads inside the cylindrical wall 1410 for threaded coupling to a flexible tube assembly. In one aspect, the connector tip 1422 is a threaded male luer fitting.

Just below the connector tip 1422, the fluid wicking tip 1402 comprises a plurality of tiered drip flanges 1414a, 1414b, 1414c, 1414d and spaces 1416a, 1416b, 1416c defined between any two adjacent tiered drip flanges 1414a-1414d. As previously discussed, the narrow circumferential spaces 1416a-1416c are sized and configured to wick fluid therebetween by capillary action and to retain fluid therebetween by a combination of surface tension and capillary forces. The fluid wicking tip 1402 further comprises an interface portion 1418 to fluidly couple to the fluid wicking tip 1402 to the mouth 1432 of the flexible container 1430 and to the flow diverter 1420. Notably, the base width "W" of the fluid wicking tip 1402 is wider than the previously described fluid wicking tips 106, 300, 400, 500, 712, 800, 1000, 1102, 1202, 1300, 1400 and also defines a larger flow channel 1435.

The flow diverter 1420 comprises a diverter block 1424 that diverts fluid into or out the flexible container 1430 via flow channels 1422a, 1422b. As previously described, the flow diverter 1420 employs the Coanda effect to fill the flexible container 1430 with fluid while minimizing air bubbles.

The flexible container 1430 is made of a thin walled material. The pressure jacket 1428 is disposed over the flexible container 1430. In one aspect, the flexible container 1430 can be made by a blow molding process.

Figure 81:
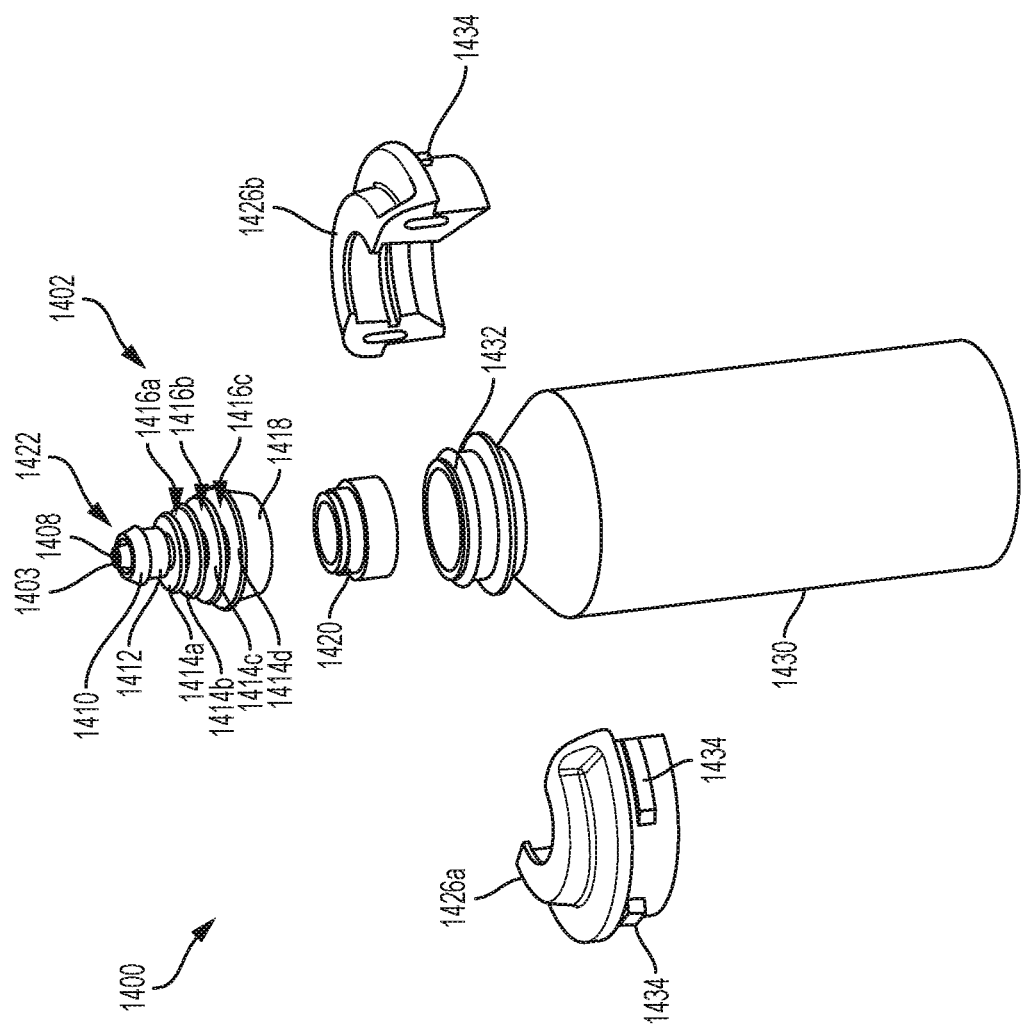
FIG. 81 is an exploded view of the rolling diaphragm syringe assembly shown in FIG. 80 without a pressure jacket, according to one aspect of the present disclosure.
Figure 82:
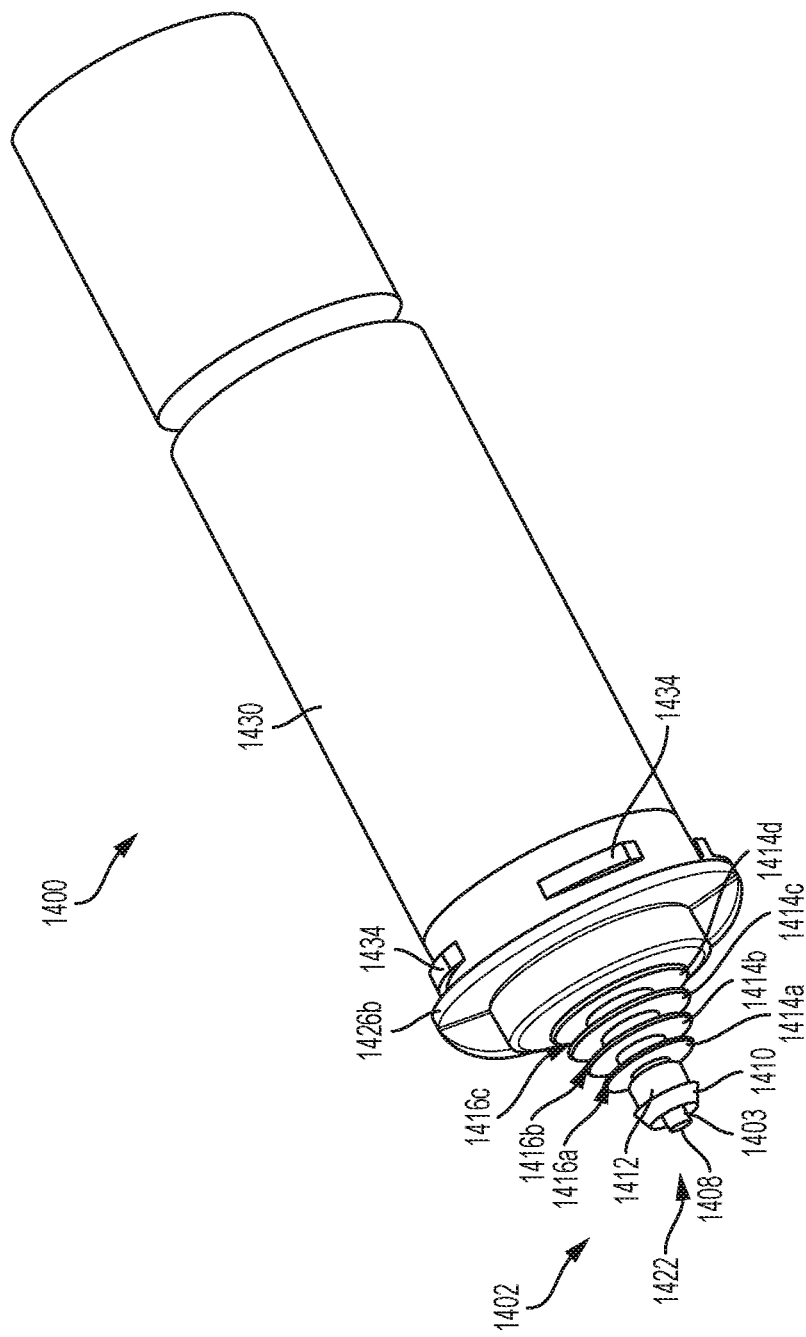
FIG. 82 is a perspective view of the rolling diaphragm syringe assembly shown in FIG. 80 without the pressure jacket, according to one aspect of the present disclosure.
Figure 83:
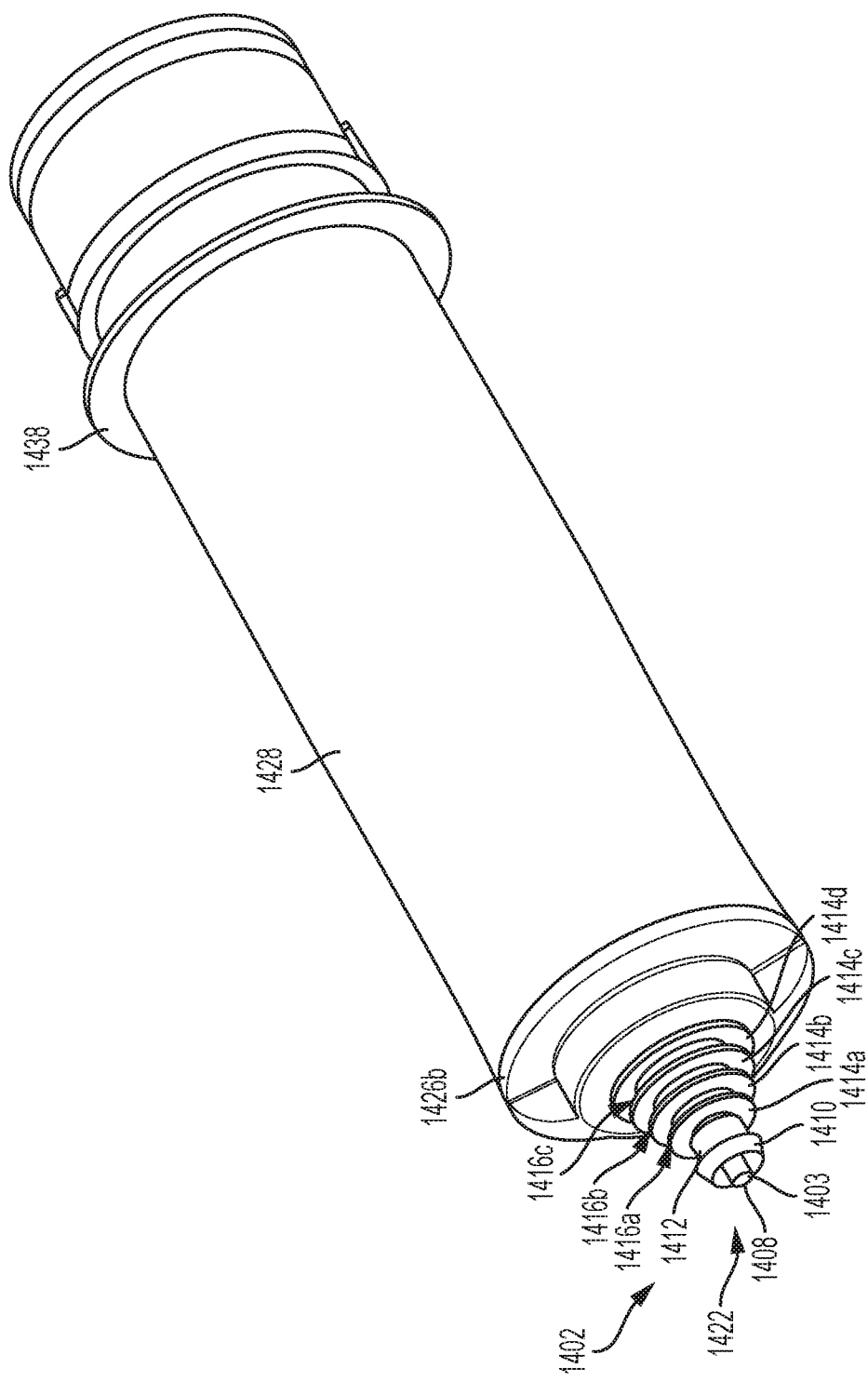
FIG. 83 is a perspective view of the rolling diaphragm syringe assembly shown in FIG. 80, according to one aspect of the present disclosure.

FIG. 81 is an exploded view of the rolling diaphragm syringe assembly 1400 with the pressure jacket 1428 (see FIG. 80) removed. FIG. 82 is a perspective view of the rolling diaphragm syringe assembly 1400 with the pressure jacket 1428 (see FIG. 80) removed. FIG. 83 is a perspective view of the rolling diaphragm syringe assembly 1400 with the pressure jacket 1428 disposed over the flexible container 1430 (see FIGS. 80-82). The pressure jacket 1428 comprises a drip flange 1438 near the proximal end.

Having described various aspects of a fluid wicking tip comprising a plurality of drip flanges arranged in a manner to facilitate wicking fluid in a space defined between the drip flanges by capillary action, the description now turns to various materials and coatings that may be employed to fabricate the fluid wicking tips described herein. In one aspect, the fluid wicking tips 106, 300, 400, 500, 712, 800, 1000, 1102, 1202, 1300, 1400 as well as the tiered drip flanges 614a-614c on the sleeve 604 may be fabricated from polymers such as plastics or similar materials. In one aspect the material may be polycarbonate such as polycarbonate sold under the trade name MAKROLON, Rx2530, clear, 451118 and PET, MH052 clear, for example. The various examples described herein, however, should not be limited in this context.

The fluid wicking tips 106, 300, 400, 500, 712, 800, 1000, 1102, 1202, 1300, 1400 may be coated partially or entirely with hydrophobic or hydrophilic materials to enhance the fluid wicking properties of the tips. In some aspects, the fluid wicking tips may be coated with a combination of hydrophobic and hydrophilic materials placed strategically on the drip flanges to enhance the fluid wicking function of the tips. The various examples described herein, however, should not be limited in this context. In addition, the surfaces of the wicking tips may be smooth or roughened or strategic combinations thereof to maximize wicking and fluid volume retention, optionally in combinations with various hydrophobic and/or hydrophilic coating arrangements.

The gap width "d" defining the distance between two adjacent drip flanges of any of the fluid wicking tips 106, 300, 400, 500, 712, 800, 1000, 1102, 1202, 1300, 1400 described herein may be selected according to the gap width values provided in the graphical depiction 200 of curve 202 in FIG. 12, the graphical depiction 212 of curve 214 in FIG. 15, the graphical depiction 216 of curve 218 in FIG. 16, the graphical depiction 220 of curve 222 in FIG. 17, and in TABLES 2 and 3, for example. For example, the gap width "d" may be selected from a range of: 0.01 in≤d≤0.24 in. In another example, the gap width "d" may be selected from a range of: 0.05 in≤d≤0.20 in. In yet another example, the gap width may be selected from a range of: 0.10 in≤d≤0.15 in. In one aspect, the gap width may be selected as 0.125 in.

Further, in fluid wicking tip examples described herein comprising a drip cup 110 or connector tips 402, 502, 1122, 1222, 1422 a fluid absorbent material may be placed in the opening defined by the drip cup 110 or the connector tips 402, 502, 1122, 1222, 1422 to assist the overall fluid absorbing function of the fluid wicking tips. For example, the drip cups may comprise natural or artificial sponge material or any suitable fluid absorbing material. The various examples described herein, however, should not be limited in this context.

Figure 84:
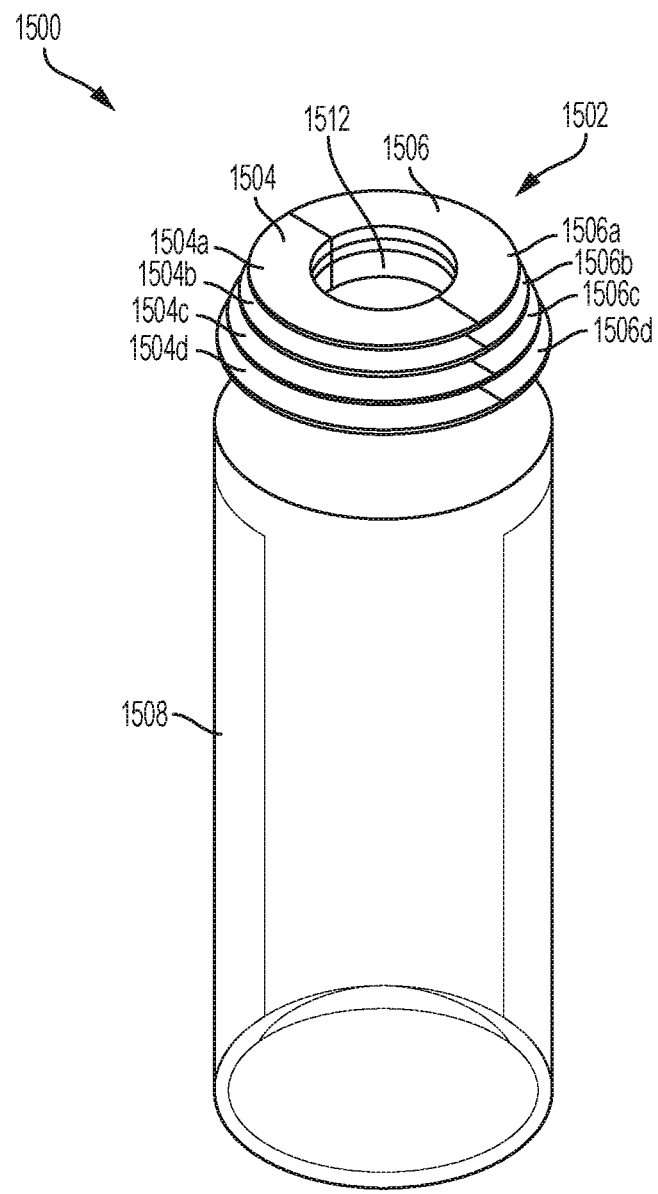
FIG. 84 is a perspective view of a flexible container assembly portion of a rolling diaphragm syringe assembly, according to one aspect of the present disclosure.
Figure 85:
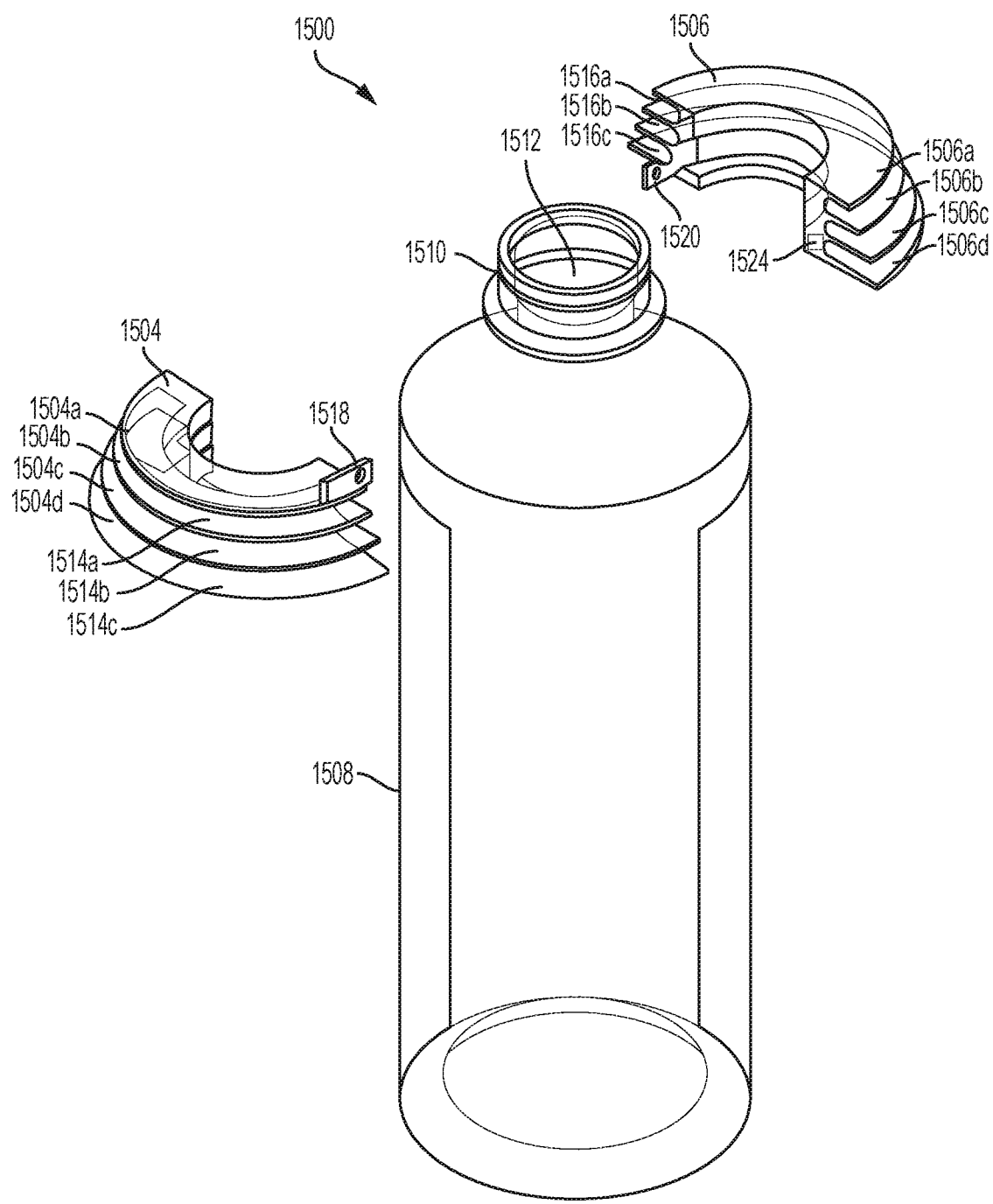
FIG. 85 is a perspective view of the flexible container assembly shown in FIG. 84 and an exploded view of the fluid wicking tip to reveal the neck portion of the flexible container and the two fluid wicking tip components in a disconnected configuration, according to one aspect of the present disclosure.
Figure 86:
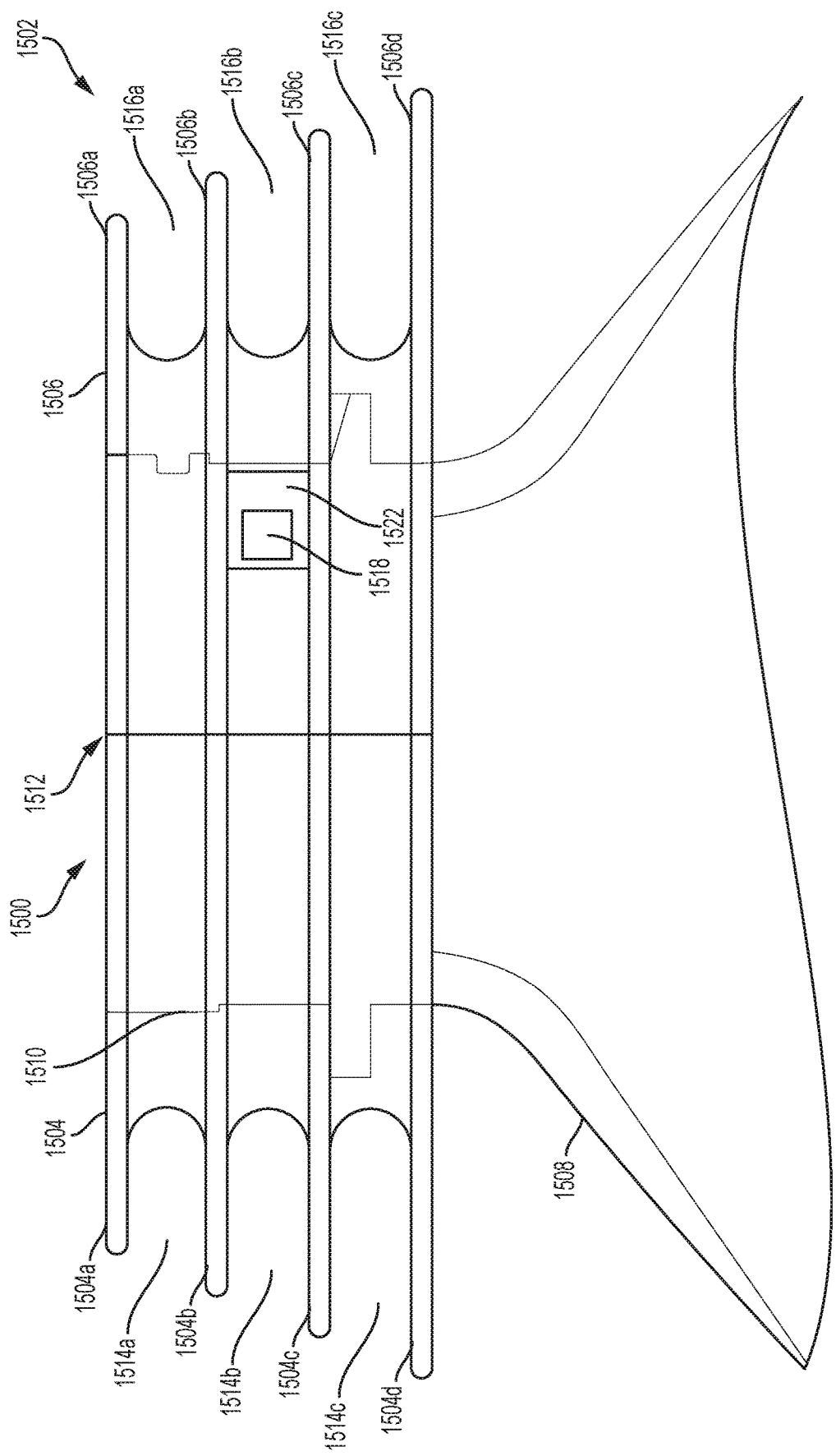
FIG. 86 is an elevation view of the fluid wicking tip, according to one aspect of the present disclosure.
Figure 87:
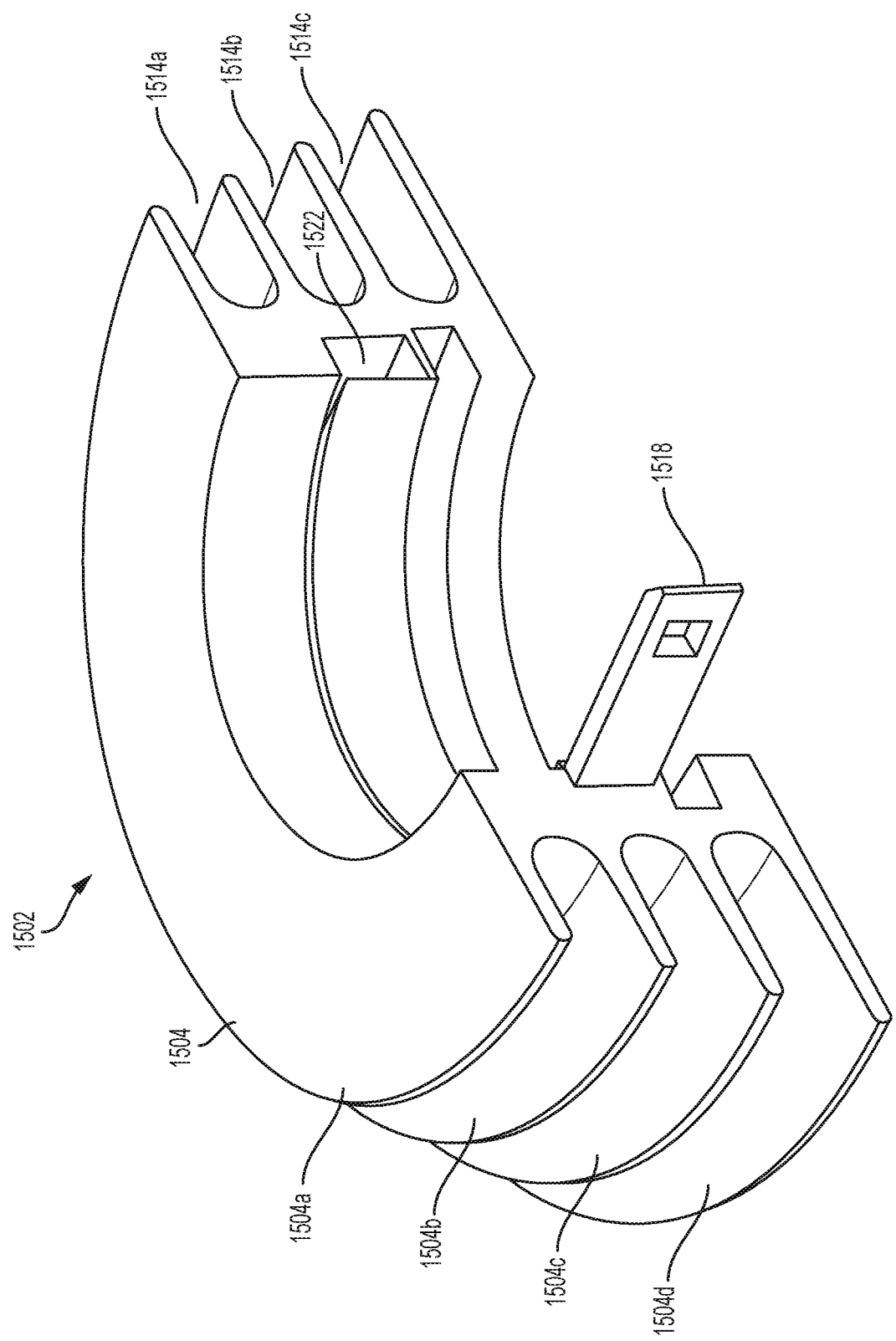
FIGS. 87 and 88 are perspective views of one of the fluid wicking tip components, according to one aspect of the present disclosure.
Figure 88:
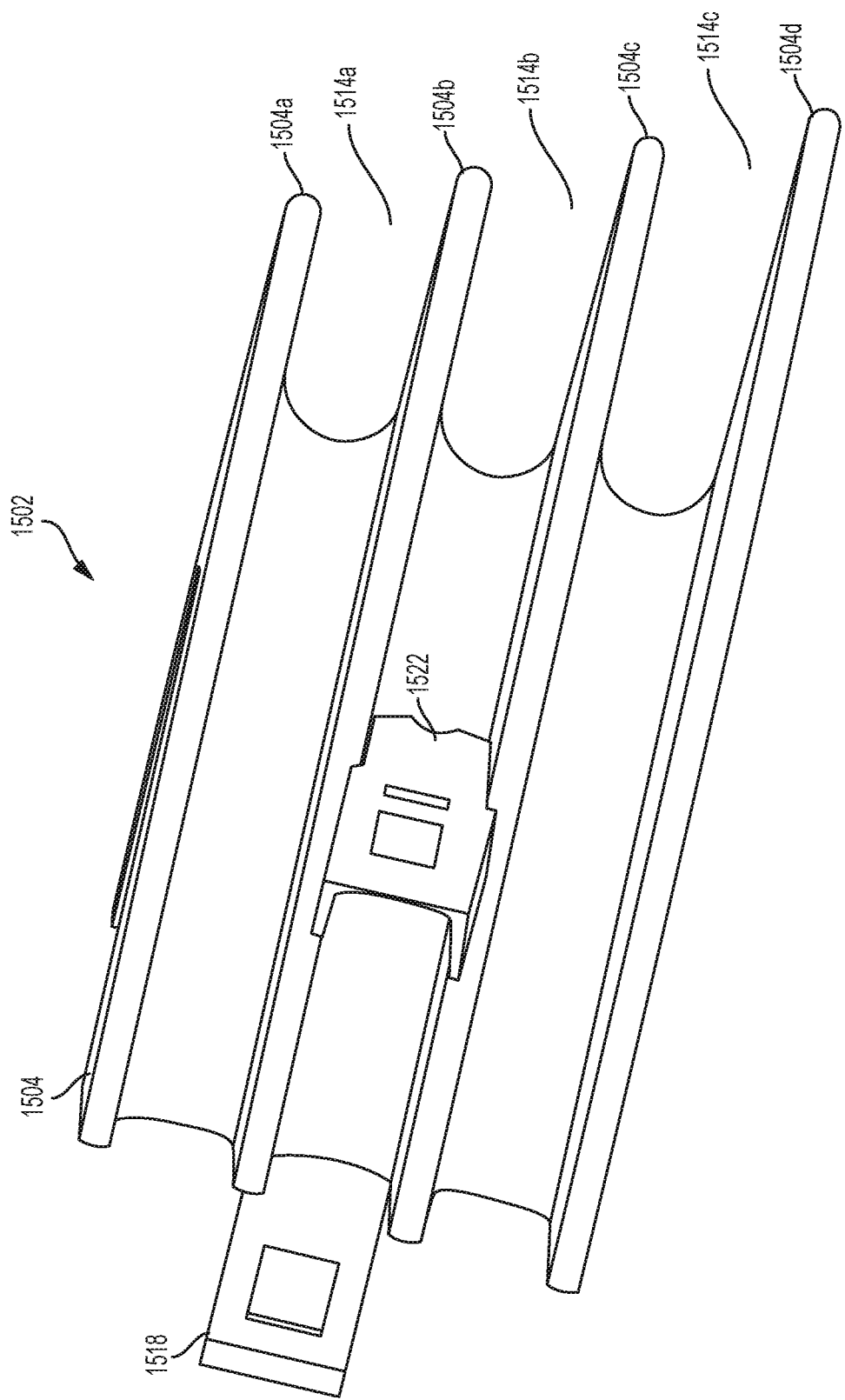

FIG. 84 is a perspective view of a flexible container assembly 1500 portion of a rolling diaphragm syringe assembly, according to one aspect of the present disclosure. Examples of rolling diaphragm syringes suitable for use in the present disclosure are described in International PCT application PCT/US2015/027582, filed Apr. 24, 2015, the disclosure of which is incorporated by this reference. The flexible container assembly 1500 comprising a flexible container 1508 and a fluid wicking tip 1502 positioned thereon. The flexible container assembly 1500 may be combined with the pressure jacket 1428 of the rolling diaphragm syringe assembly 1400 described in connection with FIG. 80. The fluid wicking tip 1502 comprises two components 1504, 1506 that are connected by snap joints. FIG. 85 is a perspective view of the flexible container assembly 1500 and an exploded view of the fluid wicking tip 1502 to reveal the neck 1510 portion of the flexible container 1508 and the two fluid wicking tip components 1504, 1506 in a disconnected configuration. An aperture 1512 is defined by the fluid wicking tip 1502 and the flexible container 1508 to enable the flow of fluid into and out of the flexible container 1508. FIG. 86 is an elevation view of the fluid wicking tip 1502. FIGS. 87 and 88 are perspective views of one of the fluid wicking tip components 1504.

With reference now to FIGS. 84-88, each of the fluid wicking tip components 1504, 1506 comprises a plurality of tiered flanges. One fluid wicking tip component 1504 comprises a plurality of tiered flanges 1504a, 1504b, 1504c, 1504d defining spaces 1514a, 1514b, 1514c between any two adjacent tiered drip flanges 1504a-1504d. Similarly, the other fluid wicking tip component 1506 comprises a plurality of tiered flanges 1506a, 1506b, 1506c, 1506d defining spaces 1516a, 1516b, 1516c between any two adjacent tiered drip flanges 1506a-1506d. Each of the fluid wicking tip components 1504, 1506 also comprises a fastener to join the fluid wicking tip components 1504, 1506. Each fastener comprises a snap-fit clip 1518, 1520 and a catch or aperture 1522, 1524 to receive the snap-fit clip 1518, 1520 and form a reliable snap-fit joint to join the two corresponding fluid wicking tip components 1504, 1506 about the neck 1510 portion of the flexible container 1608.

Figure 89:
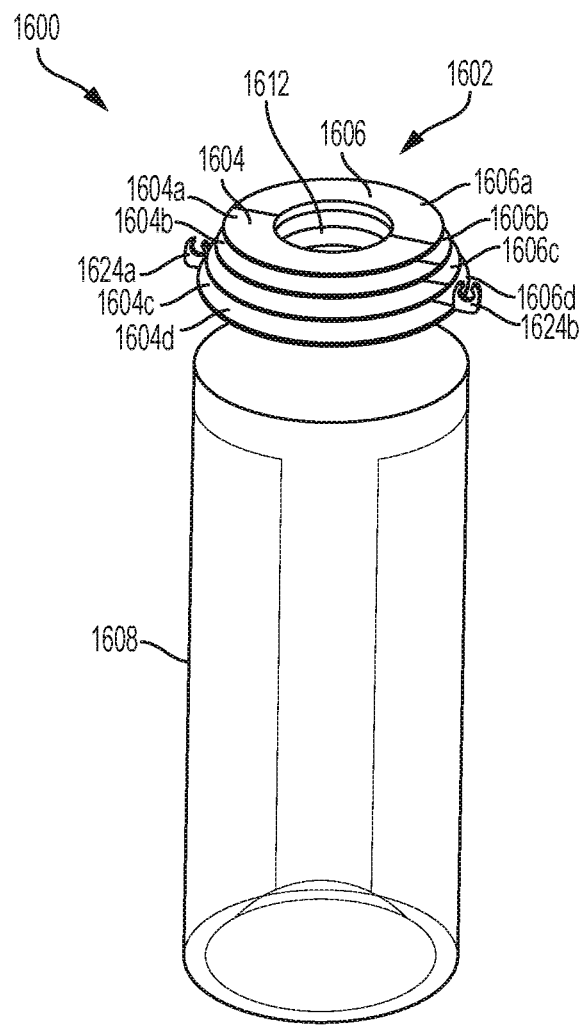
FIG. 89 is a perspective view of a flexible container assembly portion of a rolling diaphragm syringe assembly, according to one aspect of the present disclosure.
Figure 90:
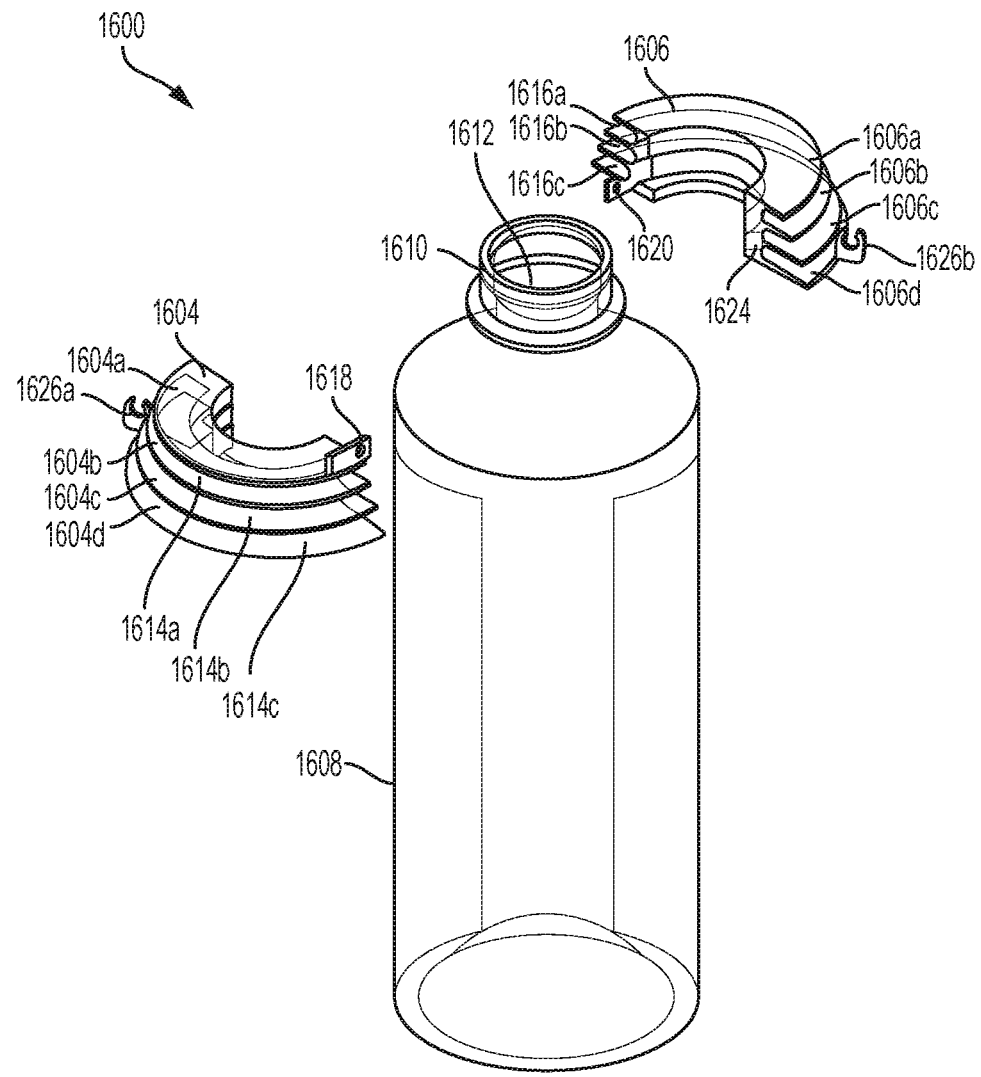
FIG. 90 is a perspective view of the flexible container assembly shown in FIG. 89 and an exploded view of the fluid wicking tip to reveal the neck portion of the flexible container and the two fluid wicking tip components in a disconnected configuration, according with one aspect of the present disclosure.
Figure 91:
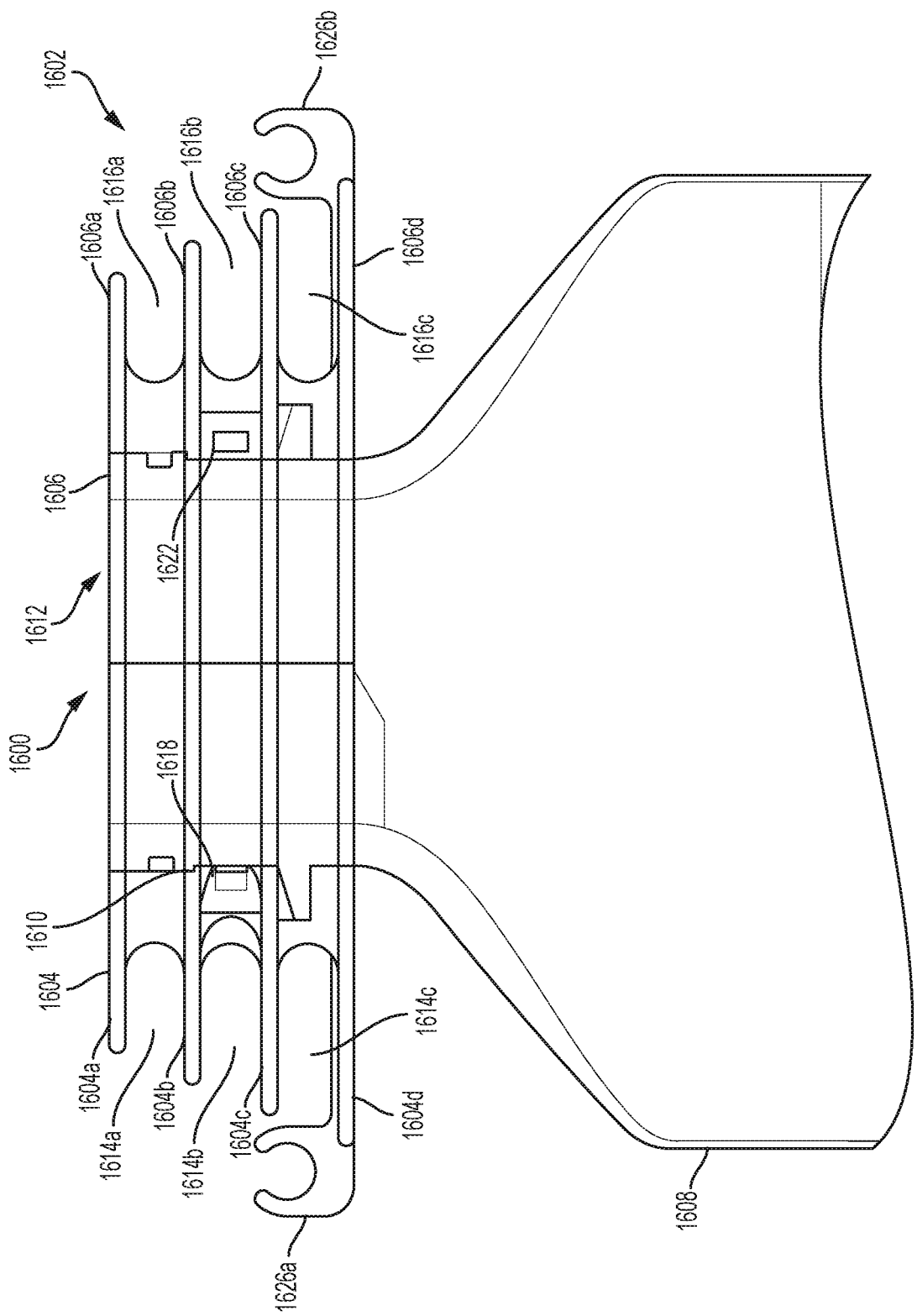
FIG. 91 is an elevation view of the fluid wicking tip, according to one aspect of the present disclosure.
Figure 92:
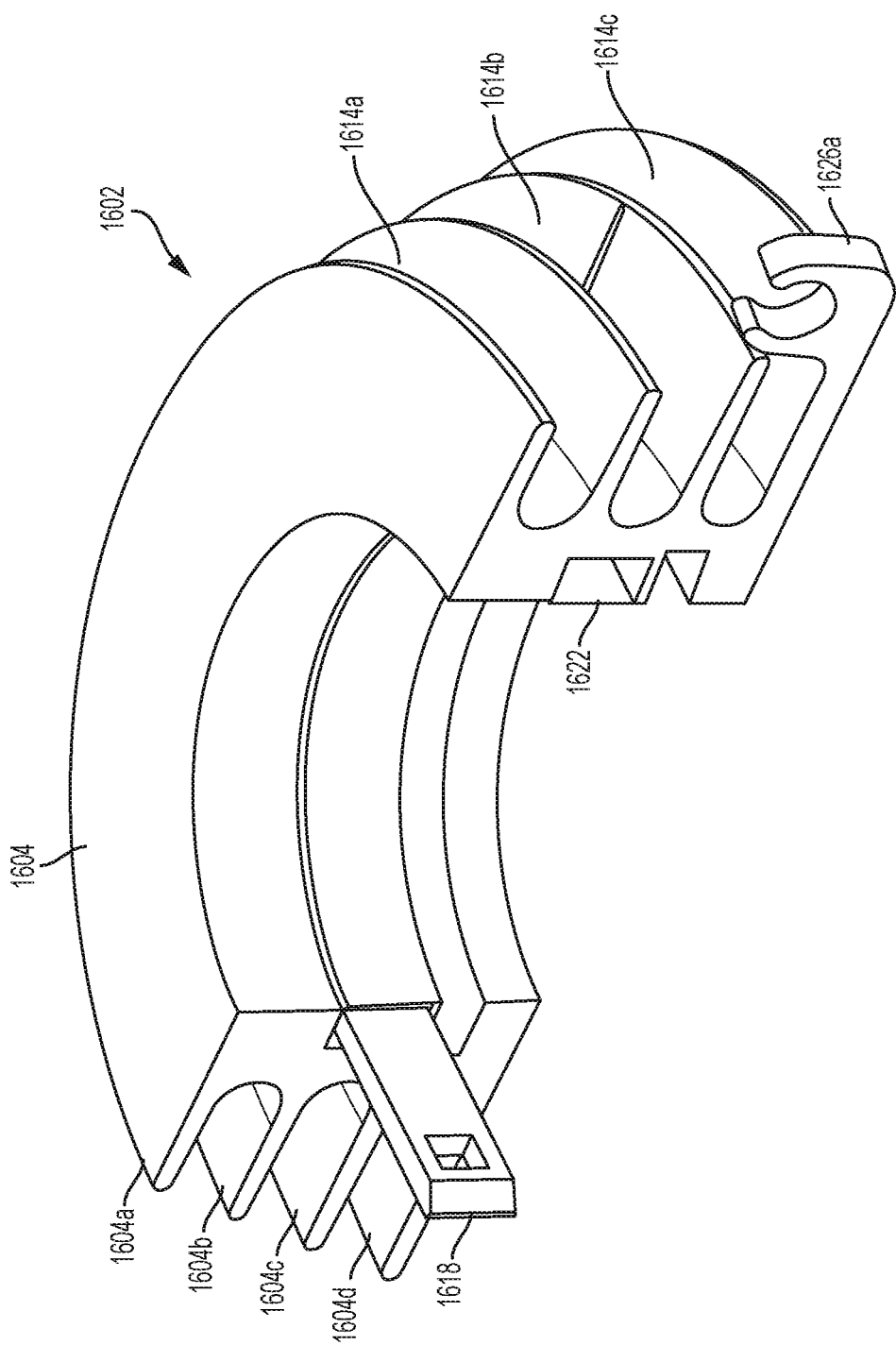
FIGS. 92 and 93 are perspective views of one of the fluid wicking tip components, according to one aspect of the present disclosure.
Figure 93:
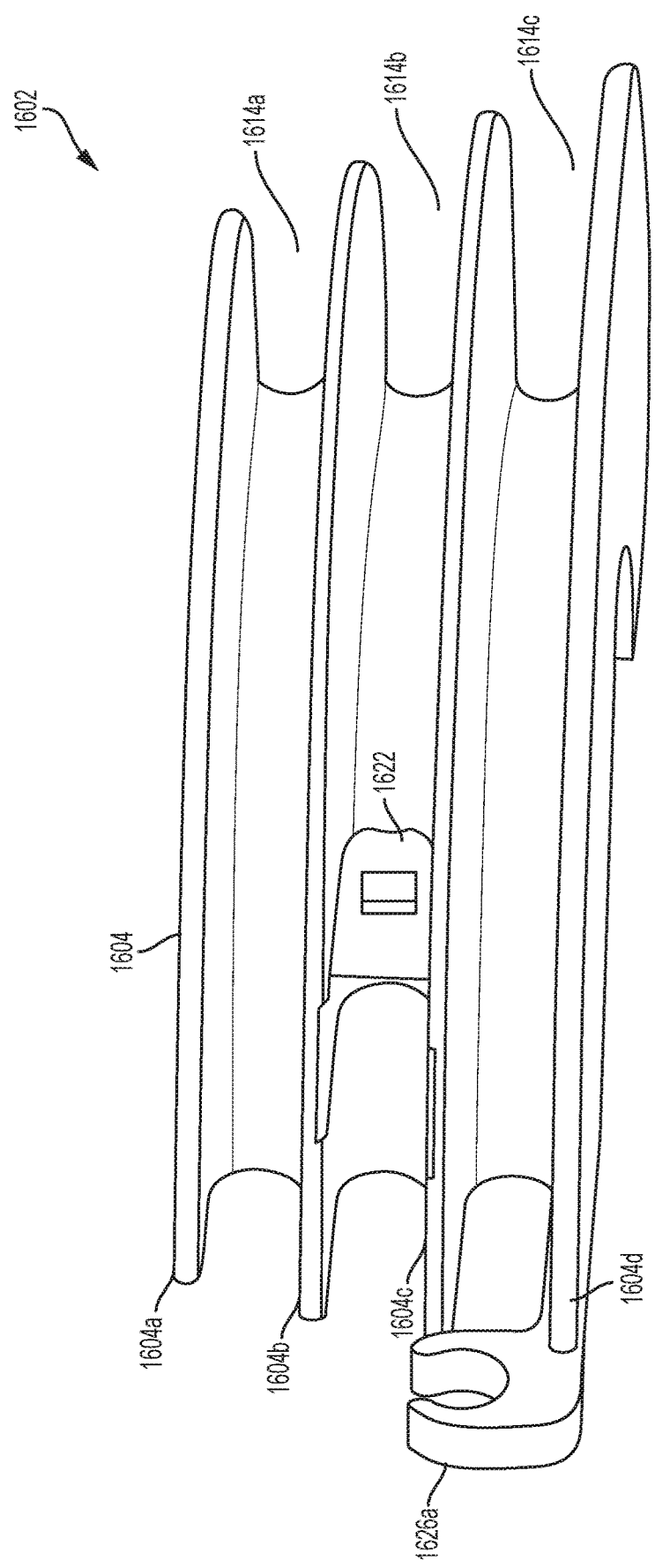

FIG. 89 is a perspective view of a flexible container assembly 1600 portion of a rolling diaphragm syringe assembly, according to one aspect of the present disclosure. The flexible container assembly 1600 comprising a flexible container 1608 and a fluid wicking tip 1602 positioned thereon. The flexible container assembly 1600 may be combined with the pressure jacket 1428 of the rolling diaphragm syringe assembly 1400 described in connection with FIG. 80. The fluid wicking tip 1602 comprises two components 1604, 1606 that are connected by snap joints. Each of the fluid wicking tip components 1604, 1606 comprises a tubing clip 1626a, 1626b, respectively. FIG. 90 is a perspective view of the flexible container assembly 1600 and an exploded view of the fluid wicking tip 1602 to reveal the neck 1610 portion of the flexible container 1608 and the two fluid wicking tip components 1604, 1606 in a disconnected configuration. An aperture 1612 is defined by the fluid wicking tip 1502 and the flexible container 1608 to enable the flow of fluid into and out of the flexible container 1608. FIG. 91 is an elevation view of the fluid wicking tip 1602. FIGS. 92 and 93 are perspective views of one of the fluid wicking tip components 1604.

With reference now to FIGS. 89-93, each of the fluid wicking tip components 1604, 1606 comprises a plurality of tiered flanges. One fluid wicking tip component 1604 comprises a plurality of tiered flanges 1604a, 1604b, 1604c, 1604d defining spaces 1614a, 1614b, 1614c between any two adjacent tiered drip flanges 1604a-1604d. Similarly, the other fluid wicking tip component 1606 comprises a plurality of tiered flanges 1606a, 1606b, 1606c, 1606d defining spaces 1616a, 1616b, 1616c between any two adjacent tiered drip flanges 1606a-1606d. Each of the fluid wicking tip components 1604, 1606 also comprises a fastener to join the fluid wicking tip components 1604, 1606 and tubing clips 1626a, 1626b formed integrally therewith. For example the tubing clips 1626a, 1626b may be molded together with the each of the corresponding fluid wicking tip components 1604, 1606. Each fastener comprises a snap-fit clip 1618, 1620 and a catch or aperture 1622, 1624 to receive the snap-fit clip 1618, 1620 and form a reliable snap-fit joint to join the two corresponding fluid wicking tip components 1604, 1606 about the neck 1610 portion of the flexible container 1608.

While various aspects of the syringe tip comprising fluid wicking flanges have been described in the context of syringes for powered medical injectors, the fluid wicking tips described herein may also be incorporated into handheld syringes for delivering fluids at low injection pressures. For example, in many medical settings where a fluid is to be injected by a handheld syringe, the physician may draw a fluid into the syringe from a corresponding fluid container, such as a vial, and then may prime or purge the syringe of any air by holding the syringe in a vertical position and pressing on the plunger assembly to deliver a small amount of the fluid along with any air contained within the syringe. The ejected fluid may drip down the side of the needle and the syringe body, potentially exposing the physician to contact with the medical fluid. The syringe drip tip with wicking flanges described herein may be utilized on a handheld syringe to prevent drips of the fluid, either that ejected during the priming process or fluid drips during an injection process, from contacting to physician or dripping onto surfaces. Handheld syringed comprising various embodiments of the fluid wicking flange tips are within the scope of this disclosure.

Still other aspects of the present disclosure relate to other medical devices comprising the fluid wicking flanges described herein. For example, any medical devices that deliver fluids which may include leaking or dripping of small amounts of fluid from a fluid aperture to a surface thereof may benefit from the fluid wicking flanges of the present disclosure. Examples of such medical devices include, but are not limited to, catheters (such as the distal end or those portions positioned immediately outside the patients body), tubing sets, IV lines, tubing connectors and clips, shunts, fluid manifolds, valves, aspiration tubing, surgical tools, pump fluid outputs, and the like may all be modified to include the fluid wicking flange assemblies described herein.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "operative," "adapted," etc. Those skilled in the art will recognize that "configured to" can generally encompass active-state components and/or inactive-state components and/or standby-state components, unless context requires otherwise.

While particular aspects of the subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

In summary, numerous benefits have been described which result from employing the concepts described herein. The foregoing disclosure has been presented for purposes of illustration and description. It is not intended to be exhaustive or limiting to the precise form disclosed. Modifications or variations are possible in light of the above teachings. It is intended that the claims submitted herewith define the overall scope of the present disclosure.

The invention claimed is:

1. A fluid wicking tip for a syringe, comprising a body defining a fluid channel and a plurality of drip flanges forming solid surfaces and extending radially outward from the body, the drip flanges arranged to wick fluid into a gap width defined between any two of the solid surfaces of any two adjacent drip flanges, and
   a connector configured for connecting to a fitting on a conical portion of a distal end of the syringe;
   wherein each of the plurality of drip flanges has a length in a direction radially outward from the body, wherein the length of the distal most drip flange has the shortest length and the length of each successive drip flange is longer than the length of its distally adjacent drip flange, such that the plurality of drip flanges together define a conical shape, and
   wherein the gap width is less than 0.25 inch to facilitate wicking by capillary action and such that fluid introduced in the gap width defined between the solid surfaces of the adjacent drip flanges forms a capillary bridge or fluid bridge between the solid surfaces of the adjacent drip flanges, the capillary bridge or fluid bridge causing an attractive adhesive force between the solid surfaces of the adjacent drip flanges due to decreased pressure inside the capillary bridge or fluid bridge and due to direct action of a surface tension force exerted around an annulus formed by the solid surfaces of the adjacent drip flanges.

2. The fluid wicking tip of claim 1, wherein the drip flanges are arranged in at least two tiers.

3. The fluid wicking tip of claim 1, further comprising a drip cup positioned distal to the plurality of drip flanges.

4. The fluid wicking tip of claim 1, further comprising a drip cup positioned proximal to the plurality of drip flanges.

5. The fluid wicking tip of claim 1, wherein the plurality of drip flanges are flat and smooth and continuous around a circumference of the fluid wicking tip.

6. The fluid wicking tip of claim 1, wherein the plurality of drip flanges are discontinuous around a circumference of the wicking tip and wherein each drip flange is staggered relative to an immediately adjacent drip flange.

7. The fluid wicking tip of claim 1, wherein the plurality of drip flanges have a ruffled profile.

8. The fluid wicking tip of claim 1, further comprising a piercing tip fluidly coupled to an interior of the syringe.

9. The fluid wicking tip of claim 1, wherein each distally located drip flange of the plurality of drip flanges comprises an opening to facilitate draining of fluid from a distal drip flange to a more proximately located drip flange.

10. The fluid wicking tip of claim 1, wherein the connector is a luer fitting sized and configured to fluidly couple to an interior of the syringe.

11. The fluid wicking tip of claim 1, wherein the connector is a luer fitting sized and configured to fluidly couple to and fluidly connect an interior of the syringe with a flexible tube assembly.

12. The fluid wicking tip of claim 1, wherein the drip flanges are arranged perpendicular to a vertical axis of the syringe.

13. The fluid wicking tip of claim 1, wherein the drip flanges are angled with respect to a vertical axis of the syringe and are not parallel relative to each other.

14. A syringe, comprising: a body defining a cylindrical fluid chamber having a distal end and a proximal end, a tapered portion extending from the distal end of the cylindrical fluid chamber, and a tip having a fitting extending from the tapered portion; and a fluid wicking tip fluidly coupled to the fitting of the syringe, the fluid wicking tip comprising a body defining a fluid channel and a plurality of drip flanges forming solid surfaces and extending radially outward from the body of the fluid wicking tip, the drip flanges arranged to wick fluid into a gap width defined between any two of the solid surfaces of any two adjacent drip flanges, and a connector configured for connecting to the fitting on the syringe, wherein each of the plurality of drip flanges has a length in a direction radially outward from the body of the fluid wicking tip, wherein the length of the distal most drip flange has the shortest length and the length of each successive drip flange is longer than the length of its distally adjacent drip flange, such that the plurality of drip flanges together define a conical shape, and wherein the gap width is less than 0.25 inch to facilitate wicking by capillary action and such that fluid introduced in the gap width defined between the solid surfaces of the adjacent drip flanges forms a capillary bridge or fluid bridge between the solid surfaces of the adjacent drip flanges, the capillary bridge or fluid bridge causing an attractive adhesive force between the solid surfaces of the adjacent drip flanges due to decreased pressure inside the capillary bridge or fluid bridge and due to direct action of a surface tension force exerted around an annulus formed by the solid surfaces of the adjacent drip flanges.

15. The syringe of claim 14, further comprising a piercing tip fluidly coupling the fluid wicking tip and an interior of the syringe.

16. The syringe of claim 14, wherein the fluid wicking tip is integrally formed with the fitting extending from the tapered portion of the distal end of the syringe.

* * * * *

UNITED STATES PATENT AND TRADEMARK OFFICE
CERTIFICATE OF CORRECTION

PATENT NO. : 11,642,464 B2
APPLICATION NO. : 15/777928
DATED : May 9, 2023
INVENTOR(S) : McDermott et al.

It is certified that error appears in the above-identified patent and that said Letters Patent is hereby corrected as shown below:

In the Drawings

In Fig. 12, Sheet 7 of 64, in Line 1, delete "Retension" and insert -- Retention --, therefor.
In Fig. 15, Sheet 9 of 64, in Line 1, delete "Retension" and insert -- Retention --, therefor.
In Fig. 16, Sheet 10 of 64, in Line 1, delete "Retension" and insert -- Retention --, therefor.
In Fig. 16, Sheet 10 of 64, in Line 3, delete "Retension" and insert -- Retention --, therefor.
In Fig. 16, Sheet 10 of 64, in Lines 9-11, delete "Retension" and insert -- Retention --, therefor.

In the Specification

In Column 2, Line 4, delete "use" and insert -- used --, therefor.
In Column 2, Line 40, delete "example claim" and insert -- example --, therefor.
In Column 4, Line 16, delete "NOT" and insert -- not --, therefor.
In Column 4, Line 38, delete "2 is" and insert -- 2 is a --, therefor.
In Column 8, Line 39, delete "according with" and insert -- according to --, therefor.
In Column 10, Line 50, delete "2 is" and insert -- 2 is a --, therefor.
In Column 12, Line 10, delete "where is" and insert -- where in --, therefor.
In Column 12, Lines 38-39, delete "http://lcpe.uni-sofia.bg/files/punblications/" and insert -- http://www.lcpe.uni-sofia.bg/files/publications/ --, therefor.
In Column 12, Line 58, delete "(I)" and insert -- (1) --, therefor.
In Columns 13 & 14, in Table 1, Line 5, delete "Lnn," and insert -- Lun, --, therefor.
In Columns 13 & 14, in Table 1, Line 11, delete "±(ρ1E (ϕ1." and insert -- ±(ρ1E(ϕ1. --, therefor.
In Columns 13 & 14, in Table 1, Line 12, delete "ρ2)1/2/ρ }" and insert -- ρ2)]1/2/ρ} --, therefor.
In Columns 13 & 14, in Table 1, Line 16, delete "(ρρ1)" and insert -- (ρρ1)} --, therefor.
In Column 15, Line 40, delete "volume" and insert -- volume of --, therefor.
In Column 16, Line 39, delete "(in)" and insert -- (in)) --, therefor.
In Column 16, Line 53, delete "volume" and insert -- volume of --, therefor.
In Column 24, Line 54, delete "1114c, 1114c" and insert -- 1114c, 1114d --, therefor.
In Column 25, Lines 35-36, delete "1214c each" and insert -- 1214d each --, therefor.
In Column 26, Line 53, delete "with the" and insert -- with --, therefor.

Signed and Sealed this
Twenty-ninth Day of August, 2023

*Katherine Kelly Vidal*
Katherine Kelly Vidal
*Director of the United States Patent and Trademark Office*

CERTIFICATE OF CORRECTION (continued)
U.S. Pat. No. 11,642,464 B2

In Column 27, Line 31, delete "to ne" and insert -- to one --, therefor.
    In Column 27, Line 44, delete "is a" and insert -- are a --, therefor.
    In Column 28, Line 31, delete "the both" and insert -- both --, therefor.
    In Column 29, Line 18, delete "out" and insert -- out of --, therefor.
    In Column 31, Line 31, delete "with the" and insert -- with --, therefor.
    In Column 32, Line 2, delete "patients" and insert -- patient's --, therefor.